(12) United States Patent
Nagel et al.

(10) Patent No.: US 11,832,662 B2
(45) Date of Patent: Dec. 5, 2023

(54) METHODS AND DEVICES FOR PREVENTING VIRAL TRANSMISSION

(71) Applicant: Vomaris Innovations, Inc., Tempe, AZ (US)

(72) Inventors: Michael Nagel, Tempe, AZ (US); Mary Maijer, Tempe, AZ (US)

(73) Assignee: Vomaris Innovations, Inc., Tempe, AZ (US)

( * ) Notice: Subject to any disclaimer, the term of this patent is extended or adjusted under 35 U.S.C. 154(b) by 149 days.

(21) Appl. No.: 16/877,056

(22) Filed: May 18, 2020

(65) Prior Publication Data

US 2021/0282475 A1 Sep. 16, 2021

Related U.S. Application Data

(60) Provisional application No. 62/987,786, filed on Mar. 10, 2020, provisional application No. 62/988,739, (Continued)

(51) Int. Cl.
| | | |
|---|---|---|
| *A41D 13/11* | (2006.01) | |
| *A61L 9/16* | (2006.01) | |
| *A61L 9/22* | (2006.01) | |
| *A41D 13/00* | (2006.01) | |
| *A61F 9/04* | (2006.01) | |

(52) U.S. Cl.
CPC ...... *A41D 13/1192* (2013.01); *A41D 13/0012* (2013.01); *A41D 13/11* (2013.01); *A61L 9/16* (2013.01); *A61L 9/22* (2013.01); *A41D 13/1161* (2013.01); *A41D 2300/328* (2013.01); *A61F 9/04* (2013.01); *A61L 2209/133* (2013.01); *A61L 2209/14* (2013.01); *A61L 2209/15* (2013.01); *A61L 2209/21* (2013.01)

(58) Field of Classification Search
CPC ............... A41D 13/11; A41D 13/1169; A41D 13/1192; A41D 31/02; A41D 31/30; A41D 31/305; A61L 9/16; A62B 7/10; A62B 23/00
See application file for complete search history.

(56) References Cited

U.S. PATENT DOCUMENTS

| | | | | |
|---|---|---|---|---|
| 5,139,684 A | * | 8/1992 | Kaali ................ | A61L 2/0011 204/164 |
| 7,904,147 B2 | * | 3/2011 | Schneider ............ | A41B 11/006 607/2 |

(Continued)

OTHER PUBLICATIONS

Kumagai, E., Tominaga, M., & Harada, S. (2011). Sensitivity to electrical stimulation of human immunodeficiency virus type 1 and MAGIC-5 cells. AMB Express, 1(1), 23. https://doi.org/10.1186/2191-0855-1-23 (Year: 2011).*

*Primary Examiner* — Keri J Nelson
(74) *Attorney, Agent, or Firm* — K&L Gates LLP; Louis C. Cullman; Hal Gibson

(57) ABSTRACT

An apparatus includes multiple first reservoirs and multiple second reservoirs joined with a substrate. Selected ones of the multiple first reservoirs include a reducing agent, and first reservoir surfaces of selected ones of the multiple first reservoirs are proximate to a first substrate surface. Selected ones of the multiple second reservoirs include an oxidizing agent, and second reservoir surfaces of selected ones of the multiple second reservoirs are proximate to the first substrate surface.

10 Claims, 29 Drawing Sheets

Related U.S. Application Data filed on Mar. 12, 2020, provisional application No. 63/012,370, filed on Apr. 20, 2020.

(56) References Cited

U.S. PATENT DOCUMENTS

| | | | |
|---|---|---|---|
| 11,253,015 B2* | 2/2022 | Nagel | A41D 13/11 |
| 2008/0295843 A1* | 12/2008 | Haas | A41D 13/1192 |
| | | | 128/206.28 |
| 2014/0364819 A1* | 12/2014 | VanDelden | A61F 13/00991 |
| | | | 604/290 |
| 2018/0355525 A1* | 12/2018 | Ando | A41D 31/30 |
| 2021/0282479 A1* | 9/2021 | Nagel | A61L 9/16 |

* cited by examiner

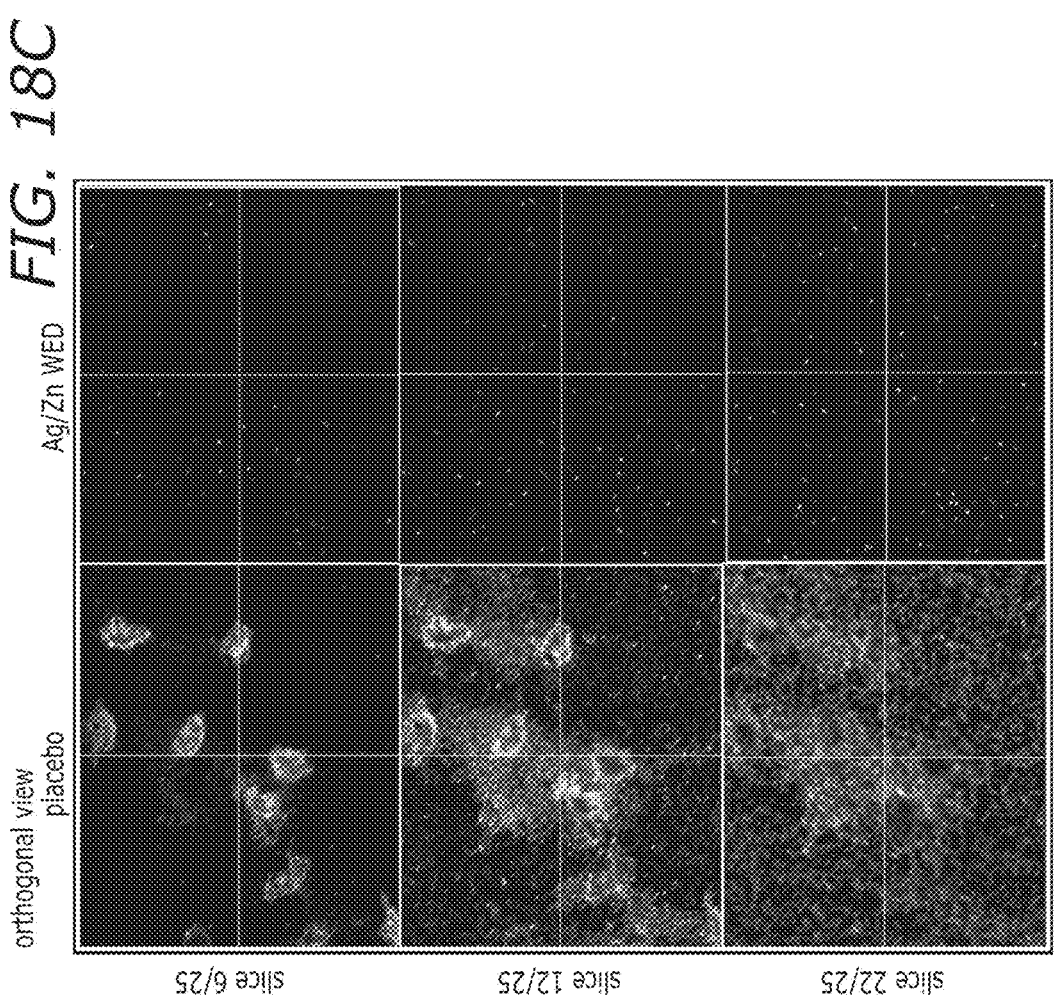
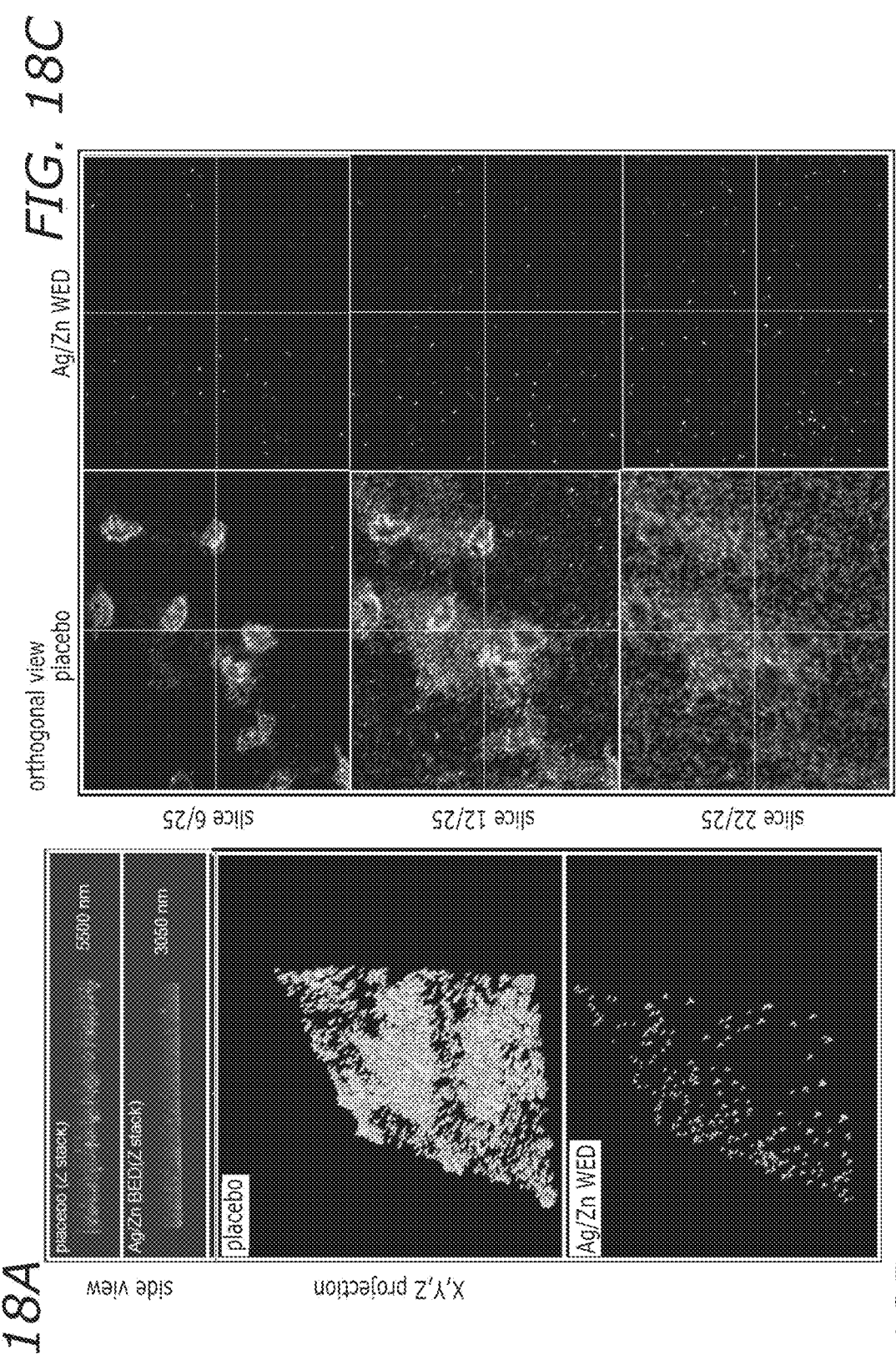
FIG. 18A  FIG. 18B  FIG. 18C

T30_Blank
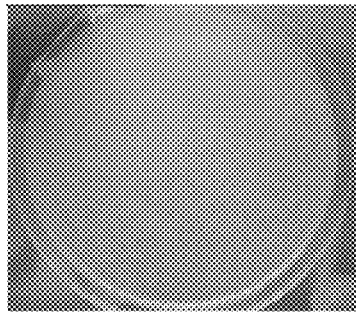
FIG. 27A
T30_Zinc 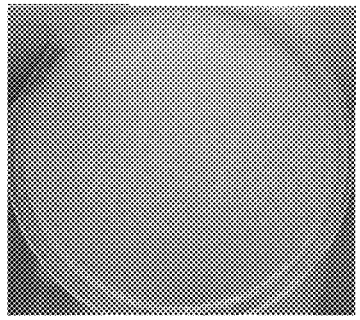 T30_Silver 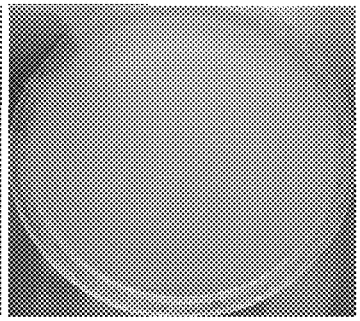 T30 Procellera 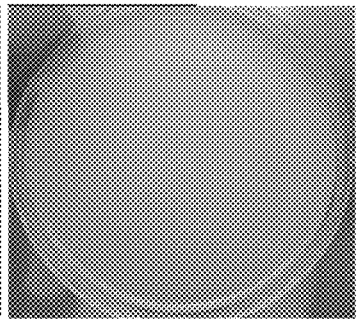
FIG. 27B  FIG. 27C  FIG. 27D
T60_Blank
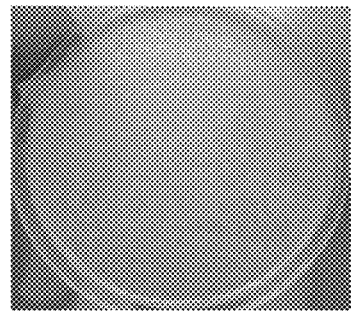
FIG. 28A
T60_Zinc 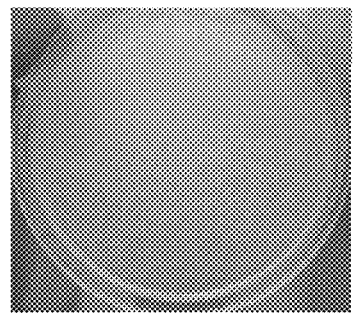 T60_Silver 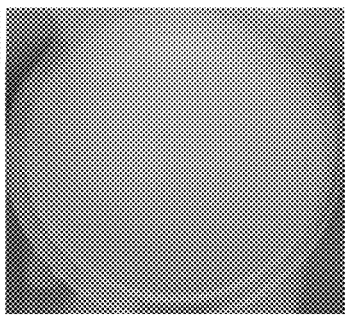 T60 Procellera 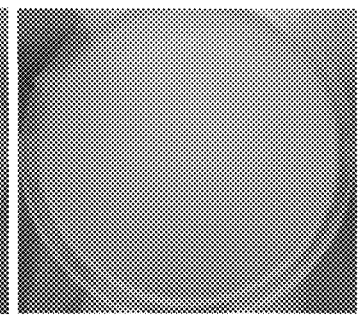
FIG. 28B  FIG. 28C  FIG. 28D

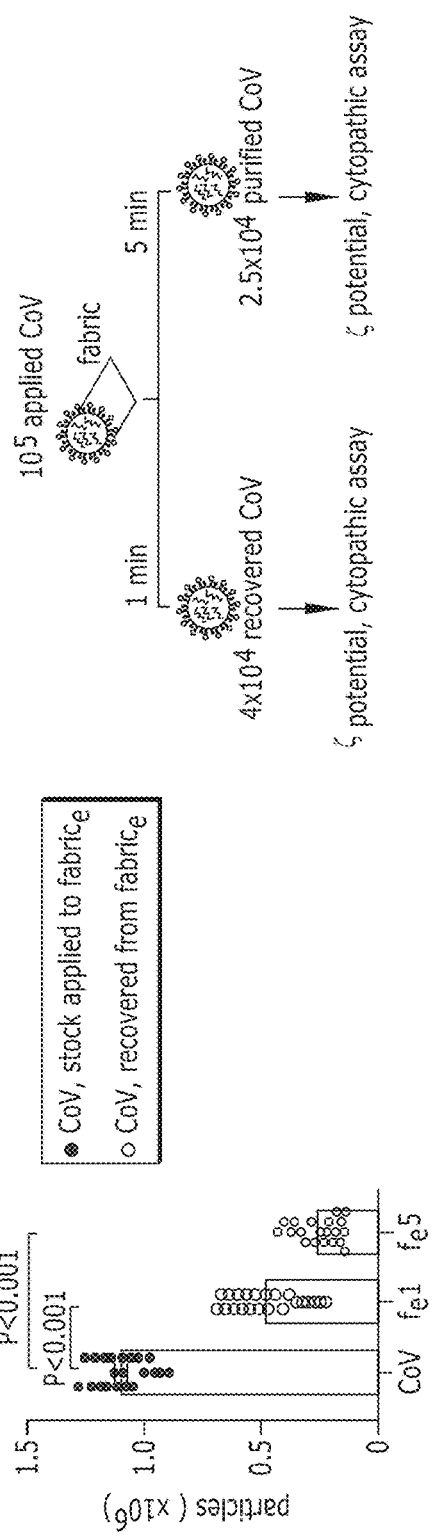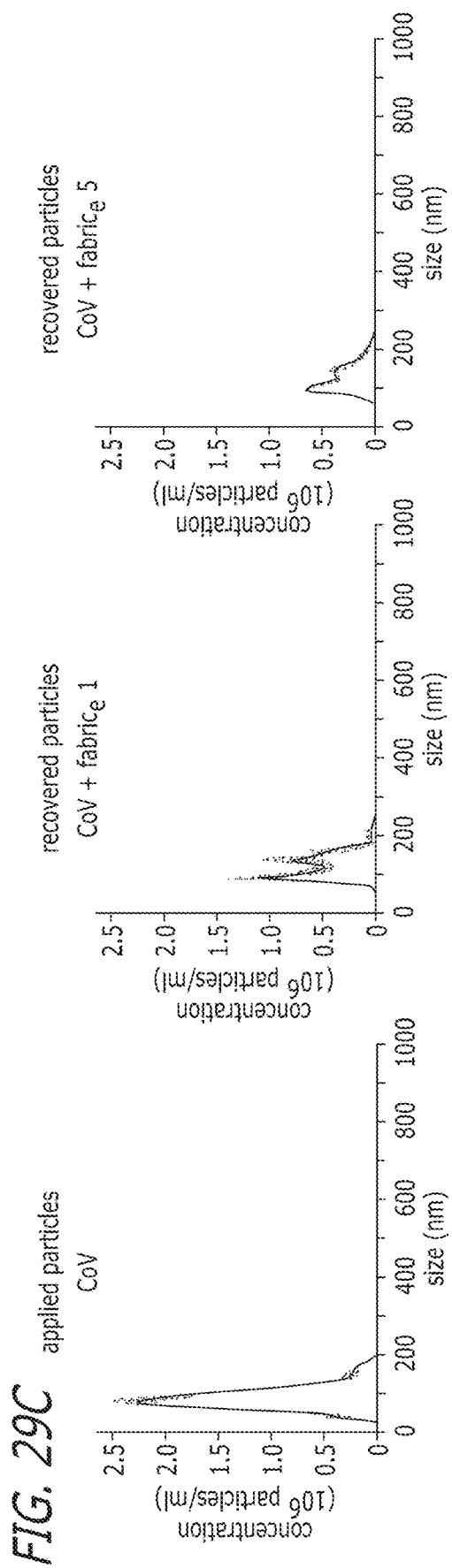

FIG. 30C  CoV recovered from fabric$_S$ + ST cells phase — Calcein AM — PI — merged (1 min / 5 min rows)

FIG. 30D  CoV recovered from fabric$_S$ + ST cells phase — Calcein AM — PI — merged (1 min / 5 min rows)

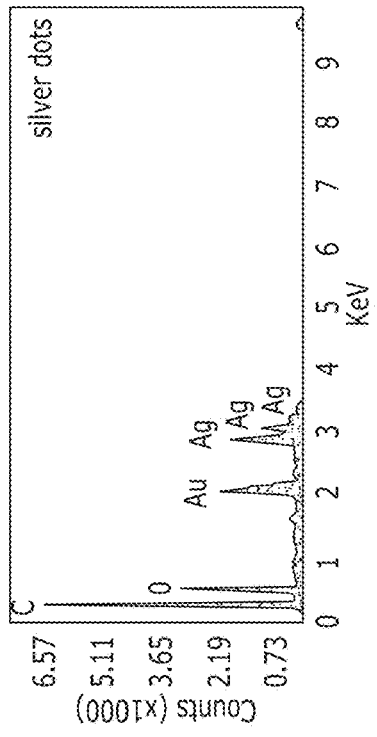
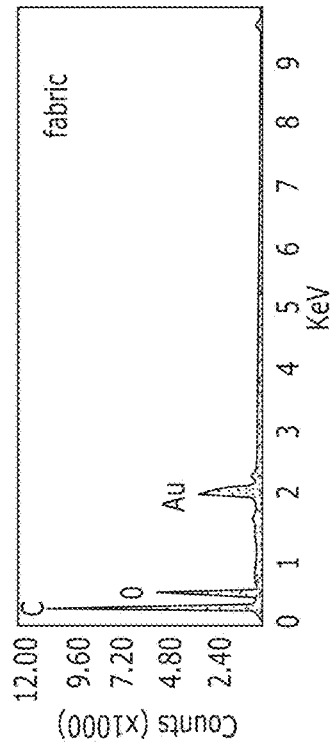
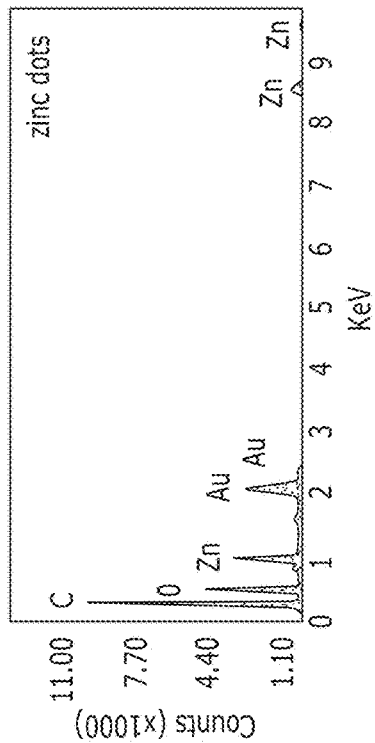
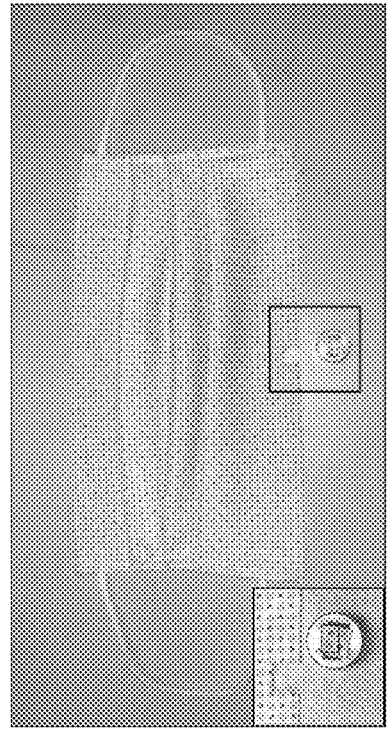
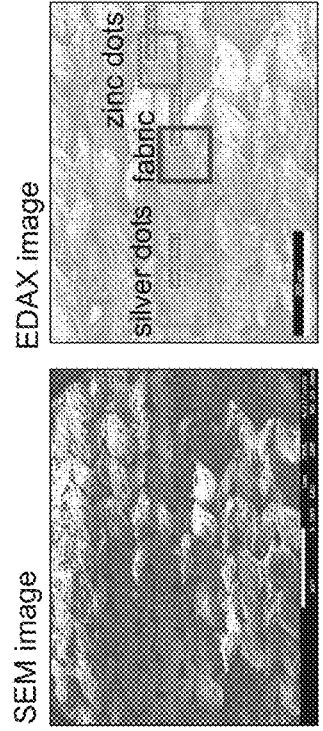
FIG. 32A
FIG. 32B
FIG. 32C

FIG. 33

METHODS AND DEVICES FOR PREVENTING VIRAL TRANSMISSION

CROSS-REFERENCE TO RELATED APPLICATIONS

This application claims priority under 35 U.S.C. § 119(e) to U.S. Provisional Application Ser. No. 62/987,786 filed Mar. 10, 2020; 62/988,739 filed Mar. 12, 2020; and 63/012,370 filed Apr. 20, 2020. The entire contents of each of these applications are incorporated by reference herein.

FIELD

Living organisms are affected by electrical stimulus. Accordingly, apparatus and techniques for applying electric stimulus to tissue have been developed to address a number of medical issues. The present Specification relates to methods and devices useful for preventing viral transmission and infection.

BACKGROUND

An infectious organism can use a person's body to sustain itself, reproduce, and colonize. These infectious organisms are known as pathogens. Examples of pathogens include bacteria, viruses, fungi, and prions. Pathogens can multiply and adapt quickly. Some infections are mild and barely noticeable, but others are severe and life-threatening, and some are resistant to treatment. Infection can be transmitted in a variety of ways. These include skin contact, bodily fluids, contact with feces, airborne particles, and touching an object that an infected person has also touched. How an infection spreads and its effect on the human body depend on the type of agent. The immune system is an effective barrier against infectious agents, but colonies of pathogens may grow too large for the immune system to fight. At this stage, infections can become harmful. Due to the severity of viral infections, preventing transmission of a virus can be a critical step in avoiding infection. However, current filtration capabilities limit the antiviral protection that masks can provide.

SUMMARY

Aspects disclosed herein include systems, devices, and methods for preventing viral transmission, for example using bioelectric devices that comprise a multi-array matrix of biocompatible microcells in the form of a mask, such as a medical mask, a surgical mask, a respirator, or an insert shaped to fit within or without a mask or respirator, for example as a layer in a laminate construction, in a filter port, or affixed to the mask or respirator. Embodiments comprise substrates comprising a multi-array matrix of biocompatible microcells that can be inserted into a port or slot, or affixed to a surgical mask, for example the interior (facing the user) side of a surgical mask, the exterior side, or both, thereby providing antiviral properties to a mask.

Aspects disclosed herein comprise bioelectric devices comprising a multi-array matrix of biocompatible microcells. Such matrices can include a first array comprising a pattern of microcells, for example formed from a first conductive solution, the solution including a metal species; and a second array comprising a pattern of microcells, for example formed from a second conductive solution, the solution including a metal species capable of defining at least one voltaic cell for spontaneously generating at least one electrical current with the metal species of the first array when said first and second arrays are introduced to an electrolytic solution such as saline, and said first and second arrays are not in physical contact with each other. Certain aspects utilize an external power source such as AC or DC power or pulsed RF or pulsed current, such as high voltage pulsed current. In one embodiment, the electrical energy is derived from the dissimilar metals creating a battery at each cell/cell interface, whereas those embodiments with an external power source may employ conductive electrodes in a spaced apart configuration to predetermine the electric field shape and strength. The external source can provide energy for a longer period than the batteries on the surface.

h. EDS element map of carbon. Scale bar A-B, E-H: 1 mm; C-D: 250 μm

14(B, C) Absorbance measurement on treating planktonic PAO1 culture with placebo, Ag/Zn BED and placebo+Ag dressing; and CFU measurement.

14(D) Zone of inhibition with placebo, Ag/Zn BED and placebo+Ag dressing.

Figure 15:
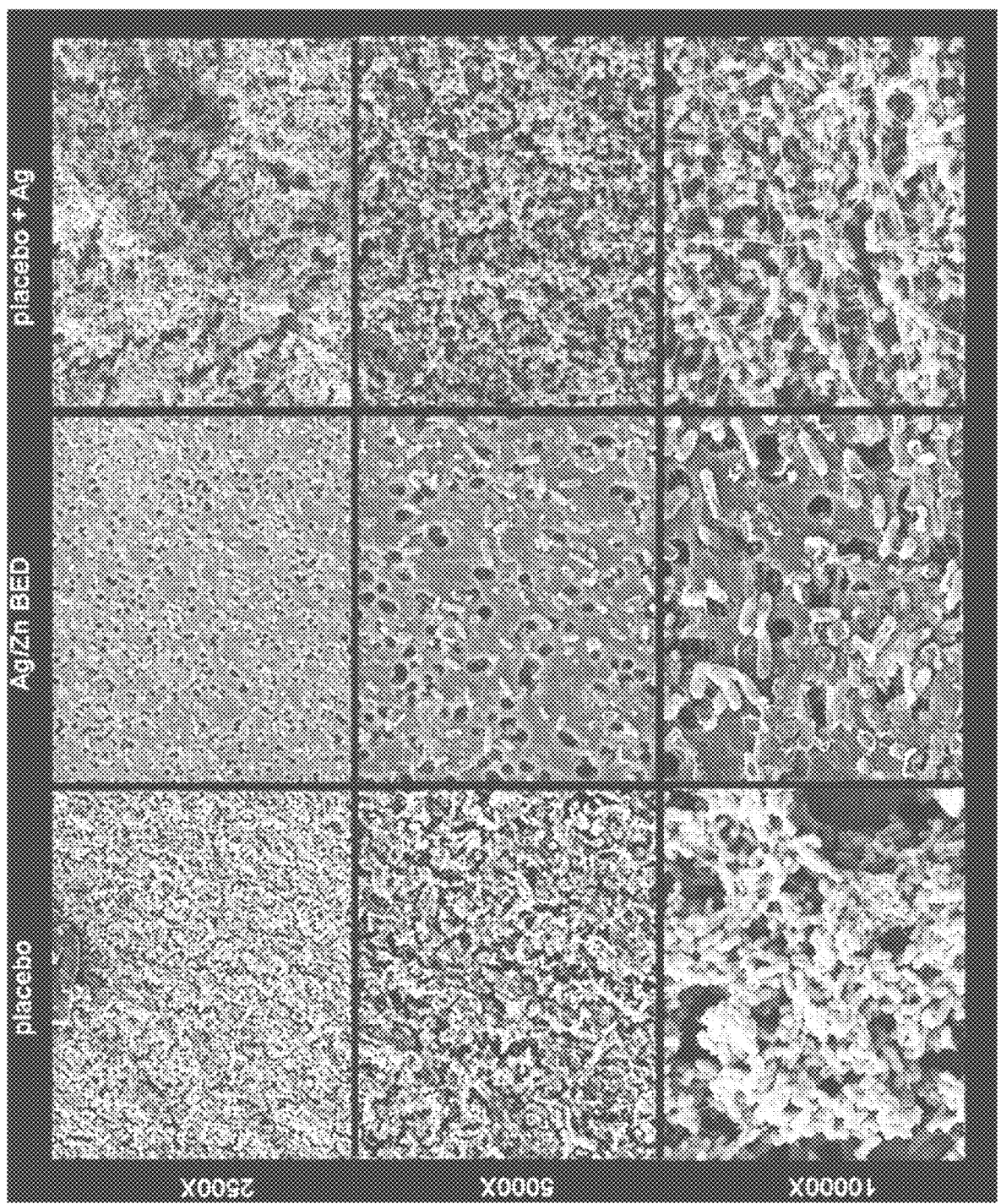

FIG. 15 depicts Scanning Electron Microscope (SEM) images of in-vitro *Pseudomonas aeruginosa* PAO1 biofilm treated with placebo, an embodiment disclosed herein ("BED"), and placebo+Ag dressing. The BED treated biofilm shows a dramatic decrease in bacteria number.

Figure 16:
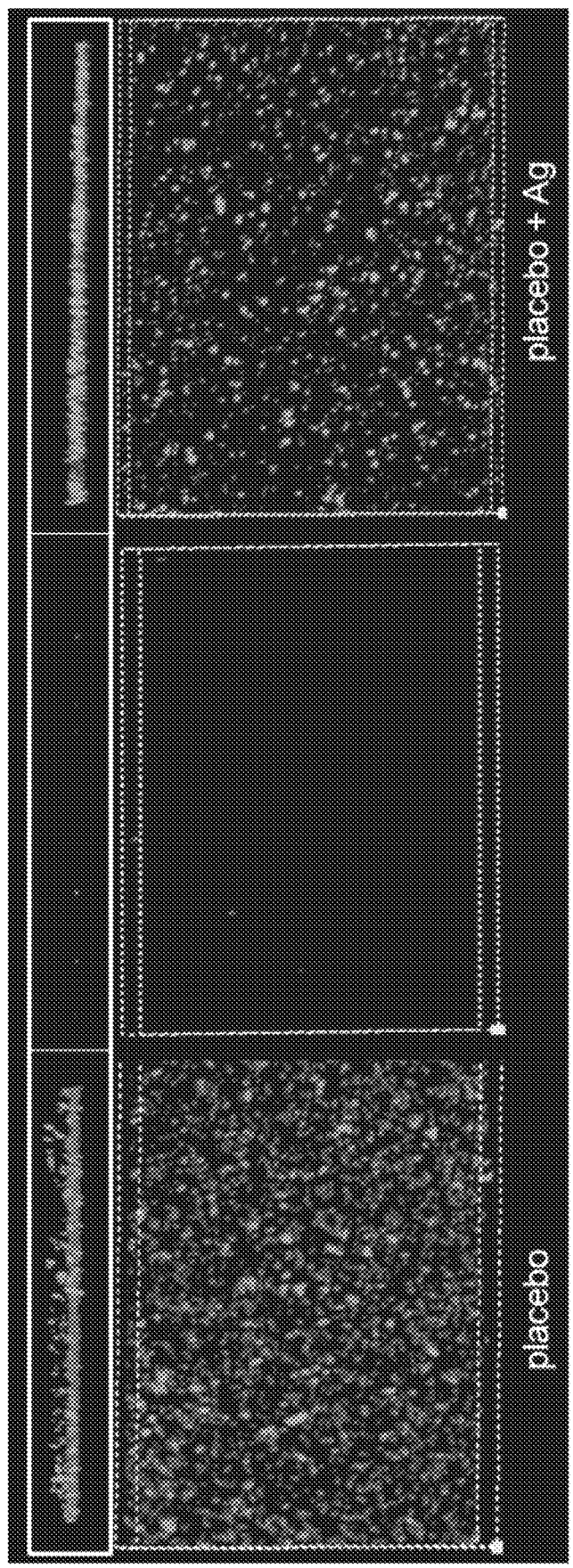

FIG. 16 shows extracellular polysaccharide staining (EPS).

Figure 17:
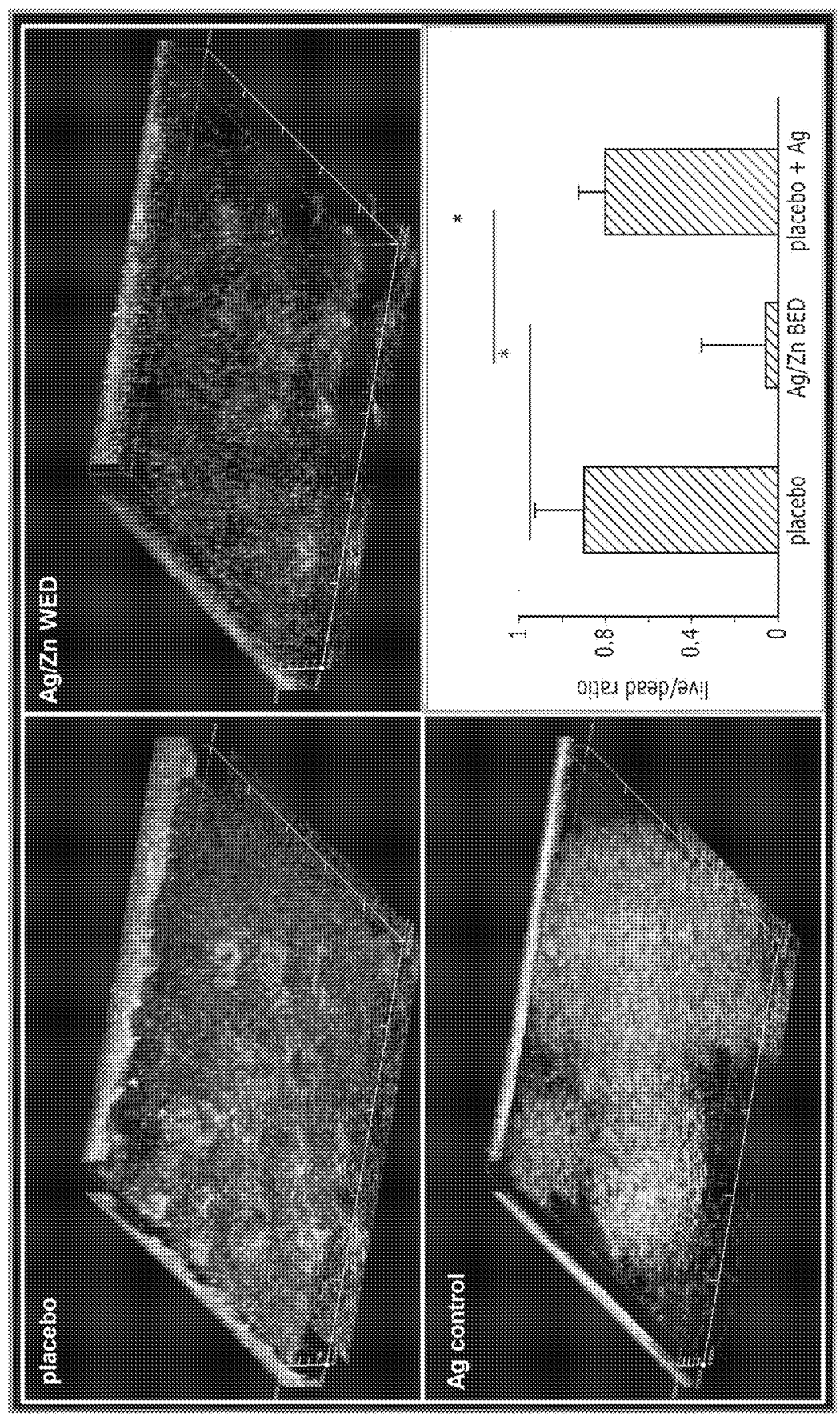

FIG. 17 shows live/dead staining. The green fluorescence indicates live PAO1 bacteria while the red fluorescence indicates dead bacteria.

FIG. 18 shows PAO1 staining.

Figure 19:
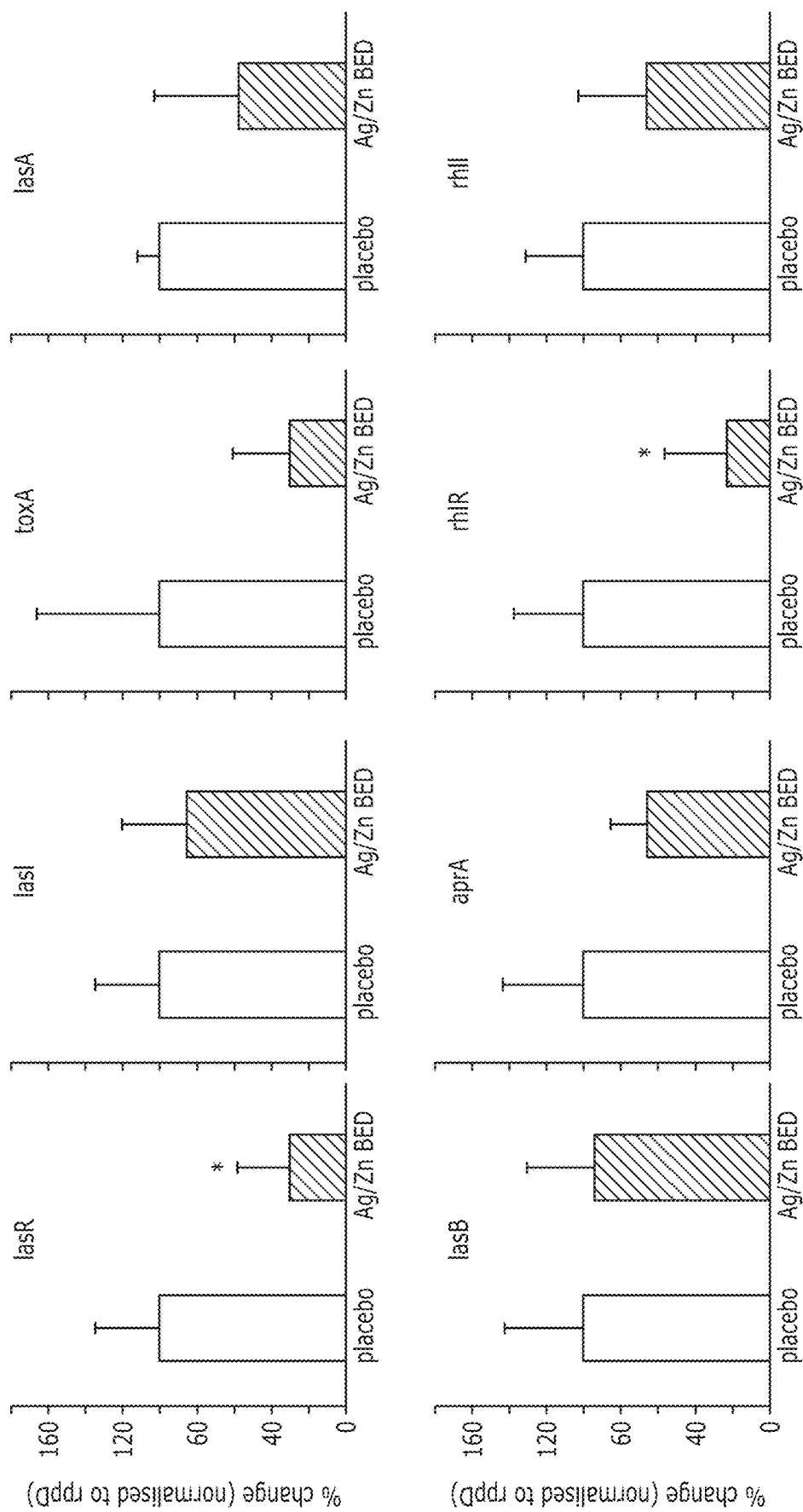

FIG. 19 depicts real-time PCR to assess quorum sensing gene expression.

Figures 20A, 20B:
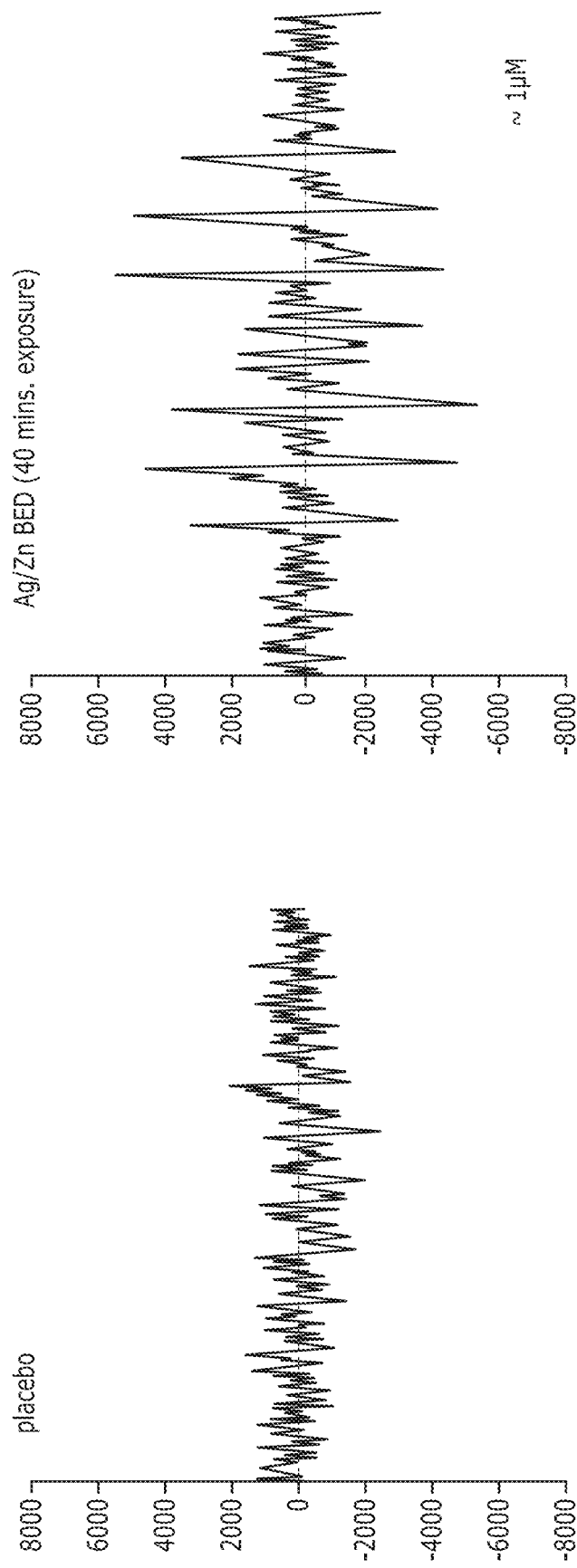

FIG. 20 shows electron paramagnetic (EPR) spectra using DEPMPO (a phosphorylated derivative of the widely used DMPO spin trap). Spin adduct generation upon exposure to disclosed embodiments for 40 minutes in PBS.

Figure 21:
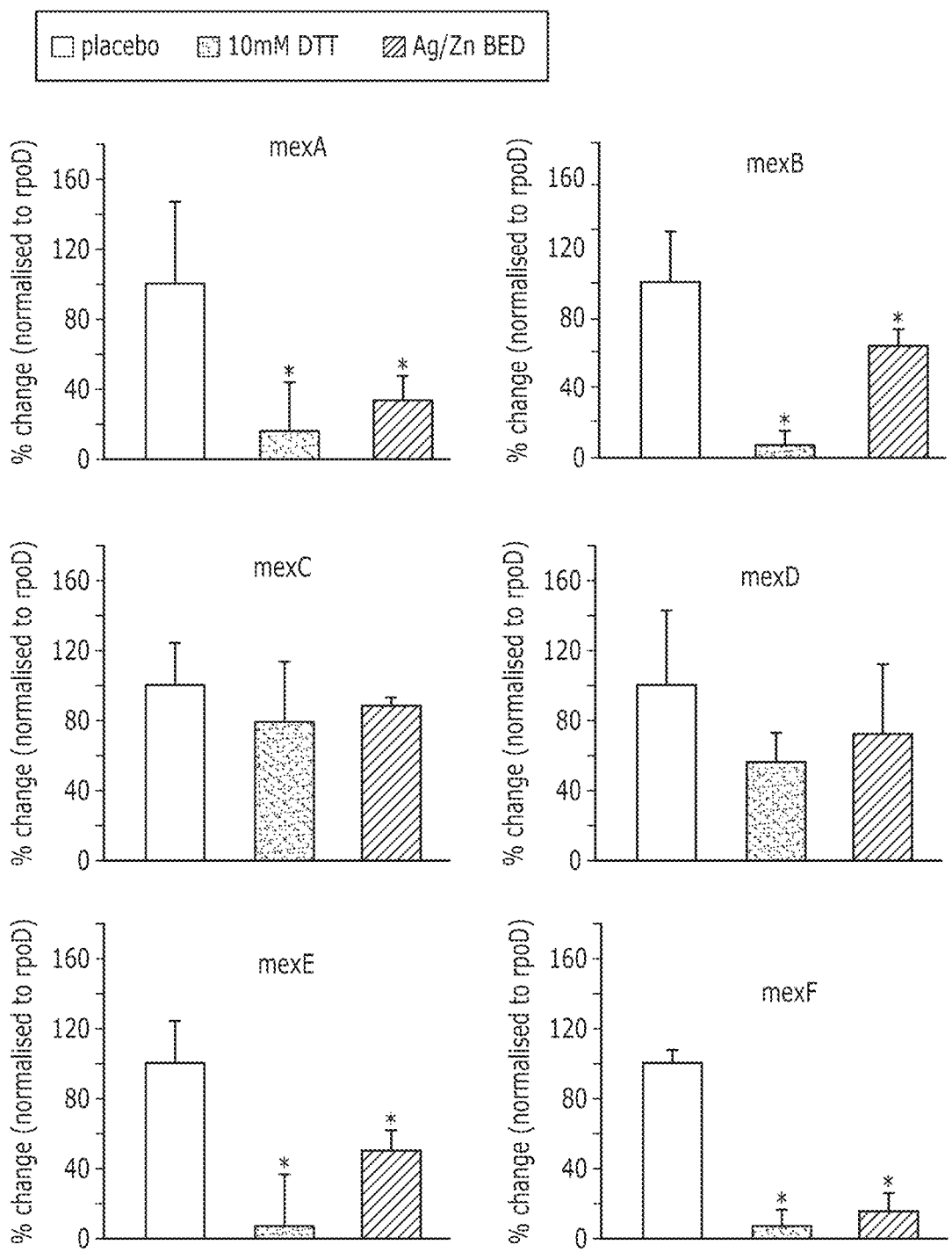

FIG. 21 depicts real-time PCR performed to assess mex gene expression upon treatment with Ag/Zn BED and 10 mM DTT.

Figure 22A:
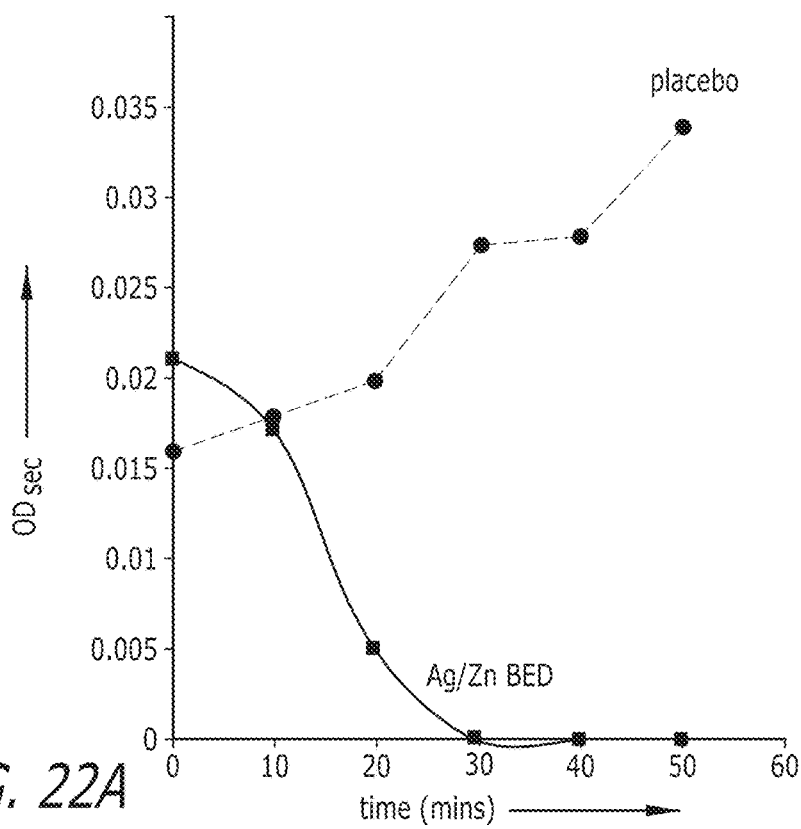
Figure 22B:
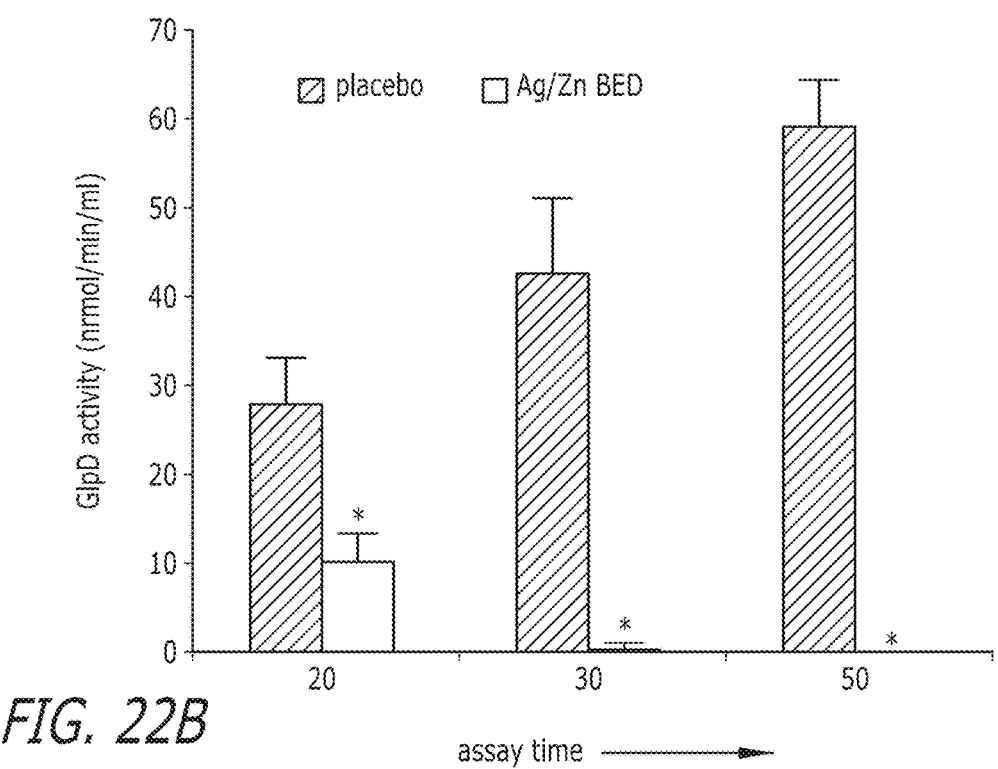

FIG. 22 shows Glycerol-3-Phosphate Dehydrogenase (GPDH) enzyme activity.
  a. OD was measured in the kinetic mode.
  b. GPDH activity was calculated using the formula, Glycerol-3-Phosphate dehydrogenase activity=B/($\Delta T \times$ V)×Dilution Factor=nmol/min/ml, where: B=NADH amount from Standard Curve (nmol). $\Delta T$=reaction time (min). V=sample volume added into the reaction well (ml).

Figure 23:
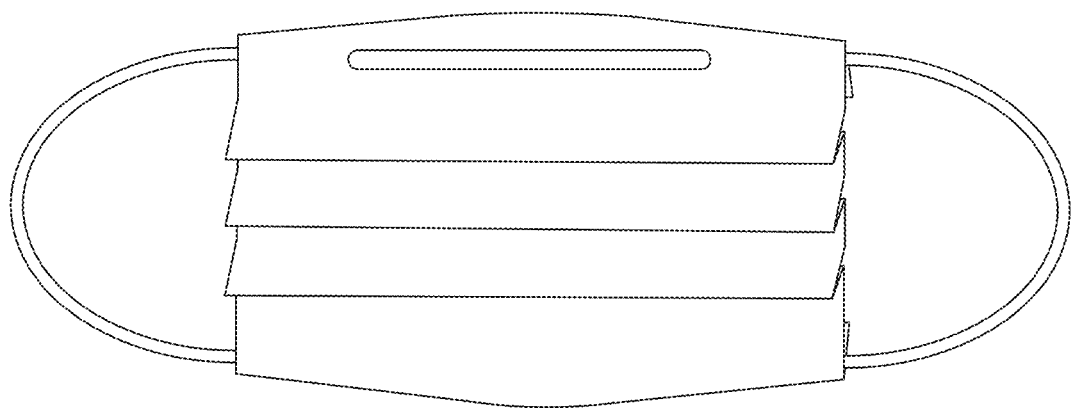

FIG. 23 depicts a mask embodiment comprising pleats and a bendable portion atop the mask to allow the user to better conform the mask to her face.

Figure 24:
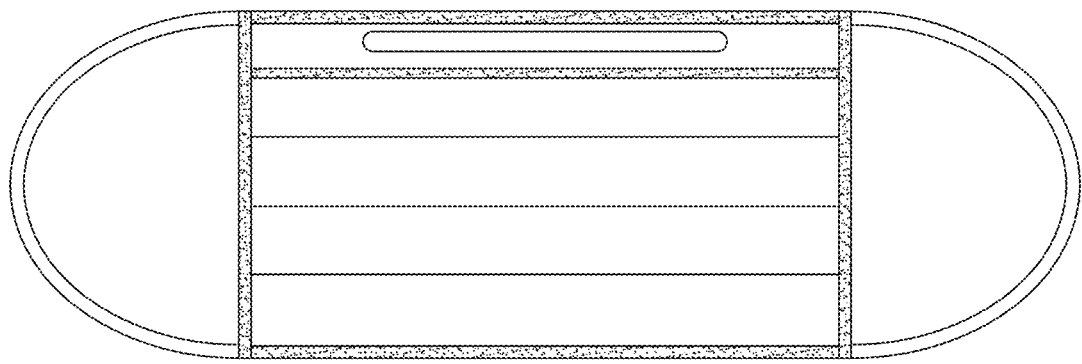

FIG. 24 depicts a mask embodiment comprising pleats and a bendable portion atop the mask to allow the user to better conform the mask to her face.

Figure 25:
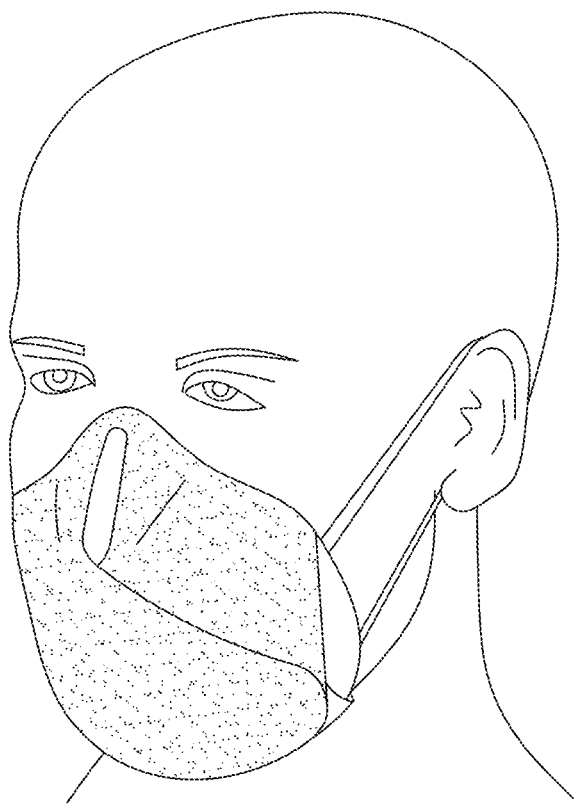

FIG. 25 depicts a mask embodiment comprising a "snap" closure.

Figure 26:
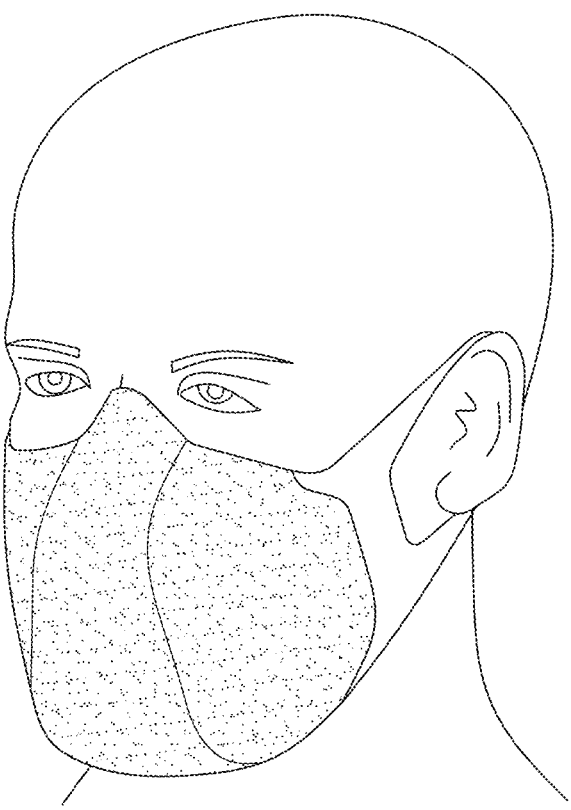

FIG. 26 depicts a mask embodiment.

FIG. 27 shows the antiviral effect of a disclosed embodiment as described in Example 16.

FIG. 28 shows the antiviral effect of a disclosed embodiment as described in Example 16.

Figure 29F:
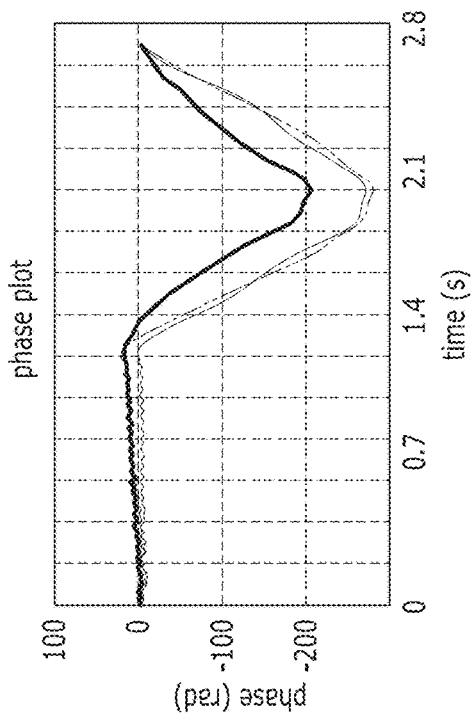
Figure 29E:
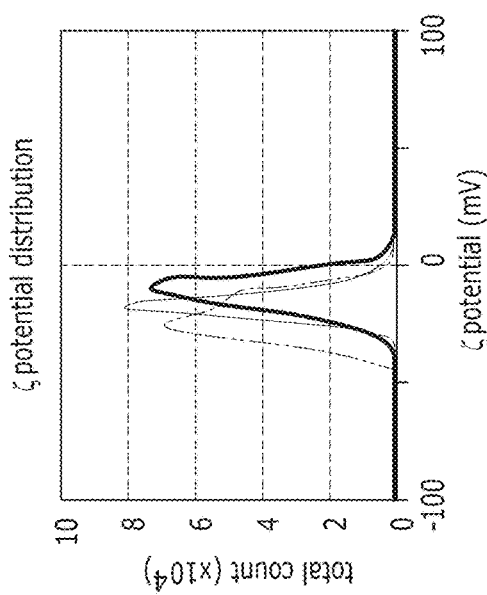
Figure 29D:
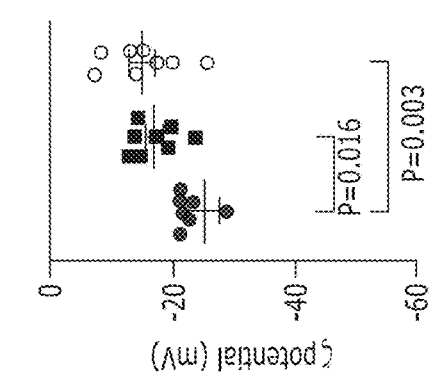

FIG. 29 depicts quantification of the purified viral particles after spotting on fe (an embodiment disclosed herein) yielded 44.29% and 23.73% recovery from the fabric when exposed for 1 min or 5 min, respectively (FIG. 29A). Nanoparticle tracking analysis demonstrated that unlike the purified CoV that showed a single peak around 75 nm, the recovered CoV showed additional peaks suggesting aggregation of the viral particles upon contact with the fabric (FIG. 29B). Analysis of zeta potential showed significant graded attenuation of this electrokinetic property upon contact with the fe (FIG. 29C). Such lowering of average zeta potential of CoV, applied and recovered from fe, has been plotted graphically (FIG. 29D). Unlike 1 min exposure to the fe, 5 min exposure showed an appreciable difference in the phase plot of the viral particles (FIG. 29E).

Figure 30A:
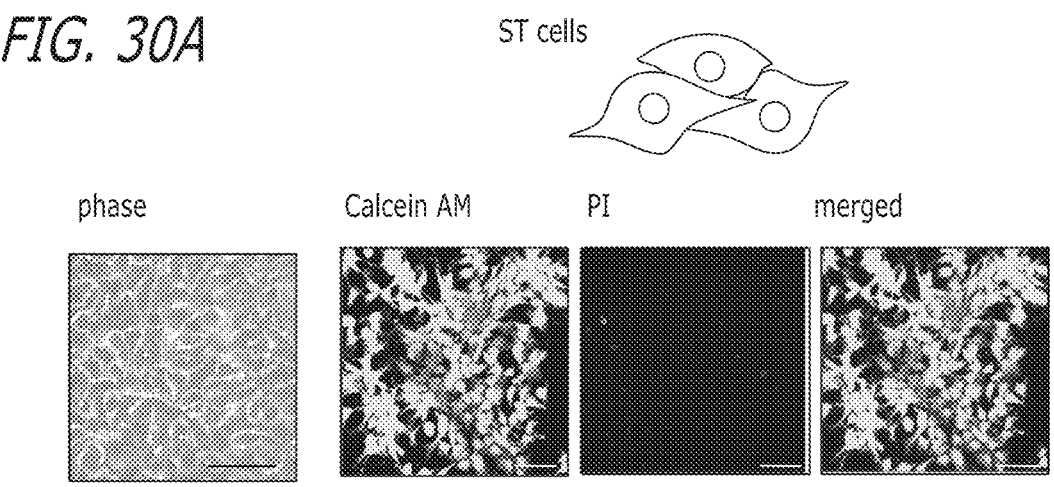
Figure 30B:
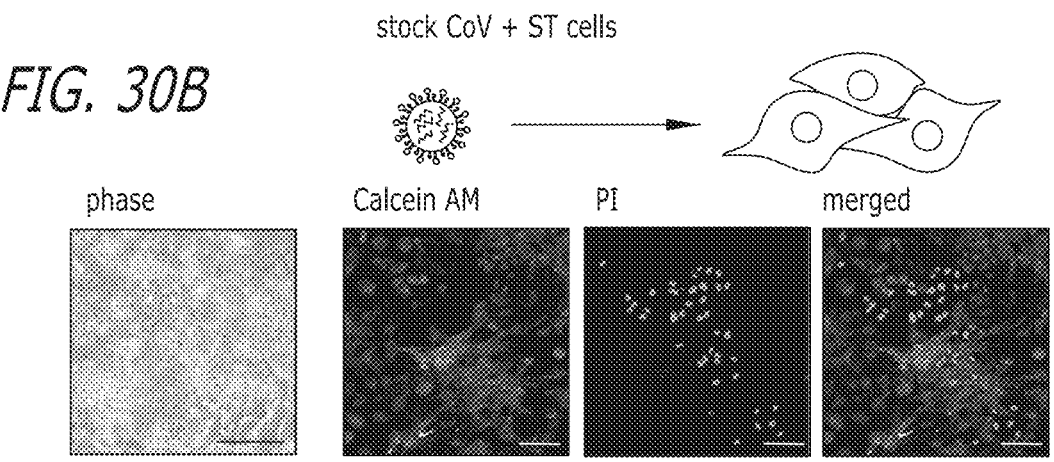
Figures 30E, 30F:
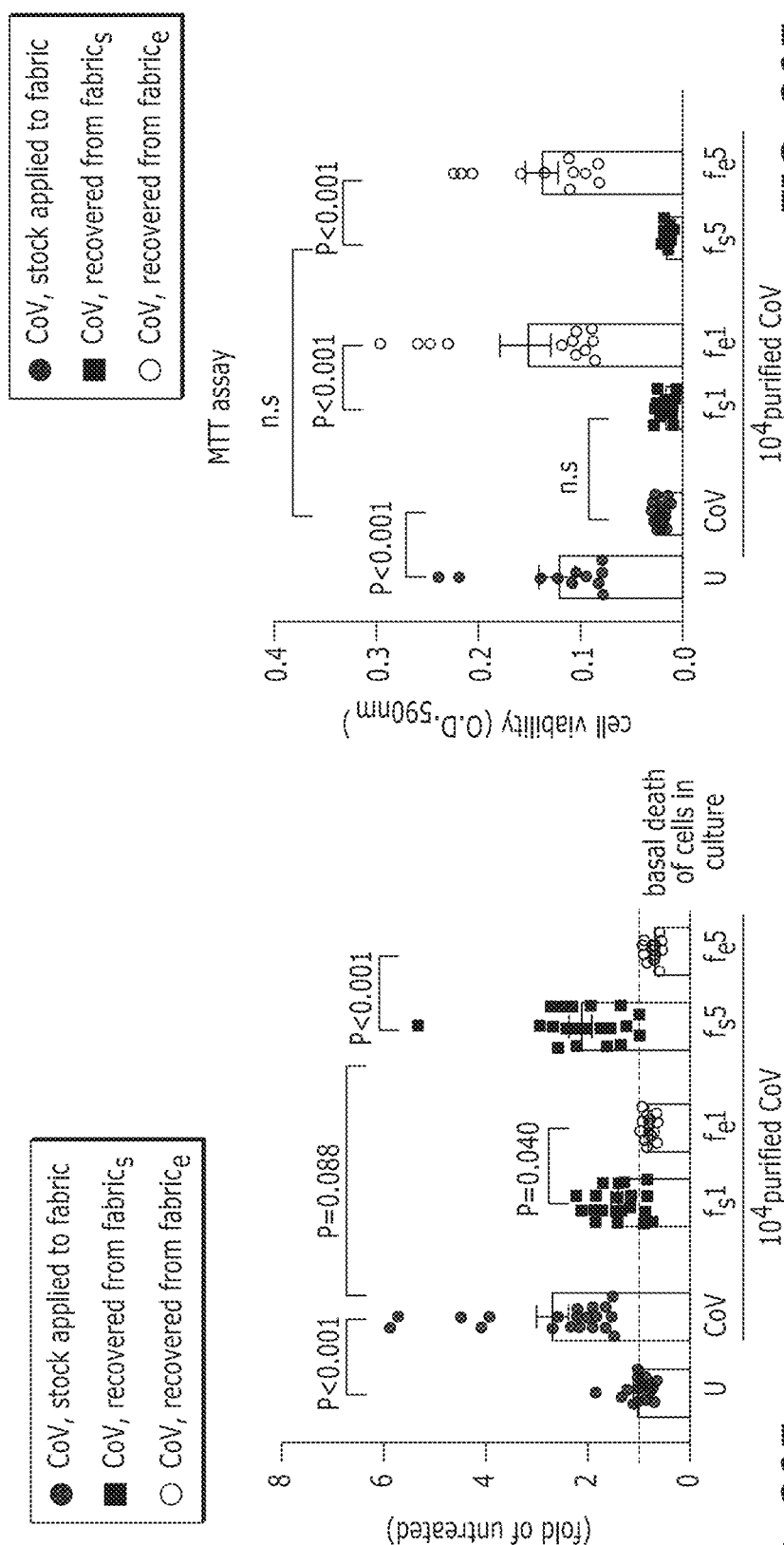

FIG. 30; To assess changes in the infectivity of CoV following contact with the electroceutical fabric, a cytopathic assay was employed. Infected cells were monitored for appearance of cytopathic effects (CPE; cell rounding and sloughing) until post-infection day 7. Overt CPE was observed on day 7 in response to CoV infection (FIG. 30B). Comparable CPE was noted in response to treatment of cells with CoV recovered from sham control fabric fs (FIG. 30C). In contrast, CoV recovered from fe did not cause any CPE indicating loss of its infectivity (FIG. 30D). Cells treated with fe-recovered CoV particles appeared as healthy as the uninfected cells (FIG. 30A). Objective assessment of cell viability was performed using a calcein/PI fluorescence assay. Only live cells with intracellular esterase activity hydrolyze the acetoxymethyl ester in non-fluorescent Calcein AM converting it into green fluorescent Calcein. Dead cells or cells with damaged or compromised cell membranes include PI stain, which is otherwise impermeant to live cells. Fold-change increase in PI/Calcein signal as shown indicates loss of cell viability in response to infection. Infection of cells with CoV caused marked loss of cell viability (FIG. 30B). Such cytopathic effect of CoV was completely absent once the virus was exposed to fe (FIG. 30 D-E). The sham fabric did not afford such protection (FIG. 30C,E). The cytopathic effects of CoV and the protective effects of fe (versus fs) was corroborated by the standard MTT assay commonly used for testing cell viability (FIG. 30F).

Figure 31A:
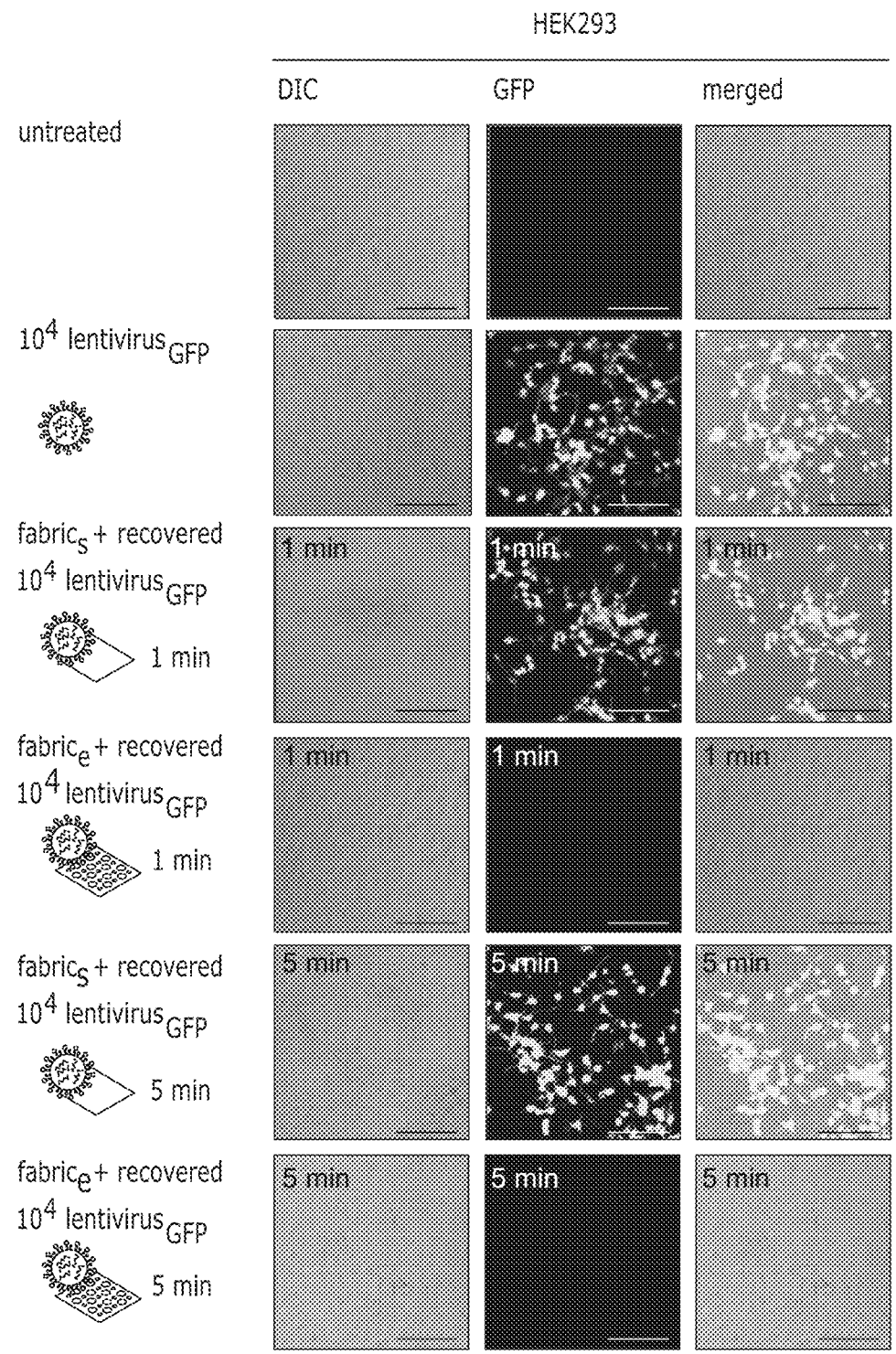
Figure 31B:
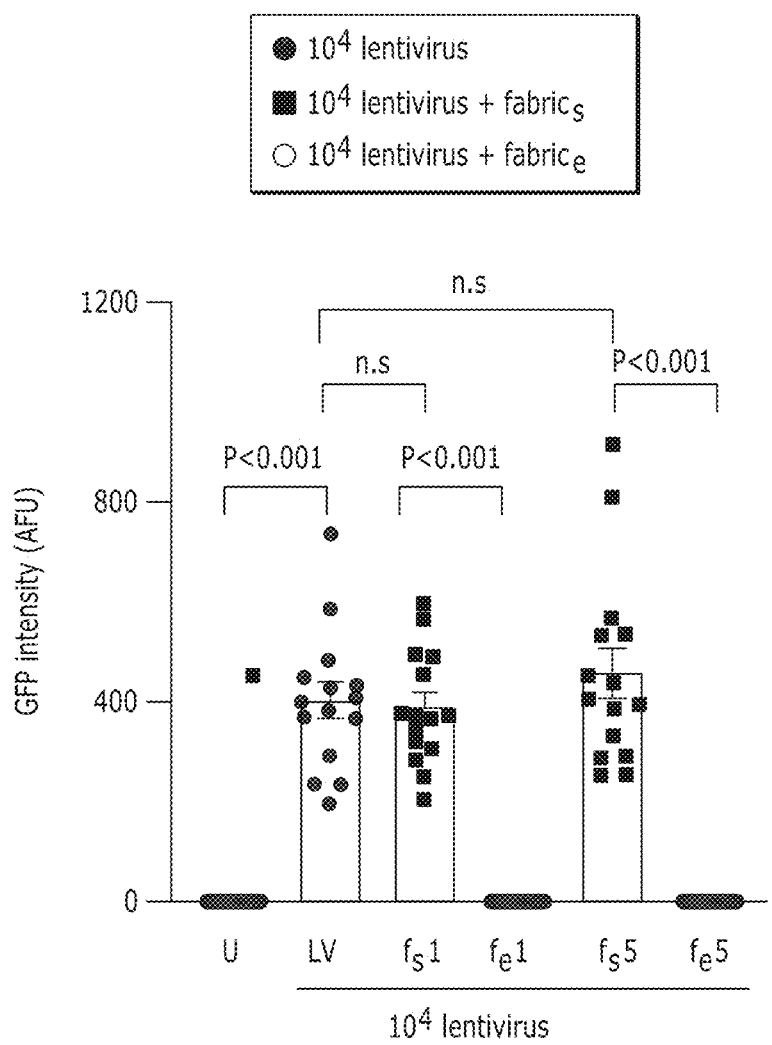

FIGS. 31A and 31B; The Lentiviral pseudotype system is a standard laboratory tool to study the infectivity of viruses under conventional biosafety conditions. Lentivirus CSCGW mut6, upon successful transduction in HEK293 cells, results in GFP-expressing host cells. This expression is a direct measure of lentiviral replication competency and ability of the virus to integrate in the host genome. The ability of the electroceutical fabric to influence the infectivity of a virus, other than CoV, was tested to appreciate its broader significance of scope. Mammalian cells were treated with purified lentivirus or the same virus subjected to contact with fe or fs for 1 or 5 mins as indicated in the figure legend (FIG. 31A). Transduced cells were monitored microscopically to check the presence of GFP+ cells, a marker of successful infection. Lentiviral exposure caused widespread infection of cells. Treatment of cells with virus recovered from sham fabric fs caused comparable infection (FIG. 31B). However, contact of virus with the electroceutical fabric fe, even for one minute, eliminated lentiviral infectivity (FIG. 31B).

FIG. 32 shows SEM of the fabric used for a disclosed mask showed a different weaving pattern aimed at higher stretch property (FIG. 32A-C). Deposition of Ag and Zn on the fabric for face-mask was tested by EDX spectrum analysis (FIG. 32B).

Figure 33:
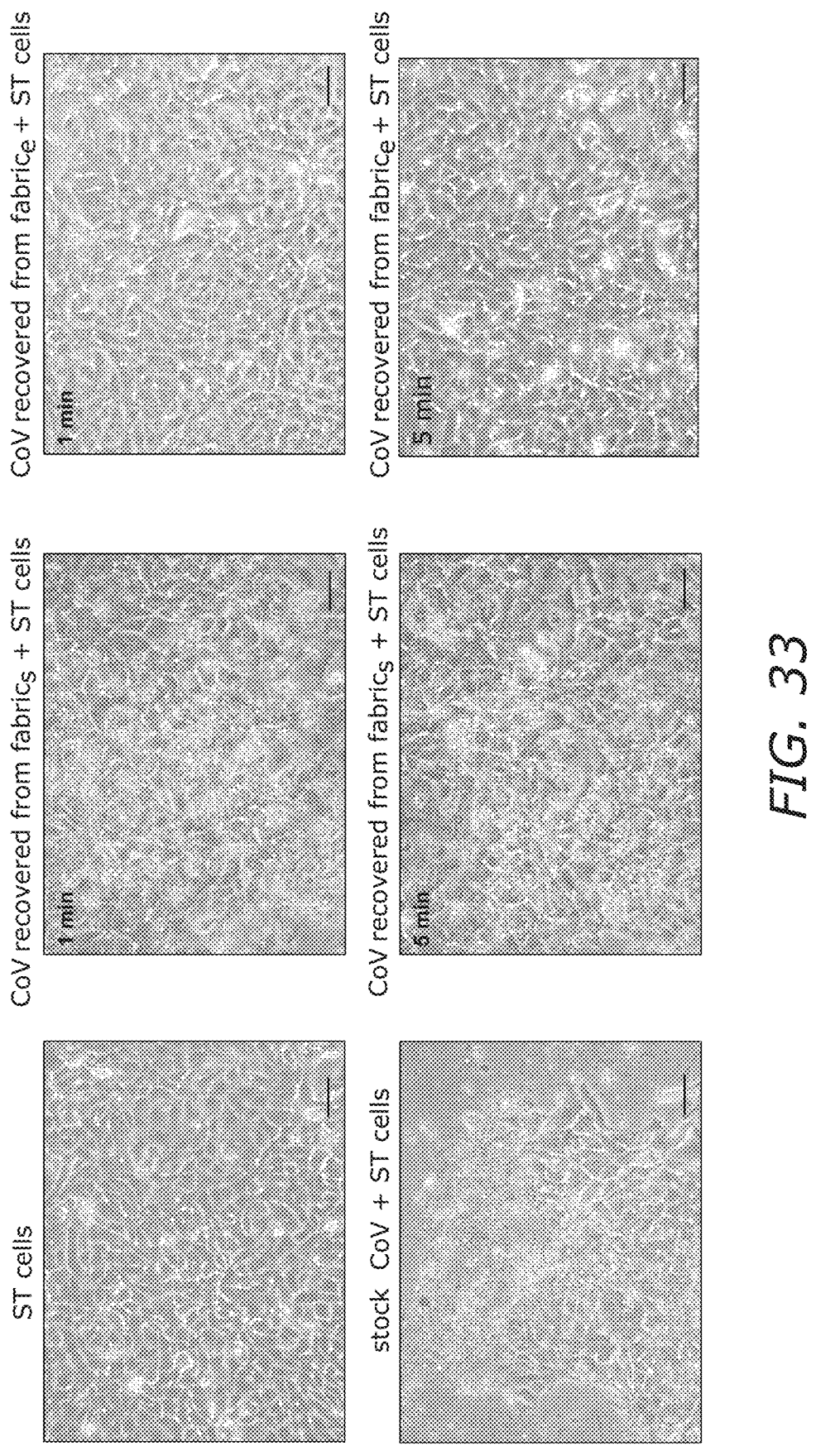

FIG. 33; To assess changes in the infectivity of CoV following contact with the electroceutical fabric, a cytopathic assay was employed. Infected cells were monitored for appearance of cytopathic effects (CPE; cell rounding and sloughing) until post-infection day 7. Overt CPE was observed on day 7 in response to CoV infection. Comparable CPE was noted in response to treatment of cells with CoV recovered from sham control fabric fs. In contrast, CoV recovered from fe did not cause any CPE indicating loss of its infectivity. Cells treated with fe-recovered CoV particles appeared as healthy as the uninfected cells. Objective assessment of cell viability was performed using a calcein/PI fluorescence assay. Only live cells with intracellular esterase activity hydrolyze the acetoxymethyl ester in non-fluorescent Calcein AM converting it into green fluorescent Calcein. Dead cells or cells with damaged or compromised cell membranes include PI stain, which is otherwise impermeant to live cells. Fold-change increase in PI/Calcein signal as shown indicates loss of cell viability in response to infection. Infection of cells with CoV caused marked loss of cell viability. Such cytopathic effect of CoV was completely absent once the virus was exposed to fe. The sham fabric did not afford such protection. The cytopathic effects of CoV and the protective effects of fe (versus fs) was corroborated by the standard MTT assay commonly used for testing cell viability.

DETAILED DESCRIPTION

Embodiments disclosed herein include systems that can provide a low level electric field (LLEF) to a location, tissue or organism (an "LLEF system") or, when brought into contact with an electrically conducting material, can provide a low level electric current (LLEC) to a location, tissue or organism (an "LLEC system"). Thus, in embodiments an LLEC system is an LLEF system that is in contact with an electrically conducting material. In certain embodiments, the electric current or electric field can be modulated, for example, to alter the duration, size, shape, field depth, duration, current, polarity, or voltage of the system. In embodiments the watt-density of the system can be modulated.

"Activation gel" or "activation liquid" as used herein means a composition useful for maintaining a moist environment within and about the device. Activation gels can be conductive. In embodiments, the water vapor in a user's breath can act as an activation gel or liquid. Saline can act as an activation gel or liquid.

"Affixing" as used herein can mean contacting a device, patient or tissue with a device or system disclosed herein. In embodiments "affixing" can include the use of straps, elastic, etc., to join (reversibly or non-) the embodiment to a mask or respirator, or to a "port" or receiving portion of the mask or respirator.

"Applied" or "apply" as used herein refers to contacting a surface with a conductive material, for example printing, painting, or spraying a conductive ink on a surface. Alternatively, "applying" can mean contacting a patient or tissue or organism with a device or system disclosed herein.

"Conductive material" as used herein refers to an object or type of material which permits the flow of electric charges in one or more directions. Conductive materials can include solids such as metals or carbon, or liquids such as conductive metal solutions and conductive gels. Conductive materials can be applied to form at least one matrix. Conductive liquids can dry, cure, or harden after application to form a solid material.

"Discontinuous region" as used herein refers to a "void" in a material such as a hole, slit, slot, or the like. The term can mean any void in the material though typically the void is of a regular shape. A void in the material can be entirely within the perimeter of a material or it can extend to the perimeter of a material.

"Dots" as used herein refers to discrete deposits of dissimilar reservoirs that can function as at least one battery cell. The term can refer to a deposit of any suitable size or shape, such as squares, circles, triangles, lines, etc. The term can be used synonymously with microcells, etc.

"Electrode" refers to similar or dissimilar conductive materials. In embodiments utilizing an external power source the electrodes can comprise similar conductive materials. In embodiments that do not use an external power source, the electrodes can comprise dissimilar conductive materials that can define an anode and a cathode.

"Expandable" as used herein refers to the ability to stretch while retaining structural integrity and not tearing. The term can refer to solid regions as well as discontinuous or void regions; solid regions as well as void regions can stretch or expand.

"Insert" (used as a noun) or "mask insert" refers to a disclosed embodiment that is designed to form, fit inside or fit around a surgical mask. The insert can comprise adhesive or other means for securing it to a surgical mask. For example, adhesive "flaps" can be employed to affix the mask or insert.

"Matrix" or "matrices" as used herein refer to a pattern or patterns, such as those formed by electrodes on a surface, such as a fabric or a fiber, or the like. Matrices can be designed to vary the electric field or electric current or microcurrent generated. For example, the strength and shape of the field or current or microcurrent can be altered, or the matrices can be designed to produce an electric field(s) or current or microcurrent of a desired strength or shape.

"Stretchable" as used herein refers to the ability of embodiments that stretch without losing their structural integrity. That is, embodiments can stretch to accommodate irregular skin surfaces or surfaces wherein one portion of the surface can move relative to another portion.

"Viral transmission" refers to the transfer of a virus from one organism to another, for example via propagation of the virus from an infected organism or via acquisition of the virus by a healthy organism, or combinations thereof.

LLEC/LLEF Systems and Devices

In embodiments, systems and devices disclosed herein comprise patterned micro-batteries that create a unique field between each dot pair. In embodiments, the unique field is very short, i.e. in the range of the physiologic electric fields. In embodiments, the direction of the electric field produced by devices disclosed herein is similar to physiological conditions.

Embodiments disclosed herein can comprise patterns of microcells. The patterns can be designed to produce an electric field, an electric current, or both over and through tissue such as human skin. In embodiments the pattern can be designed to produce a specific size, strength, density, shape, or duration of electric field or electric current. In embodiments reservoir or dot size and separation can be altered.

In embodiments devices disclosed herein can apply an electric field, an electric current, or both, wherein the field, current, or both can be of varying size, strength, density, shape, or duration in different areas of the embodiment. In embodiments, by micro-sizing the electrodes or reservoirs, the shapes of the electric field, electric current, or both can be customized, increasing or decreasing very localized watt densities and allowing for the design of "smart patterned electrodes" where the amount of electric field over a tissue can be designed or produced or adjusted based on feedback from the tissue or on an algorithm within sensors operably connected to the embodiment and fed-back to a control module. The electric field, electric current, or both can be strong in one zone and weaker in another. The electric field, electric current, or both can change with time and be modulated based on treatment goals or feedback from the tissue or patient. The control module can monitor and adjust the size, strength, density, shape, or duration of electric field or electric current based on tissue parameters. For example, embodiments disclosed herein can produce and maintain very localized electrical events. For example, embodiments disclosed herein can produce specific values for the electric field duration, electric field size, electric field shape, field depth, current, polarity, and/or voltage of the device or system.

Devices disclosed herein can generate a localized electric field in a pattern determined by the size, distance between, and physical orientation of the cells or electrodes. Effective depth of the electric field can be predetermined by the orientation and distance between the cells or electrodes.

Embodiments of LLEC or LLEF systems disclosed herein can comprise electrodes or microcells. Each electrode or microcell can be or include a conductive metal. In embodiments, the electrodes or microcells can comprise any electrically-conductive material, for example, an electrically conductive hydrogel, metals, electrolytes, superconductors, semiconductors, plasmas, and nonmetallic conductors such as graphite and conductive polymers. Electrically conductive metals can include silver, copper, gold, aluminum, molybdenum, zinc, lithium, tungsten, brass, carbon, nickel, iron, palladium, platinum, tin, bronze, carbon steel, lead, titanium, stainless steel, mercury, Fe/Cr alloys, and the like. The electrode can be coated or plated with a different metal such as aluminum, gold, platinum or silver.

In certain embodiments, dot, reservoir, or electrode geometry can comprise circles, polygons, lines, zigzags, ovals, stars, or any suitable variety of shapes. This provides the ability to design/customize surface electric field shapes as well as depth of penetration. For example. In embodiments it can be desirable to employ an electric field of greater strength or depth in an area where skin is thicker.

Reservoir or dot sizes and concentrations can be of various sizes, as these variations can allow for changes in the properties of the electric field created by embodiments of the invention. Certain embodiments provide an electric field at about 1 Volt and then, under normal tissue loads with resistance of 100 k to 300K ohms, produce a current in the range of 1 to 10 microamperes.

A system disclosed herein and placed over tissue such as skin can move relative to the tissue. Reducing the amount of motion between tissue and device can be advantageous to skin treatment. Slotting or placing cuts into the device can result in less friction or tension on the skin. In embodiments, use of an elastic dressing similar to the elasticity of the skin is disclosed. In embodiments, disclosed devices comprise a slot from around the center of the device that runs to an outside edge, allowing the device to assume a "cone" shape that is appropriate for certain masks.

In embodiments the system comprises a component such as an adhesive or straps to maintain or help maintain its position. The adhesive component can be covered with a protective layer that is removed to expose the adhesive at the time of use. In embodiments the adhesive can comprise, for example, sealants, such as hypoallergenic sealants, gecko sealants, mussel sealants, waterproof sealants such as epoxies, and the like. Straps can include velcro or similar materials to aid in maintaining the position of the device. Straps can tie to other straps, for example encircling the head of a user. In embodiments, snaps can be used to secure the device, or to secure an overlapping portion of the device to maintain a desired shape, for example the shape of a mask or respirator as seen in FIG. 25. Disclosed masks can comprise loops, for example elastic loops, to secure the device against the user's face (FIG. 23, FIG. 24).

Masks can further a bendable aspect that can be bent, for example over the nose to provide a more secure fit (FIG. 24). This can also prevent or reduce fogging of glasses or goggles due to air flow escaping from the mask during an exhale. Disclosed masks can comprise pleats to increase surface area and improve flexibility (FIG. 23, FIG. 24). Disclosed masks can be contoured to better-fit a user's face.

In embodiments the positioning component can comprise an elastic film with an elasticity, for example, similar to that of skin, or greater than that of skin, or less than that of skin. In embodiments, the LLEC or LLEF system can comprise a laminate where layers of the laminate can be of varying elasticities. For example, an outer layer may be highly elastic and an inner layer in-elastic or less elastic. The in-elastic layer can be made to stretch by placing stress relieving discontinuous regions or slits through the thickness of the material so there is a mechanical displacement rather than stress that would break the fabric weave before stretching would occur. In embodiments the slits can extend completely through a layer or the system or can be placed where expansion is required. In embodiments of the system the slits do not extend all the way through the system or a portion of the system such as the substrate.

In embodiments the device can be shaped to fit an area of desired use, for example the human face, or around a subject's eyes, or around a subject's forehead, a subject's cheeks, a subject's chin, a subject's mouth and nose, or any area where preventing viral transmission is desired. For example, disclosed embodiments comprise masks, such as surgical masks, mask inserts, a mask layer of a multi-layer mask, respirators, and the like, comprising patterned microbatteries that create a unique field between each dot pair.

Further embodiments comprise substrates shaped to fit inside or outside a surgical mask wherein the substrate, for example a planar or non-planar substrate, or a planar substrate that can fold into a non-planar form, comprises patterns of microcells. The patterns can be designed to produce an electric field, an electric current, or both over and through tissue such as human skin. In embodiments the pattern can be designed to produce a specific size, strength, density, shape, or duration of electric field or electric current. In embodiments reservoir or dot size and separation can be altered. The planar substrate can further comprise adhesive. For example at the perimeter (or portion thereof) of the substrate, adhesive provides the user the ability to securely fasten the substrate inside a surgical mask or respirator, outside a surgical mask or respirator, or within a pouch or port in the mask.

In certain embodiments, for example methods of use, it can be preferable to utilize AC or DC current. For example, embodiments disclosed herein can employ phased array, pulsed, square wave, sinusoidal, or other wave forms, or the like. Certain embodiments utilize a controller to produce and control power production and/or distribution to the device.

Embodiments disclosed herein comprise biocompatible electrodes or reservoirs or dots on a surface or substrate, for example a fabric, a fiber, or the like. In embodiments the surface or substrate can be pliable, for example to better follow the contours of an area to be treated, such as the face. In embodiments the surface can comprise a gauze or mesh or plastic. Suitable types of pliable surfaces for use in embodiments disclosed herein can be absorbent or non-absorbent textiles, low-adhesives, vapor permeable films, hydrocolloids, hydrogels, alginates, foams, foam-based materials, cellulose-based materials including Kettenbach fibers, hollow tubes, fibrous materials, such as those impregnated with anhydrous/hygroscopic materials, beads and the like, or any suitable material as known in the art. In embodiments the pliable material can form, for example, a mask, such as that worn on the face, or the like, or an insert shaped to fit a mask. Embodiments can comprise multiple layers. Multi layer embodiments can include, for example, a skin-contacting layer, a layer comprising microcells, and an outer layer.

Disclosed embodiments can comprise non-woven fabric, for example polypropylene. In embodiments, the polypropylene can have a density of, for example, 15, 20, 25, 30, 35, or more g/M$^2$. In further embodiments, a mask can comprise, for example, polyester, cotton, microfiber, cupra, Tencel, bio-cellulose, charcoal, and the like.

Embodiments can include coatings on the surface, such as, for example, over or between the electrodes or cells. Such coatings can include, for example, salts, antivirals, antibacterials, conductive fluid or gel, or the like.

In embodiments the system comprises a component such as elastic to maintain or help maintain its position. In embodiments the system comprises components such as straps to maintain or help maintain its position. In certain embodiments the system or device comprises a strap, for example on either end of the long axis, or a strap linking on end of the long axis to the other. In embodiments that straps can comprise velcro or a similar fastening system. In embodiments the straps can comprise elastic materials. In further embodiments the strap can comprise a conductive material, for example a wire to electrically link the device with other components, such as monitoring equipment or a power source. In embodiments the device can be wirelessly linked to monitoring or data collection equipment, for example linked via Bluetooth to a cell phone that collects data from the device. In certain embodiments the device can comprise data collection means, such as temperature, pressure, or conductivity data collection means. In certain embodiments the device can comprise data transmission means.

An LLEC or LLEF system disclosed herein can comprise straps to affix the system securely, for example around the head of a user. An LLEC or LLEF system disclosed herein can comprise adhesive to affix the system securely, for example affix it inside a surgical mask.

In embodiments, the LLEC or LLEF system can comprise instructions or directions on how to place and use the system to maximize its performance. For example, disclosed kits can comprise instructions regarding "wetting" the system with a conductive liquid prior to use.

Embodiments can comprise a kit comprising a device disclosed herein and an antiviral or antibacterial material.

LLEC/LLEF Systems and Devices; Methods of Manufacture

In embodiments dissimilar metals can be used to create an electric field with a desired voltage. In certain embodiments the pattern of reservoirs can control the watt density and shape of the electric field.

In embodiments printing devices can be used to produce LLEC or LLEF systems disclosed herein. For example, inkjet or "3D" printers can be used to produce embodiments. In embodiments "ink" or "paint" can comprise any conductive solution suitable for forming an electrode on a surface, such as a conductive metal solution. In embodiments "printing" or "painted" can comprise any method of applying a conductive material such as a conductive liquid material to a material upon which a matrix is desired, such as a fabric.

In certain embodiments the binders or inks used to produce LLEC or LLEF systems disclosed herein can include, for example, poly cellulose inks, poly acrylic inks, poly urethane inks, silicone inks, and the like. In embodiments the type of ink used can determine the release rate of electrons from the reservoirs. In embodiments various materials can be added to the ink or binder such as, for example, conductive or resistive materials can be added to alter the shape or strength of the electric field.

In embodiments, electroceutical fabric embodiments disclosed herein can be woven or non-woven. For example, disclosed embodiments can be woven of at least two types of fibers; fibers comprising sections treated or coated with a substance capable of forming a positive electrode; and fibers comprising sections treated or coated with a substance capable of forming a negative electrode. The fabric can further comprise fibers that do not form an electrode. Long lengths of fibers can be woven together to form fabrics. For example, the fibers can be woven together to form a regular pattern of positive and negative electrodes.

Certain embodiments can utilize a power source to create the electric current, such as a battery or a microbattery. The power source can be any energy source capable of generating a current in the system and can include, for example, AC power, DC power, radio frequencies (RF) such as pulsed RF, induction, ultrasound, and the like.

Dissimilar metals used to make an LLEC or LLEF system disclosed herein can be silver and zinc, and the electrolytic solution can include sodium chloride in water. In certain embodiments the electrodes are applied onto a non-conductive surface to create a pattern, most preferably an array or multi-array of voltaic cells that do not spontaneously react until they contact an electrolytic solution. Sections of this description use the terms "printing" with "ink," but it is understood that the patterns may instead be "painted" with "paints." The use of any suitable means for applying a conductive material is contemplated. In embodiments "ink" or "paint" can comprise any solution suitable for forming an electrode on a surface such as a conductive material including a conductive metal solution. In embodiments "printing" or "painted" can comprise any method of applying a solution to a material upon which a matrix is desired.

A preferred material to use in combination with silver to create the voltaic cells or reservoirs of disclosed embodiments is zinc. Zinc has been well-described for its uses in prevention of infection in such topical antibacterial agents as Bacitracin zinc, a zinc salt of Bacitracin. Zinc is a divalent cation with antibacterial properties of its own.

Figure 1:
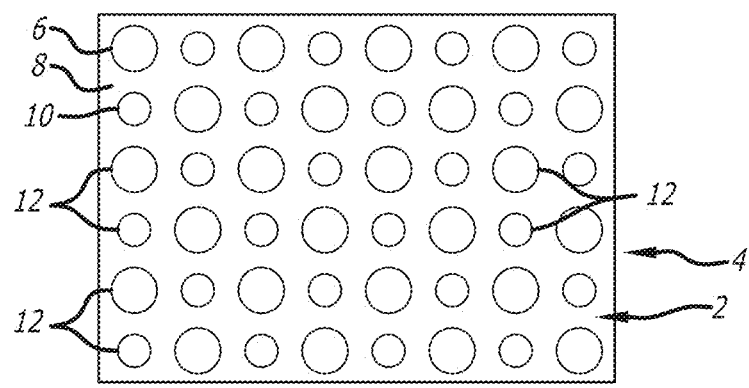
FIG. 1 is a detailed plan view of an embodiment disclosed herein.

Turning to the figures, in FIG. 1, the dissimilar first electrode 6 and second electrode 10 are applied onto a desired primary surface 2 of an article 4. In one embodiment a primary surface is a surface of an LLEC or LLEF system that comes into direct contact with an area to be treated such as a skin surface.

In various embodiments the difference of the standard potentials of the electrodes or dots or reservoirs can be in a range from about 0.05 V to approximately about 5.0 V. For example, the standard potential can be about 0.05 V, about 0.06 V, about 0.07 V, about 0.08 V, about 0.09 V, about 0.1 V, about 0.2 V, about 0.3 V, about 0.4 V, about 0.5 V, about 0.6 V, about 0.7 V, about 0.8 V, about 0.9 V, about 1.0 V, about 1.1 V, about 1.2 V, about 1.3 V, about 1.4 V, about 1.5 V, about 1.6 V, about 1.7 V, about 1.8 V, about 1.9 V, about 2.0 V, about 2.1 V, about 2.2 V, about 2.3 V, about 2.4 V, about 2.5 V, about 2.6 V, about 2.7 V, 2.8 V, about 2.9 V, about 3.0 V, about 3.1 V, about 3.2 V, about 3.3 V, about 3.4 V, about 3.5 V, about 3.6 V, about 3.7 V, about 3.8 V, about 3.9 V, about 4.0 V, about 4.1 V, about 4.2 V, about 4.3 V, 4.4 V, 4.5 V, about 4.6 V, about 4.7 V, 4.8 V, about 4.9 V, about 5.0 V, about 5.1 V, about 5.2 V, about 5.3 V, about 5.4 V, about 5.5 V, about 5.6 V, about 5.7 V, about 5.8 V, about 5.9 V, about 6.0 V, or the like.

In embodiments, LLEC systems disclosed herein can produce a low level electric current of between for example about 1 and about 200 micro-amperes, between about 10 and about 190 micro-amperes, between about 20 and about 180 micro-amperes, between about 30 and about 170 micro-amperes, between about 40 and about 160 micro-amperes, between about 50 and about 150 micro-amperes, between about 60 and about 140 micro-amperes, between about 70 and about 130 micro-amperes, between about 80 and about 120 micro-amperes, between about 90 and about 100 micro-amperes, or the like.

In an embodiment, an LLEC system disclosed herein can produce a low level electric current of between for example about 1 and about 10 micro-amperes In embodiments, LLEC systems disclosed herein can produce a low level micro-current of between for example about 1 and about 400 micro-amperes, between about 20 and about 380 micro-amperes, between about 400 and about 360 micro-amperes, between about 60 and about 340 micro-amperes, between about 80 and about 320 micro-amperes, between about 100 and about 3000 micro-amperes, between about 120 and about 280 micro-amperes, between about 140 and about 260 micro-amperes, between about 160 and about 240 micro-amperes, between about 180 and about 220 micro-amperes, or the like.

In embodiments, LLEC systems disclosed herein can produce a low level micro-current about 10 micro-amperes, about 20 micro-amperes, about 30 micro-amperes, about 40 micro-amperes, about 50 micro-amperes, about 60 micro-amperes, about 70 micro-amperes, about 80 micro-amperes, about 90 micro-amperes, about 100 micro-amperes, about 110 micro-amperes, about 120 micro-amperes, about 130 micro-amperes, about 140 micro-amperes, about 150 micro-amperes, about 160 micro-amperes, about 170 micro-amperes, about 180 micro-amperes, about 190 micro-amperes, about 200 micro-amperes, about 210 micro-amperes, about 220 micro-amperes, about 240 micro-amperes, about 260 micro-amperes, about 280 micro-amperes, about 300 micro-amperes, about 320 micro-amperes, about 340 micro-amperes, about 360 micro-amperes, about 380 micro-amperes, about 400 micro-amperes, or the like.

In embodiments, the disclosed LLEC systems can produce a low level micro-current of not more than 10 micro-amperes, or not more than about 20 micro-amperes, not more than about 30 micro-amperes, not more than about 40 micro-amperes, not more than about 50 micro-amperes, not more than about 60 micro-amperes, not more than about 70 micro-amperes, not more than about 80 micro-amperes, not more than about 90 micro-amperes, not more than about 100 micro-amperes, not more than about 110 micro-amperes, not more than about 120 micro-amperes, not more than about 130 micro-amperes, not more than about 140 micro-amperes, not more than about 150 micro-amperes, not more than about 160 micro-amperes, not more than about 170 micro-amperes, not more than about 180 micro-amperes, not more than about 190 micro-amperes, not more than about 200 micro-amperes, not more than about 210 micro-amperes, not more than about 220 micro-amperes, not more than about 230 micro-amperes, not more than about 240 micro-amperes, not more than about 250 micro-amperes, not more than about 260 micro-amperes, not more than about 270 micro-amperes, not more than about 280 micro-amperes, not more than about 290 micro-amperes, not more than about 300 micro-amperes, not more than about 310 micro-amperes, not more than about 320 micro-amperes, not more than about 340 micro-amperes, not more than about 360 micro-amperes, not more than about 380 micro-amperes, not more than about 400 micro-amperes, not more than about 420 micro-amperes, not more than about 440 micro-amperes, not more than about 460 micro-amperes, not more than about 480 micro-amperes, or the like.

In embodiments, LLEC systems disclosed herein can produce a low level micro-current of not less than 10 micro-amperes, not less than 20 micro-amperes, not less than 30 micro-amperes, not less than 40 micro-amperes, not less than 50 micro-amperes, not less than 60 micro-amperes, not less than 70 micro-amperes, not less than 80 micro-amperes, not less than 90 micro-amperes, not less than 100 micro-amperes, not less than 110 micro-amperes, not less than 120 micro-amperes, not less than 130 micro-amperes, not less than 140 micro-amperes, not less than 150 micro-amperes, not less than 160 micro-amperes, not less than 170 micro-amperes, not less than 180 micro-amperes, not less than 190 micro-amperes, not less than 200 micro-amperes, not less than 210 micro-amperes, not less than 220 micro-amperes, not less than 230 micro-amperes, not less than 240 micro-amperes, not less than 250 micro-amperes, not less than 260 micro-amperes, not less than 270 micro-amperes, not less than 280 micro-amperes, not less than 290 micro-amperes, not less than 300 micro-amperes, not less than 310 micro-amperes, not less than 320 micro-amperes, not less than 330 micro-amperes, not less than 340 micro-amperes, not less than 350 micro-amperes, not less than 360 micro-amperes, not less than 370 micro-amperes, not less than 380 micro-amperes, not less than 390 micro-amperes, not less than 400 micro-amperes, or the like.

The applied electrodes or reservoirs or dots can adhere or bond to the primary surface 2 because a biocompatible binder is mixed, in embodiments into separate mixtures, with each of the dissimilar metals that will create the pattern of voltaic cells, in embodiments. Most inks are simply a carrier, and a binder mixed with pigment. Similarly, conductive metal solutions can be a binder mixed with a conductive element. The resulting conductive metal solutions can be used with an application method such as screen printing to apply the electrodes to the primary surface in predetermined patterns. Once the conductive metal solutions dry and/or cure, the patterns of spaced electrodes can substantially maintain their relative position, even on a flexible material such as that used for an LLEC or LLEF system. To make a limited number of the systems of an embodiment disclosed herein, the conductive metal solutions can be hand applied onto a common adhesive bandage so that there is an array of alternating electrodes that are spaced about a millimeter apart on the primary surface of the bandage. The solution can be allowed to dry before being applied to a surface so that the conductive materials do not mix, which could interrupt the array and cause direct reactions that will release the elements.

In certain embodiments that utilize a poly-cellulose binder, the binder itself can have an beneficial effect such as reducing the local concentration of matrix metallo-proteases through an iontophoretic process that drives the cellulose into the surrounding tissue. This process can be used to electronically drive other components such as drugs into the surrounding tissue.

The binder can include any biocompatible liquid material that can be mixed with a conductive element (preferably metallic crystals of silver or zinc) to create a conductive solution which can be applied as a thin coating to a surface. One suitable binder is a solvent reducible polymer, such as the polyacrylic non-toxic silk-screen ink manufactured by COLORCON® Inc., a division of Berwind Pharmaceutical Services, Inc. (see COLORCON® NO-TOX® product line, part number NT28). In an embodiment the binder is mixed with high purity (at least 99.999%) metallic silver crystals to make the silver conductive solution. The silver crystals, which can be made by grinding silver into a powder, are preferably smaller than 100 microns in size or about as fine as flour. In an embodiment, the size of the crystals is about 325 mesh, which is typically about 40 microns in size or a little smaller. The binder is separately mixed with high purity (at least 99.99%, in an embodiment) metallic zinc powder which has also preferably been sifted through standard 325 mesh screen, to make the zinc conductive solution. For better quality control and more consistent results, most of the crystals used should be larger than 325 mesh and smaller than 200 mesh. For example the crystals used should be between 200 mesh and 325 mesh, or between 210 mesh and 310 mesh, between 220 mesh and 300 mesh, between 230 mesh and 290 mesh, between 240 mesh and 280 mesh, between 250 mesh and 270 mesh, between 255 mesh and 265 mesh, or the like.

Other powders of metal can be used to make other conductive metal solutions in the same way as described in other embodiments.

The size of the metal crystals, the availability of the surface to the conductive fluid and the ratio of metal to binder affects the release rate of the metal from the mixture. When COLORCON® polyacrylic ink is used as the binder, about 10 to 40 percent of the mixture should be metal for a longer term bandage (for example, one that stays on for about 10 days). For example, for a longer term LLEC or LLEF system the percent of the mixture that should be metal can be 8 percent, or 10 percent, 12 percent, 14 percent, 16 percent, 18 percent, 20 percent, 22 percent, 24 percent, 26 percent, 28 percent, 30 percent, 32 percent, 34 percent, 36 percent, 38 percent, 40 percent, 42 percent, 44 percent, 46 percent, 48 percent, 50 percent, or the like.

If the same binder is used, but the percentage of the mixture that is metal is increased to 60 percent or higher, then the release rate will be much faster and a typical system will only be effective for a few days. For example, for a shorter term device, the percent of the mixture that should be metal can be 40 percent, or 42 percent, 44 percent, 46 percent, 48 percent, 50 percent, 52 percent, 54 percent, 56 percent, 58 percent, 60 percent, 62 percent, 64 percent, 66 percent, 68 percent, 70 percent, 72 percent, 74 percent, 76 percent, 78 percent, 80 percent, 82 percent, 84 percent, 86 percent, 88 percent, 90 percent, or the like.

For LLEC or LLEF systems comprising a pliable substrate it can be desirable to decrease the percentage of metal down to, for example, 5 percent or less, or to use a binder that causes the crystals to be more deeply embedded, so that the primary surface will be antimicrobial for a very long period of time and will not wear prematurely. Other binders can dissolve or otherwise break down faster or slower than a polyacrylic ink, so adjustments can be made to achieve the desired rate of spontaneous reactions from the voltaic cells.

To maximize the number of voltaic cells, in various embodiments, a pattern of alternating silver masses or electrodes or reservoirs and zinc masses or electrodes or reservoirs can create an array of electrical currents across the primary surface. A basic pattern, shown in FIG. 1, has each mass of silver equally spaced from four masses of zinc, and has each mass of zinc equally spaced from four masses of silver, according to an embodiment. The first electrode 6 is separated from the second electrode 10 by a spacing 8. The designs of first electrode 6 and second electrode 10 are simply round dots, and in an embodiment, are repeated. Numerous repetitions 12 of the designs result in a pattern. For an exemplary device comprising silver and zinc, each silver design preferably has about twice as much mass as each zinc design, in an embodiment. For the pattern in FIG. 1, the silver designs are most preferably about a millimeter from each of the closest four zinc designs, and vice-versa. The resulting pattern of dissimilar metal masses defines an array of voltaic cells when introduced to an electrolytic solution. Further disclosure relating to methods of producing micro-arrays can be found in U.S. Pat. No. 7,813,806 entitled CURRENT PRODUCING SURFACE FOR TREATING BIOLOGIC TISSUE issued Oct. 12, 2010, which is incorporated by reference in its entirety.

Figure 2:
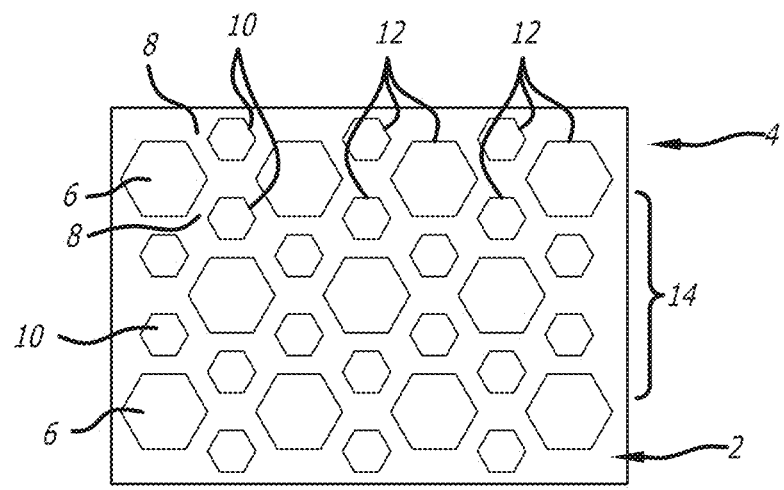
FIG. 2 is a detailed plan view of a pattern of applied electrical conductors in accordance with an embodiment disclosed herein.

A dot pattern of masses like the alternating round dots of FIG. 1 can be preferred when applying conductive material onto a flexible material, such as those used for a surgical or medical mask or respirator, as the dots won't significantly affect the flexibility of the material. To maximize the density of electrical current over a primary surface the pattern of FIG. 2 can be used. The first electrode 6 in FIG. 2 is a large hexagonally shaped dot, and the second electrode 10 is a pair of smaller hexagonally shaped dots that are spaced from each other. The spacing 8 that is between the first electrode 6 and the second electrode 10 maintains a relatively consistent distance between adjacent sides of the designs. Numerous repetitions 12 of the designs result in a pattern 14 that can be described as at least one of the first design being surrounded by six hexagonally shaped dots of the second design. In embodiments, electrodes can be deposited or placed on both sides of a planar substrate, for example, both sides of a mask, for example both sides of (interior facing the patient and exterior facing away from the patient) a surgical mask.

Figure 3:
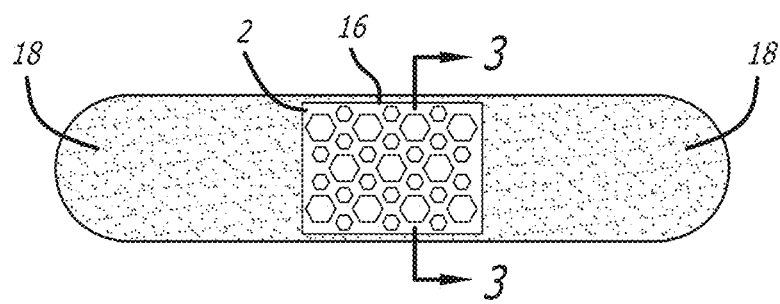
FIG. 3 is an embodiment using the applied pattern of FIG. 2.
Figure 4:
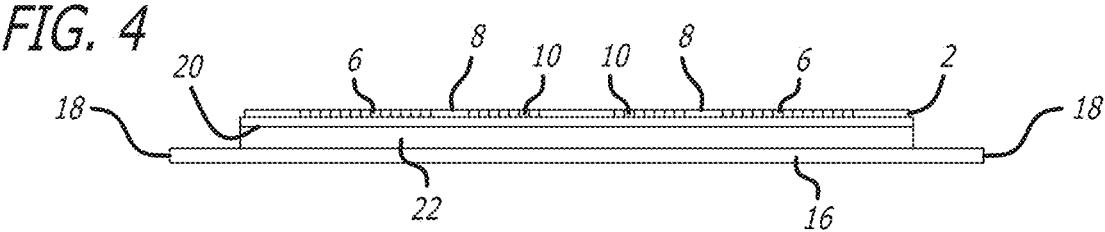
FIG. 4 is a cross-section of FIG. 3 through line 3-3.

FIGS. 3 and 4 show how the pattern of FIG. 2 can be used to make an embodiment disclosed herein. The pattern shown in detail in FIG. 2 is applied to the primary surface 2 of an embodiment. The back 20 of the printed material is fixed to a substrate layer 22. This layer is adhesively fixed to a pliable layer 16.

Figure 5:
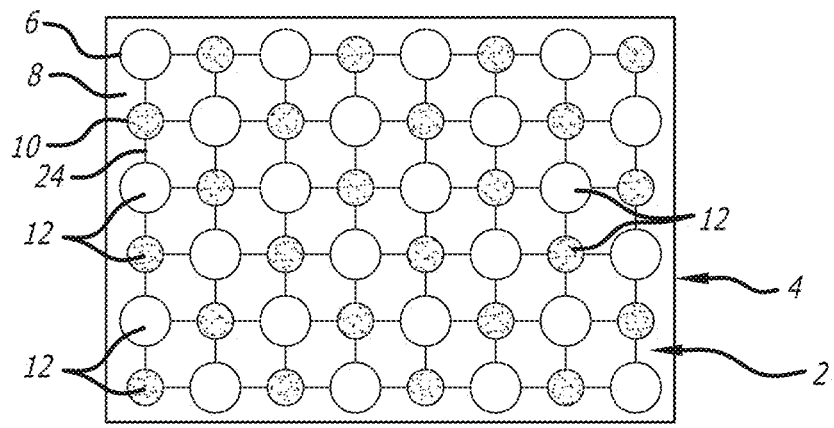
FIG. 5 is a detailed plan view of an embodiment disclosed herein which includes fine lines of conductive metal solution connecting electrodes.

FIG. 5 shows an additional feature, which can be added between designs, that can initiate the flow of current in a poor electrolytic solution. A fine line 24 is printed using one of the conductive metal solutions along a current path of each voltaic cell. The fine line will initially have a direct reaction but will be depleted until the distance between the electrodes increases to where maximum voltage is realized. The initial current produced is intended to help control edema so that the LLEC system will be effective. If the electrolytic solution is highly conductive when the system is initially applied the fine line can be quickly depleted and the device will function as though the fine line had never existed.

Figure 6:
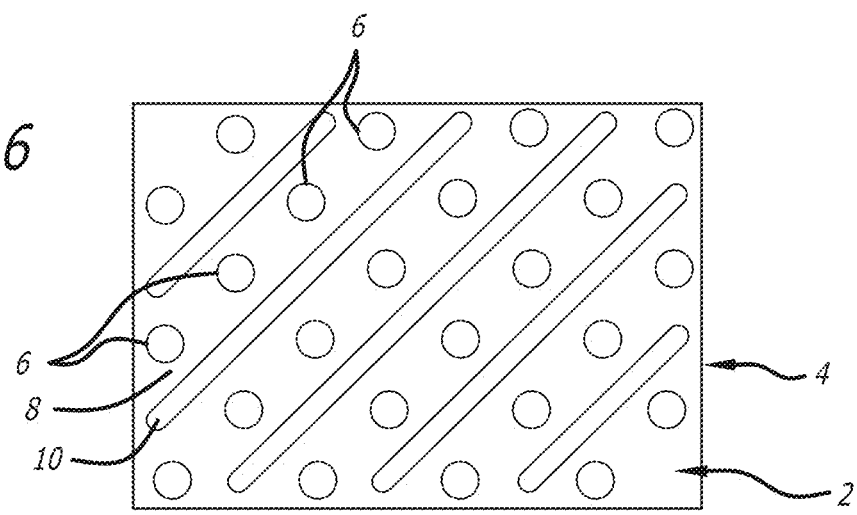
FIG. 6 is a detailed plan view of an embodiment having a line pattern and dot pattern.
Figure 7:
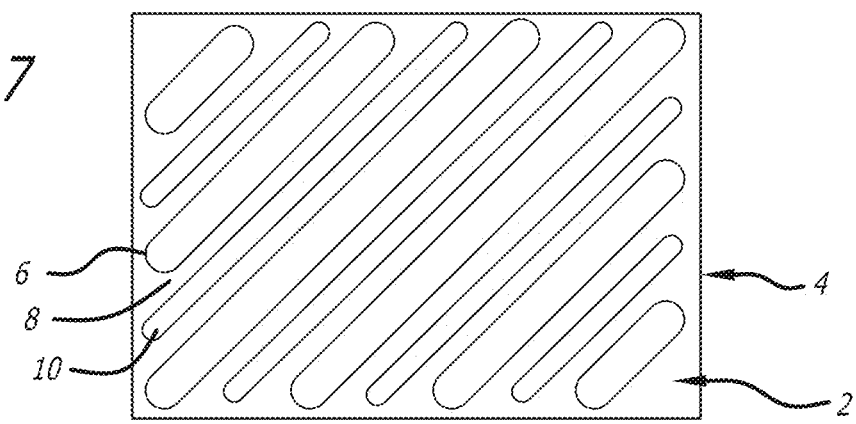
FIG. 7 is a detailed plan view of an embodiment having two line patterns.
Figure 8A:
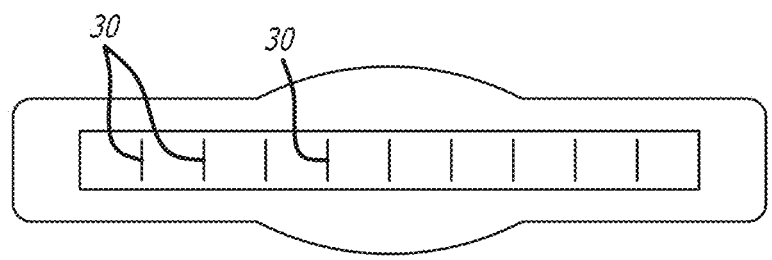
FIG. 8A depicts an embodiment showing the location of discontinuous regions as well as anchor regions of the system.
Figure 8B:
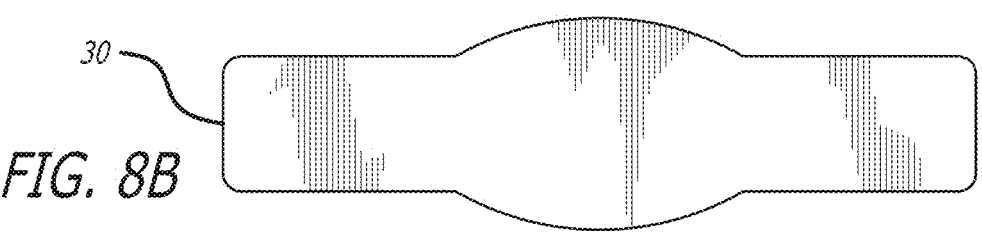
FIG. 8B depicts an embodiment showing the location of discontinuous regions as well as anchor regions of the system.
Figure 8C:
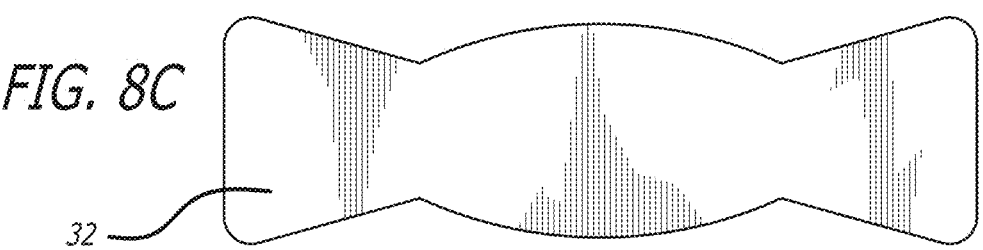
FIG. 8C depicts an embodiment showing the location of discontinuous regions as well as anchor regions of the system.
Figure 8D:
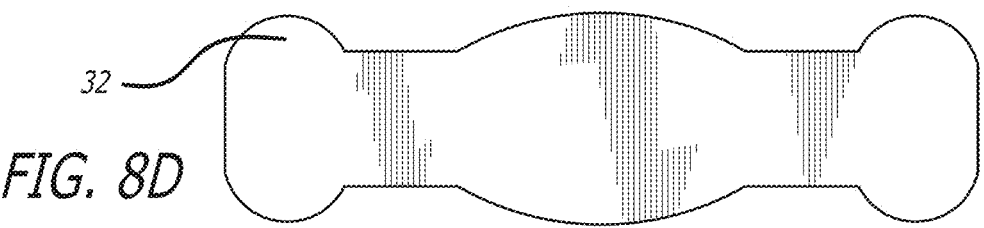
FIG. 8D depicts an embodiment showing the location of discontinuous regions as well as anchor regions of the system.
Figure 8E:
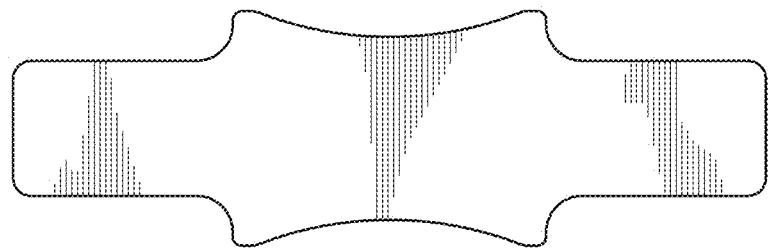
FIG. 8E depicts an embodiment showing the location of discontinuous regions as well as anchor regions of the system.

FIGS. 6 and 7 show alternative patterns that use at least one line design. The first electrode 6 of FIG. 6 is a round dot similar to the first design used in FIG. 1. The second electrode 10 of FIG. 6 is a line. When the designs are repeated, they define a pattern of parallel lines that are separated by numerous spaced dots. FIG. 7 uses only line designs. The first electrode 6 can be thicker or wider than the second electrode 10 if the oxidation-reduction reaction requires more metal from the first conductive element (mixed into the first design's conductive metal solution) than the second conductive element (mixed into the second design's conductive metal solution). The lines can be dashed. Another pattern can be silver grid lines that have zinc masses in the center of each of the cells of the grid. The pattern can be letters printed from alternating conductive materials so that a message can be printed onto the primary surface-perhaps a brand name or identifying information such as patient blood type.

Because the spontaneous oxidation-reduction reaction of silver and zinc uses a ratio of approximately two silver to one zinc, the silver design can contain about twice as much mass as the zinc design in an embodiment. At a spacing of about 1 mm between the closest dissimilar metals (closest edge to closest edge) each voltaic cell that contacts a conductive fluid can create approximately 1 volt of potential that will penetrate substantially through the dermis and epidermis. Closer spacing of the dots can decrease the resistance, providing less potential, and the current will not penetrate as deeply. If the spacing falls below about one tenth of a millimeter a benefit of the spontaneous reaction is that which is also present with a direct reaction; silver can be electrically driven into the skin. Therefore, spacing between the closest conductive materials can be 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or the like.

In certain embodiments the spacing between the closest conductive materials can be not more than 0.1 mm, not more than 0.2 mm, not more than 0.3 mm, not more than 0.4 mm, not more than 0.5 mm, not more than 0.6 mm, not more than 0.7 mm, not more than 0.8 mm, not more than 0.9 mm, not more than 1 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5 mm, not more than 5.1 mm, not more than 5.2 mm, not more than 5.3 mm, not more than 5.4 mm, not more than 5.5 mm, not more than 5.6 mm, not more than 5.7 mm, not more than 5.8 mm, not more than 5.9 mm, not more than 6 mm, or the like.

In certain embodiments spacing between the closest conductive materials can be not less than 0.1 mm, not less than 0.2 mm, not less than 0.3 mm, not less than 0.4 mm, not less than 0.5 mm, not less than 0.6 mm, not less than 0.7 mm, not less than 0.8 mm, not less than 0.9 mm, not less than 1 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5 mm, not less than 5.1 mm, not less than 5.2 mm, not less than 5.3 mm, not less than 5.4 mm, not less than 5.5 mm, not less than 5.6 mm, not less than 5.7 mm, not less than 5.8 mm, not less than 5.9 mm, not less than 6 mm, or the like.

Disclosed herein include LLEC or LLEF systems comprising a primary surface of a pliable material wherein the pliable material is adapted to be applied to an area of tissue such as the face of a subject; a first electrode design formed from a first conductive liquid that includes a mixture of a polymer and a first element, the first conductive liquid being applied into a position of contact with the primary surface, the first element including a metal species, and the first electrode design including at least one dot or reservoir, wherein selective ones of the at least one dot or reservoir have approximately a 1.5 mm+/−1 mm mean diameter; a second electrode design formed from a second conductive liquid that includes a mixture of a polymer and a second element, the second element including a different metal species than the first element, the second conductive liquid being printed into a position of contact with the primary surface, and the second electrode design including at least one other dot or reservoir, wherein selective ones of the at least one other dot or reservoir have approximately a 2.5 mm+/−2 mm mean diameter; a spacing on the primary surface that is between the first electrode design and the second electrode design such that the first electrode design does not physically contact the second electrode design, wherein the spacing is approximately 1.5 mm+/−1 mm, and at least one repetition of the first electrode design and the second electrode design, the at least one repetition of the first electrode design being substantially adjacent the second electrode design, wherein the at least one repetition of the first electrode design and the second electrode design, in conjunction with the spacing between the first electrode design and the second electrode design, defines at least one pattern of at least one voltaic cell for spontaneously generating at least one electrical current when introduced to an electrolytic solution. Therefore, in embodiments, electrodes, dots or reservoirs can have a mean diameter of 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, or the like.

In further embodiments, electrodes, dots or reservoirs can have a mean diameter of not less than 0.2 mm, not less than 0.3 mm, not less than 0.4 mm, not less than 0.5 mm, not less than 0.6 mm, not less than 0.7 mm, not less than 0.8 mm, not less than 0.9 mm, not less than 1.0 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2.0 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3.0 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4.0 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5.0 mm, or the like.

In further embodiments, electrodes, dots or reservoirs can have a mean diameter of not more than 0.2 mm, not more than 0.3 mm, not more than 0.4 mm, not more than 0.5 mm, not more than 0.6 mm, not more than 0.7 mm, not more than 0.8 mm, not more than 0.9 mm, not more than 1.0 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2.0 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3.0 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4.0 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5.0 mm, or the like.

In embodiments, the density of the conductive materials can be, for example, 20 reservoirs per square inch (/in$^2$), 30 reservoirs/in$^2$, 40 reservoirs/in$^2$, 50 reservoirs/in$^2$, 60 reservoirs/in$^2$, 70 reservoirs/in$^2$, 80 reservoirs/in$^2$, r 90 reservoirs/in$^2$, 100 reservoirs/in$^2$, 150 reservoirs/in$^2$, 200 reservoirs/in$^2$, 250 reservoirs/in$^2$, 300 reservoirs/in$^2$, or 350 reservoirs/in$^2$, 400 reservoirs/in$^2$, 450 reservoirs/in$^2$, 500 reservoirs/in$^2$, 550 reservoirs/in$^2$, 600 reservoirs/in$^2$, 650 reservoirs/in$^2$, 700 reservoirs/in$^2$, 750 reservoirs/in$^2$, more, or the like.

In embodiments, the density of the conductive materials can be, for example, more than 20 reservoirs/in$^2$, more than 30 reservoirs/in$^2$, more than 40 reservoirs/in$^2$, more than 50 reservoirs/in$^2$, more than 60 reservoirs/in$^2$, more than 70 reservoirs/in$^2$, more than 80 reservoirs/in$^2$, more than 90 reservoirs/in$^2$, more than 100 reservoirs/in$^2$, more than 150 reservoirs/in$^2$, more than 200 reservoirs/in$^2$, more than 250 reservoirs/in$^2$, more than 300 reservoirs/in$^2$, more than 350 reservoirs/in$^2$, more than 400 reservoirs/in$^2$, more than 450 reservoirs/in$^2$, more than 500 reservoirs/in$^2$, more than 550 reservoirs/in$^2$, more than 600 reservoirs/in$^2$, more than 650 reservoirs/in$^2$, more than 700 reservoirs/in$^2$, more than 750 reservoirs/in$^2$, or more, or the like.

The material concentrations or quantities within and/or the relative sizes (e.g., dimensions or surface area) of the first and second reservoirs can be selected deliberately to achieve various characteristics of the systems' behavior. For example, the quantities of material within a first and second reservoir can be selected to provide an apparatus having an operational behavior that depletes at approximately a desired rate and/or that "dies" after an approximate period of time after activation. In an embodiment the one or more first reservoirs and the one or more second reservoirs are configured to sustain one or more currents for an approximate pre-determined period of time, after activation. It is to be understood that the amount of time that currents are sustained can depend on external conditions and factors (e.g., the quantity and type of activation material), and currents can occur intermittently depending on the presence or absence of activation material. Further disclosure relating to producing reservoirs that are configured to sustain one or more currents for an approximate pre-determined period of time can be found in U.S. Pat. No. 7,904,147 entitled SUBSTANTIALLY PLANAR ARTICLE AND METHODS OF MANUFACTURE issued Mar. 8, 2011, which is incorporated by reference herein in its entirety.

In various embodiments the difference of the standard potentials of the first and second reservoirs can be in a range from 0.05 V to approximately 5.0 V. For example, the standard potential can be 0.05 V, or 0.06 V, 0.07 V, 0.08 V, 0.09 V, 0.1 V, 0.2 V, 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V, 1.6 V, 1.7 V, 1.8 V, 1.9 V, 2.0 V, 2.1 V, 2.2 V, 2.3 V, 2.4 V, 2.5 V, 2.6 V, 2.7 V, 2.8 V, 2.9 V, 3.0 V, 3.1 V, 3.2 V, 3.3 V, 3.4 V, 3.5 V, 3.6 V, 3.7 V, 3.8 V, 3.9 V, 4.0 V, 4.1 V, 4.2 V, 4.3 V, 4.4 V, 4.5 V, 4.6 V, 4.7 V, 4.8 V, 4.9 V, 5.0 V, or the like.

In a particular embodiment the difference of the standard potentials of the first and second reservoirs can be at least 0.05 V, at least 0.06 V, at least 0.07 V, at least 0.08 V, at least 0.09 V, at least 0.1 V, at least 0.2 V, at least 0.3 V, at least 0.4 V, at least 0.5 V, at least 0.6 V, at least 0.7 V, at least 0.8 V, at least 0.9 V, at least 1.0 V, at least 1.1 V, at least 1.2 V, at least 1.3 V, at least 1.4 V, at least 1.5 V, at least 1.6 V, at least 1.7 V, at least 1.8 V, at least 1.9 V, at least 2.0 V, at least 2.1 V, at least 2.2 V, at least 2.3 V, at least 2.4 V, at least 2.5 V, at least 2.6 V, at least 2.7 V, at least 2.8 V, at least 2.9 V, at least 3.0 V, at least 3.1 V, at least 3.2 V, at least 3.3 V, at least 3.4 V, at least 3.5 V, at least 3.6 V, at least 3.7 V, at least 3.8 V, at least 3.9 V, at least 4.0 V, at least 4.1 V, at least 4.2 V, at least 4.3 V, at least 4.4 V, at least 4.5 V, at least 4.6 V, at least 4.7 V, at least 4.8 V, at least 4.9 V, at least 5.0 V, or the like.

In a particular embodiment, the difference of the standard potentials of the first and second reservoirs can be not more than 0.05 V, not more than 0.06 V, not more than 0.07 V, not more than 0.08 V, not more than 0.09 V, not more than 0.1 V, not more than 0.2 V, not more than 0.3 V, not more than 0.4 V, not more than 0.5 V, not more than 0.6 V, not more than 0.7 V, not more than 0.8 V, not more than 0.9 V, not more than 1.0 V, not more than 1.1 V, not more than 1.2 V, not more than 1.3 V, not more than 1.4 V, not more than 1.5 V, not more than 1.6 V, not more than 1.7 V, not more than 1.8 V, not more than 1.9 V, not more than 2.0 V, not more than 2.1 V, not more than 2.2 V, not more than 2.3 V, not more than 2.4 V, not more than 2.5 V, not more than 2.6 V, not more than 2.7 V, not more than 2.8 V, not more than 2.9 V, not more than 3.0 V, not more than 3.1 V, not more than 3.2 V, not more than 3.3 V, not more than 3.4 V, not more than 3.5 V, not more than 3.6 V, not more than 3.7 V, not more than 3.8 V, not more than 3.9 V, not more than 4.0 V, not more than 4.1 V, not more than 4.2 V, not more than 4.3 V, not more than 4.4 V, not more than 4.5 V, not more than 4.6 V, not more than 4.7 V, not more than 4.8 V, not more than 4.9 V, not more than 5.0 V, or the like. In embodiments that include very small reservoirs (e.g., on the nanometer scale), the difference of the standard potentials can be substantially less or more. The electrons that pass between the first reservoir and the second reservoir can be generated as a result of the difference of the standard potentials. Further disclosure relating to standard potentials can be found in U.S. Pat. No. 8,224,439 entitled BATTERIES AND METHODS OF MANUFACTURE AND USE issued Jul. 17, 2012, which is incorporated be reference herein in its entirety.

The voltage present at the site of treatment is typically in the range of millivolts but disclosed embodiments can introduce a much higher voltage, for example near 1 volt when using the 1 mm spacing of dissimilar metals already described. The higher voltage is believed to drive the current deeper into the treatment area. In this way the current not only can drive silver and zinc into the treatment if desired for treatment, but the current can also provide a stimulatory current so that the entire surface area can be treated. The higher voltage may also increase antimicrobial effect bacteria and preventing biofilms. The electric field can also have beneficial effects on cell migration, ATP production, and angiogenesis.

While various embodiments have been shown and described, it will be realized that alterations and modifications can be made thereto without departing from the scope of the following claims. It is expected that other methods of applying the conductive material can be substituted as appropriate. Also, there are numerous shapes, sizes and patterns of voltaic cells that have not been described but it is expected that this disclosure will enable those skilled in the art to incorporate their own designs which will then be applied to a surface to create voltaic cells which will become active when brought into contact with an electrolytic solution.

Certain embodiments include LLEC or LLEF systems comprising embodiments designed to be used on irregular, non-planar, or "stretching" surfaces. Embodiments disclosed herein can be used with numerous irregular surfaces of the body, including the face, etc. Additional embodiments disclosed herein can be used in areas where tissue is prone to movement, for example the eyelid, the ear, the lips, the nose, etc.

Figure 9:
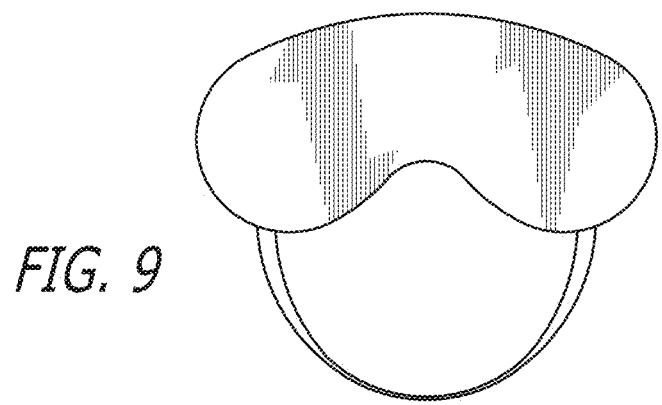
FIG. 9 depicts an embodiment showing a mask comprising a multi-array matrix of biocompatible microcells and means for securing the mask.
Figure 10:
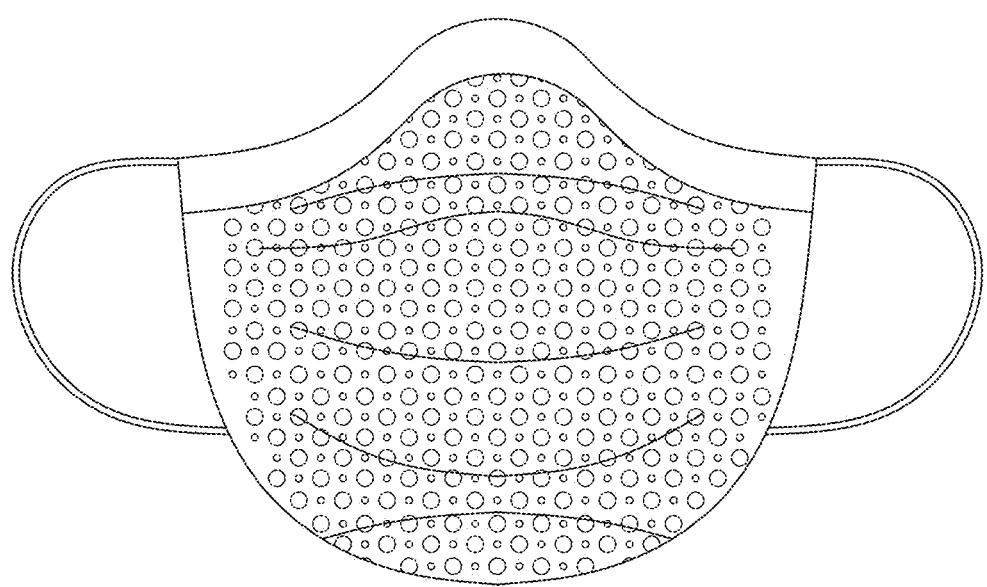
FIG. 10 depicts an embodiment showing a mask.
Figure 11:
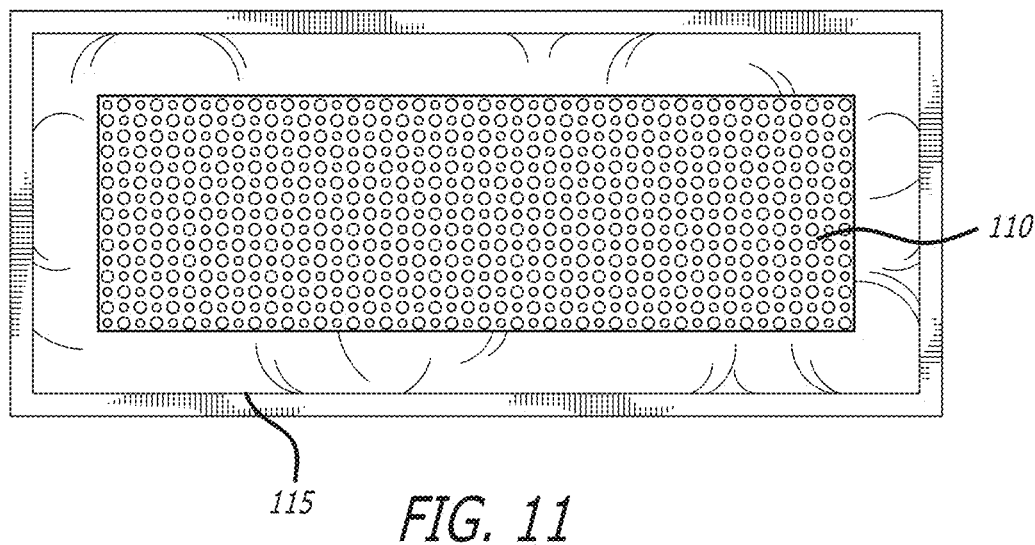
FIG. 11 depicts a substrate described herein.
Figure 12:
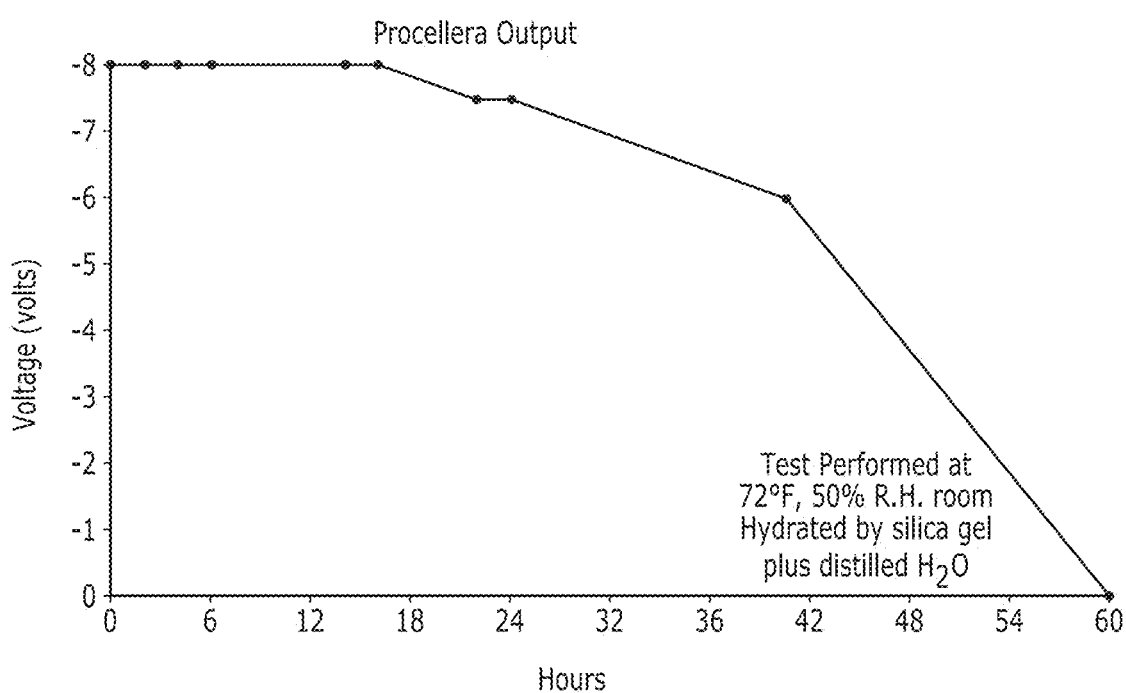
FIG. 12 depicts PROCELLERA® (an embodiment disclosed herein) output over time.
Figure 13:
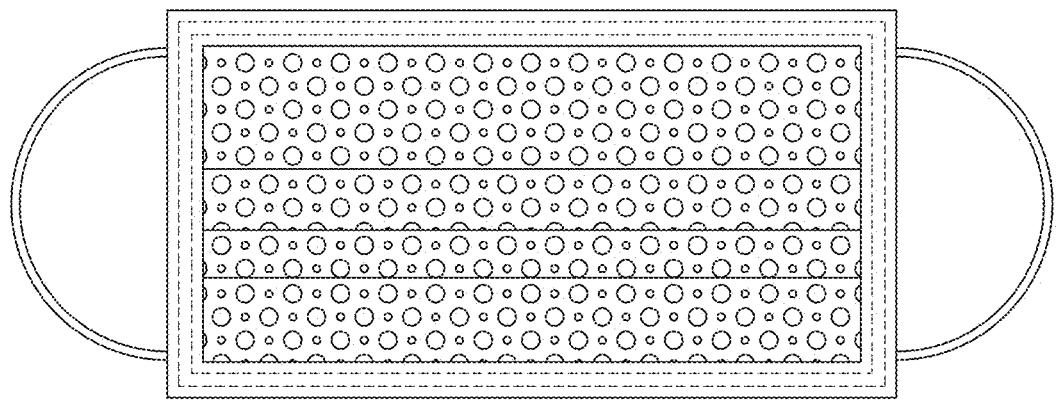
FIG. 13 depicts an embodiment showing a mask.

In certain embodiments, the substrate can be shaped to fit a particular region of the body. As shown in FIG. 9, an eye mask-shaped substrate can be used for the treatment around the face and forehead. FIGS. 23-26 show additional embodiments for use in covering a user's mouth and nose.

Embodiments can also include means for securing the mask to the user's head. In an embodiment the portion of the mask or substrate that is to contact the skin comprises a multi-array matrix of biocompatible microcells. In certain embodiments a fluid or cream such as a conductive fluid or cream can be applied between the multi-array matrix of biocompatible microcells and the skin.

Embodiments can comprise a moisture-sensitive component that changes color when the device is activated and producing an electric current.

Various apparatus embodiments which can be referred to as "medical batteries" are described herein. Further disclosure relating to this technology can be found in U.S. Pat. No. 7,672,719 entitled BATTERIES AND METHODS OF MANUFACTURE AND USE issued Mar. 2, 2010, which is incorporated herein by reference in its entirety.

Certain embodiments disclosed herein include a method of manufacturing an LLEC or LLEF system, the method comprising joining with a substrate multiple first reservoirs wherein selected ones of the multiple first reservoirs include a reducing agent, and wherein first reservoir surfaces of selected ones of the multiple first reservoirs are proximate to a first substrate surface; and joining with the substrate multiple second reservoirs wherein selected ones of the multiple second reservoirs include an oxidizing agent, and wherein second reservoir surfaces of selected ones of the multiple second reservoirs are proximate to the first substrate surface, wherein joining the multiple first reservoirs and joining the multiple second reservoirs comprises joining using tattooing. In embodiments the substrate can comprise gauzes comprising dots or electrodes.

Further embodiments can include a method of manufacturing an LLEC or LLEF system, the method comprising joining with a substrate multiple first reservoirs wherein selected ones of the multiple first reservoirs include a reducing agent, and wherein first reservoir surfaces of selected ones of the multiple first reservoirs are proximate to a first substrate surface; and joining with the substrate multiple second reservoirs wherein selected ones of the multiple second reservoirs include an oxidizing agent, and wherein second reservoir surfaces of selected ones of the multiple second reservoirs are proximate to the first substrate surface, wherein joining the multiple first reservoirs and joining the multiple second reservoirs comprises: combining the multiple first reservoirs, the multiple second reservoirs, and multiple parallel insulators to produce a pattern repeat arranged in a first direction across a plane, the pattern repeat including a sequence of a first one of the parallel insulators, one of the multiple first reservoirs, a second one of the parallel insulators, and one of the multiple second reservoirs; and weaving multiple transverse insulators through the first parallel insulator, the one first reservoir, the second parallel insulator, and the one second reservoir in a second direction across the plane to produce a woven apparatus.

Embodiments disclosed herein include LLEC and LLEF systems that can produce an electrical stimulus and/or can electromotivate, electroconduct, electroinduct, electrotransport, and/or electrophorese one or more therapeutic materials in areas of target tissue (e.g., iontophoresis), and/or can cause one or more biologic or other materials in proximity to, on or within target tissue to be rejuvenated. Further disclosure relating to materials that can produce an electrical stimulus can be found in U.S. Pat. No. 7,662,176 entitled FOOTWEAR APPARATUS AND METHODS OF MANUFACTURE AND USE issued Feb. 16, 2010, which is incorporated herein by reference in its entirety.

Embodiments disclosed herein include a multilayer fabric, for example a layer that can produce an LLEC/LLEF as described herein, a hydration layer, and a waterproof layer. Further embodiments comprise a layer of a multilayer mask such as a surgical mask or respirator, including for example an N95 mask.

Embodiments can comprise a conductive material, for example a salt, to assist in maintaining a conductive environment.

LLEC/LLEF Systems and Devices; Methods of Use

In embodiments, methods and devices disclosed herein can be used for to prevent viral transmission. For example, disclosed embodiments comprise masks, for example surgical masks, surgical mask inserts, respirators, respirator inserts, and the like, comprising electrodes.

Disclosed embodiments can be used for preventing virus transmission, for example those that can spread via direct contact, aerosol, or oral pathways.

Disclosed embodiments can be used to prevent transmission of, for example, dsDNA viruses, ssDNA viruses, dsRNA viruses, (+)ssRNA viruses, (−)ssRNA viruses, ssRNA-RT viruses, dsDNA-RT viruses, and the like.

Disclosed embodiments can be used to prevent transmission of, for example, Chikungunya, Cholera, Crimean-Congo haemorrhagic fever, Ebola virus disease, Hendra virus infection, Influenza (pandemic, seasonal, zoonotic), Lassa fever, Marburg virus disease, Meningitis, MERS-CoV, Monkeypox, Nipah virus infection, Novel coronavirus (2019-nCoV), Plague, Rift Valley fever, SARS, Smallpox, Tularaemia, Yellow fever, Zika virus disease, and the like.

In embodiments, a disclosed mask is worn by an infected mammal to prevent viral propagation.

In embodiments, a disclosed mask is worn by a healthy mammal to prevent viral acquisition.

In embodiments, a disclosed mask insert is worn by an infected mammal to prevent viral propagation.

In embodiments, a disclosed mask insert is worn by a healthy mammal to prevent viral acquisition.

In an exemplary embodiment, a method disclosed herein comprises applying a disclosed device to an area where treatment is desired, for example, over the mouth, nose, eyes, etc.

In another exemplary embodiment, a method disclosed herein comprises applying a disclosed mask insert to a surgical mask to provide increased anti-viral performance as compared to the antiviral performance of the mask alone.

EXAMPLES

The following non-limiting examples are provided for illustrative purposes only in order to facilitate a more complete understanding of representative embodiments. These examples should not be construed to limit any of the embodiments described in the present specification.

Example 1

Cell Migration Assay

The in vitro scratch assay is an easy, low-cost and well-developed method to measure cell migration in vitro. The basic steps involve creating a "scratch" in a cell monolayer, capturing images at the beginning and at regular intervals during cell migration to close the scratch, and comparing the images to quantify the migration rate of the cells. Compared to other methods, the in vitro scratch assay is particularly suitable for studies on the effects of cell-matrix and cell-cell interactions on cell migration, mimic cell migration during wound healing in vivo and are compatible with imaging of live cells during migration to monitor intracellular events if desired. In addition to monitoring migration of homogenous cell populations, this method has also been adopted to measure migration of individual cells in the leading edge of the scratch. Not taking into account the time for transfection of cells, in vitro scratch assay per se usually takes from several hours to overnight.

Human keratinocytes were plated under plated under placebo or an LLEC system (labeled "PROCELLERA®"). Cells were also plated under silver-only or zinc-only dressings. After 24 hours, the scratch assay was performed. Cells plated under the PROCELLERA® device displayed increased migration into the "scratched" area as compared to any of the zinc, silver, or placebo dressings. After 9 hours, the cells plated under the PROCELLERA® device had almost "closed" the scratch. This demonstrates the importance of electrical activity to cell migration and infiltration.

In addition to the scratch test, genetic expression was tested. Increased insulin growth factor (IGF)-1R phosphorylation was demonstrated by the cells plated under the PROCELLERA® device as compared to cells plated under insulin growth factor alone.

Integrin accumulation also affects cell migration. An increase in integrin accumulation achieved with the LLEC system. Integrin is necessary for cell migration, and is found on the leading edge of migrating cell.

Thus, the tested LLEC system enhanced cellular migration and IGF-1R/integrin involvement. This involvement demonstrates the effect that the LLEC system had upon cell receptors involved with the wound healing process.

Example 2

Zone of Inhibition Test

For cellular repair to be most efficient, available energy should not be shared with ubiquitous microbes. In this "zone of inhibition" test, placebo, an LLEC device (PROCELLERA®) and silver only were tested in an agar medium with a 24 hour growth of organisms. Bacterial growth was present over the placebo, a zone of inhibition over the PROCELLERA® and a minimal inhibition zone over the silver. Because the samples were "buried" in agar, the electricidal effect of the LLEC system could be tested. Silver ion diffusion, the method used by silver based antimicrobials, alone was not sufficient. The test demonstrates the improved bactericidal effect of PROCELLERA® as compared to silver alone.

Example 3

LLEC Influence on Human Keratinocyte Migration

An LLEC-generated electrical field was mapped, leading to the observation that LLEC generates hydrogen peroxide, known to drive redox signaling. LLEC-induced phosphorylation of redox-sensitive IGF-1R was directly implicated in cell migration. The LLEC also increased keratinocyte mitochondrial membrane potential.

The LLEC was made of polyester printed with dissimilar elemental metals as described herein. It comprises alternating circular regions of silver and zinc dots, along with a proprietary, biocompatible binder added to lock the electrodes to the surface of a flexible substrate in a pattern of discrete reservoirs. When the LLEC contacts an aqueous solution, the silver positive electrode (cathode) is reduced while the zinc negative electrode (anode) is oxidized. The LLEC used herein consisted of metals placed in proximity of about 1 mm to each other thus forming a redox couple and generating an ideal potential on the order of 1 Volt. The calculated values of the electric field from the LLEC were consistent with the magnitudes that are typically applied (1-10 V/cm) in classical electrotaxis experiments, suggesting that cell migration observed with the bioelectric dressing is likely due to electrotaxis.

Measurement of the potential difference between adjacent zinc and silver dots when the LLEC is in contact with de-ionized water yielded a value of about 0.2 Volts. Though the potential difference between zinc and silver dots can be measured, non-intrusive measurement of the electric field arising from contact between the LLEC and liquid medium was difficult. Keratinocyte migration was accelerated by exposure to an Ag/Zn LLEC. Replacing the Ag/Zn redox couple with Ag or Zn alone did not reproduce the effect of keratinocyte acceleration.

Exposing keratinocytes to an LLEC for 24 h significantly increased green fluorescence in the dichlorofluorescein (DCF) assay indicating generation of reactive oxygen species under the effect of the LLEC. To determine whether $H_2O_2$ is generated specifically, keratinocytes were cultured with an LLEC or placebo for 24 h and then loaded with PF6-AM (Peroxyfluor-6 acetoxymethyl ester; an indicator of endogenous $H_2O_2$). Greater intracellular fluorescence was observed in the LLEC keratinocytes compared to the cells grown with placebo. Over-expression of catalase (an enzyme that breaks down $H_2O_2$) attenuated the increased migration triggered by the LLEC. Treating keratinocytes with N-Acetyl Cysteine (which blocks oxidant-induced signaling) also failed to reproduce the increased migration observed with LLEC. Thus, $H_2O_2$ signaling mediated the increase of keratinocyte migration under the effect of the electrical stimulus.

External electrical stimulus can up-regulate the TCA (tricarboxylic acid) cycle. The stimulated TCA cycle is then expected to generate more NADH and $FADH_2$ to enter into the electron transport chain and elevate the mitochondrial membrane potential (Δm). Fluorescent dyes JC-1 and TMRM were used to measure mitochondrial membrane potential. JC-1 is a lipophilic dye which produces a red fluorescence with high Δm and green fluorescence when Δm is low. TMRM produces a red fluorescence proportional to Δm. Treatment of keratinocytes with LLEC for 24 h demonstrated significantly high red fluorescence with both JC-1 and TMRM, indicating an increase in mitochondrial membrane potential and energized mitochondria under the effect of the LLEC. As a potential consequence of a stimulated TCA cycle, available pyruvate (the primary substrate for the TCA cycle) is depleted resulting in an enhanced rate of glycolysis. This can lead to an increase in glucose uptake in order to push the glycolytic pathway forward. The rate of glucose uptake in HaCaT cells treated with LLEC was examined next. More than two fold enhancement of basal glucose uptake was observed after treatment with LLEC for 24 h as compared to placebo control.

Keratinocyte migration is known to involve phosphorylation of a number of receptor tyrosine kinases (RTKs). To determine which RTKs are activated as a result of LLEC, scratch assay was performed on keratinocytes treated with LLEC or placebo for 24 h. Samples were collected after 3 h and an antibody array that allows simultaneous assessment of the phosphorylation status of 42 RTKs was used to quantify RTK phosphorylation. It was determined that LLEC significantly induces IGF-1R phosphorylation. Sandwich ELISA using an antibody against phospho-IGF-1R and total IGF-1R verified this determination. As observed with the RTK array screening, potent induction in phosphorylation of IGF-1R was observed 3 h post scratch under the influence of LLEC. IGF-1R inhibitor attenuated the increased keratinocyte migration observed with LLEC treatment.

MBB (monobromobimane) alkylates thiol groups, displacing the bromine and adding a fluorescent tag (lamda emission=478 nm). MCB (monochlorobimane) reacts with only low molecular weight thiols such as glutathione. Fluorescence emission from UV laser-excited keratinocytes loaded with either MBB or MCB was determined for 30 min. Mean fluorescence collected from 10,000 cells showed a significant shift of MBB fluorescence emission from cells. No significant change in MCB fluorescence was observed, indicating a change in total protein thiol but not glutathione. HaCaT cells were treated with LLEC for 24 h followed by a scratch assay. Integrin expression was observed by immuno-cytochemistry at different time points. Higher integrin expression was observed 6 h post scratch at the migrating edge.

Consistent with evidence that cell migration requires $H_2O_2$ sensing, we determined that by blocking $H_2O_2$ signaling by decomposition of $H_2O_2$ by catalase or ROS scavenger, N-acetyl cysteine, the increase in LLEC-driven cell migration is prevented. The observation that the LLEC increases $H_2O_2$ production is significant because in addition to cell migration, hydrogen peroxide generated in the wound margin tissue is required to recruit neutrophils and other leukocytes to the wound, regulates monocyte function, and VEGF signaling pathway and tissue vascularization. Therefore, external electrical stimulation can be used as an effective strategy to deliver low levels of hydrogen peroxide over time to mimic the environment of the healing wound and thus should help improve wound outcomes. Another phenomenon observed during re-epithelialization is increased expression of the integrin subunit αv. There is evidence that integrin, a major extracellular matrix receptor, polarizes in response to applied ES and thus controls directional cell migration. It may be noted that there are a number of integrin subunits, however we chose integrin αv because of evidence of association of αv integrin with IGF-1R, modulation of IGF-1 receptor signaling, and of driving keratinocyte locomotion. Additionally, integrin$_{αv}$ has been reported to contain vicinal thiols that provide site for redox activation of function of these integrins and therefore the increase in protein thiols that we observe under the effect of ES may be the driving force behind increased integrin mediated cell migration. Other possible integrins which may be playing a role in LLEC-induced IGF-1R mediated keratinocyte migration are α5 integrin and α6 integrin.

Materials and Methods

Cell culture—Immortalized HaCaT human keratinocytes were grown in Dulbecco's low-glucose modified Eagle's medium (Life Technologies, Gaithersburg, Md., U.S.A.) supplemented with 10% fetal bovine serum, 100 U/ml penicillin, and 100 μg/ml streptomycin. The cells were maintained in a standard culture incubator with humidified air containing 5% $CO_2$ at 37° C.

Scratch assay—A cell migration assay was performed using culture inserts (IBIDI®, Verona, Wis.) according to the manufacturer's instructions. Cell migration was measured using time-lapse phase-contrast microscopy following withdrawal of the insert. Images were analyzed using the AxioVision Rel 4.8 software.

N-Acetyl Cysteine Treatment—Cells were pretreated with 5 mM of the thiol antioxidant N-acetylcysteine (Sigma) for 1 h before start of the scratch assay.

IGF-1R inhibition—When applicable, cells were preincubated with 50 nM IGF-1R inhibitor, picropodophyllin (Calbiochem, MA) just prior to the Scratch Assay.

Cellular $H_2O_2$ Analysis—To determine intracellular $H_2O_2$ levels, HaCaT cells were incubated with 5 pM PF6-AM in PBS for 20 min at room temperature. After loading, cells were washed twice to remove excess dye and visualized using a Zeiss Axiovert 200M microscope.

Catalase gene delivery—HaCaT cells were transfected with $2.3 \times 10^7$ pfu AdCatalase or with the empty vector as control in 750 μL of media. Subsequently, 750 μL of additional media was added 4 h later and the cells were incubated for 72 h.

RTK Phosphorylation Assay—Human Phospho-Receptor Tyrosine Kinase phosphorylation was measured using Phospho-RTK Array kit (R & D Systems).

ELISA—Phosphorylated and total IGF-1R were measured using a DuoSet IC ELISA kit from R&D Systems.

Determination of Mitochondrial Membrane Potential—Mitochondrial membrane potential was measured in HaCaT cells exposed to the LLEC or placebo using TMRM or JC-1 (MitoProbe JC-1 Assay Kit for Flow Cytometry, Life Technologies), per manufacturer's instructions for flow cytometry.

Integrin αV Expression—Human HaCaT cells were grown under the MCD or placebo and harvested 6 h after removing the IBIDI® insert. Staining was done using antibody against integrin αV (Abcam, Cambridge, Mass.).

Example 4

Wound Care Study

The medical histories of patients who received "standard-of-care" wound treatment ("SOC"; n=20), or treatment with an LLEC device as disclosed herein (n=18), were reviewed.

The wound care device used in the present study consisted of a discrete matrix of silver and zinc dots. A sustained voltage of approximately 0.8 V was generated between the dots. The electric field generated at the device surface was measured to be 0.2-1.0 V, 10-50 µA.

Wounds were assessed until closed or healed. The number of days to wound closure and the rate of wound volume reduction were compared. Patients treated with LLEC received one application of the device each week, or more frequently in the presence of excessive wound exudate, in conjunction with appropriate wound care management. The LLEC was kept moist by saturating with normal saline or conductive hydrogel. Adjunctive therapies (such as negative pressure wound therapy [NPWT], etc.) were administered with SOC or with the use of LLEC unless contraindicated. The SOC group received the standard of care appropriate to the wound, for example antimicrobial dressings, barrier creams, alginates, silver dressings, absorptive foam dressings, hydrogel, enzymatic debridement ointment, NPWT, etc. Etiology-specific care was administered on a case-by-case basis. Dressings were applied at weekly intervals or more. The SOC and LLEC groups did not differ significantly in gender, age, wound types or the length, width, and area of their wounds.

Wound dimensions were recorded at the beginning of the treatment, as well as interim and final patient visits. Wound dimensions, including length (L), width (W) and depth (D) were measured, with depth measured at the deepest point. Wound closure progression was also documented through digital photography. Determining the area of the wound was performed using the length and width measurements of the wound surface area.

Closure was defined as 100% epithelialization with visible effacement of the wound. Wounds were assessed 1 week post-closure to ensure continued progress toward healing during its maturation and remodeling phase.

Wound types included in this study were diverse in etiology and dimensions, thus the time to heal for wounds was distributed over a wide range (9-124 days for SOC, and 3-44 days for the LLEC group). Additionally, the patients often had multiple co-morbidities, including diabetes, renal disease, and hypertension. The average number of days to wound closure was 36.25 (SD=28.89) for the SOC group and 19.78 (SD=14.45) for the LLEC group, p=0.036. On average, the wounds in the LLEC treatment group attained closure 45.43% earlier than those in the SOC group.

Based on the volume calculated, some wounds improved persistently while others first increased in size before improving. The SOC and the LLEC groups were compared to each other in terms of the number of instances when the dimensions of the patient wounds increased (i.e., wound treatment outcome degraded). In the SOC group, 10 wounds (50% for n=20) became larger during at least one measurement interval, whereas 3 wounds (16.7% for n=18) became larger in the LLEC group (p=0.018). Overall, wounds in both groups responded positively. Response to treatment was observed to be slower during the initial phase, but was observed to improve as time progressed.

The LLEC wound treatment group demonstrated on average a 45.4% faster closure rate as compared to the SOC group. Wounds receiving SOC were more likely to follow a "waxing-and-waning" progression in wound closure compared to wounds in the LLEC treatment group.

Compared to localized SOC treatments for wounds, the LLEC (1) reduces wound closure time, (2) has a steeper wound closure trajectory, and (3) has a more robust wound healing trend with fewer incidence of increased wound dimensions during the course of healing.

Example 5

Induction of Pre-Angiogenic Responses in Vascular Endothelial Cells by Signaling Through VEGF Receptors Materials and Methods Cell Cultures and Reagents Tissue culture reagents were obtained from Life Technologies UK. The VEGFR inhibitor (catalog number 676475), the PI3K inhibitor LY294002 (catalog number 440202), the Akt inhibitor (catalog number 124005) and the Rho kinase inhibitor Y27632 (catalog number 688001) were all obtained from Calbiochem. Rhodamine-phalloidin (E3478) was obtained from Molecular Probes (Leiden, The Netherlands) and anti-tubulin conjugated with FITC was obtained from Sigma. The HUVEC cell line from ATCC was used prior to passage 10. Dulbecco's modified Eagle's medium (DMEM) with 10% fetal bovine serum (FBS) was used for culture cells and EF exposure experiments.

Electric Field Stimulation

HUVEC cells were seeded in a trough formed by two parallel (1 cm apart) strips of glass coverslip (No. 1, length of 22 mm) fixed to the base of the dish with silicone grease. Scratch lines were made perpendicular to the long axis of the chamber with a fine sterile needle and used as reference marks for directed cell migration. Cells were incubated for 24-48 hours (37° C., 5% $CO_2$) before a roof coverslip was applied and sealed with silicone grease. The final dimensions of the chamber, through which current was passed, were 22×10×0.2 mm. Agar-salt bridges not less than 15 cm long were used to connect silver/silver-chloride electrodes in beakers of Steinberg's solution (58 mM NaCl, 0.67 mM KCl, 0.44 mM $Ca(NO_3)_2$, 1.3 mM $MgSO_4$, 4.6 mM Trizma base, pH 7.8-8.0), to pools of excess culture medium at either side of the chamber. Field strengths were measured directly at the beginning of, the end of and during each experiment. No fluctuations in field strength were observed. For drug inhibition experiments, cells were incubated with the VEGFR inhibitor 4-[(4'-chloro-2'-fluoro)phenylamino]-6,7-dimethoxyquinazoline (50 µM), the PI3K inhibitor LY294002 (50 µM), an Akt inhibitor 1-L-6-hydroxymethyl-chiro-inositol 2-[(R)-2-O-methyl-3-O-octadecylcarbonate] (50 µM), the Rho kinase inhibitor Y27632 (50 µM), both Akt and Rho kinase inhibitors (10 µM each) or latrunculin (50 nM) for 1 hour before EF stimulation. The same concentration of drug was present during EF exposure in a $CO_2$ incubator.

Quantification of Cell Behavior

A series of images was taken with an image analyser immediately before EF exposure and at 4, 8 and 24 hours of EF exposure. Cell orientation was quantified as an orientation index (Oi), which is defined as Oi=cos 2(α), where a is the angle formed by the long axis of a cell with a line drawn perpendicular to the field lines. A cell with its long axis parallel to the vector of the EF will have an Oi of −1, and a cell with its long axis exactly perpendicular to the EF vector will have an Oi of +1. A randomly oriented population of cells will have an average Oi {defined as [$\Sigma_n$ cos 2(α)]÷n} of 0. The significance of this two-dimensional orientation distribution against randomness was calculated using Rayleigh's distribution. A long:short axis ratio was calculated for assessment of elongation.

Mean migration rate and directedness were quantified over 4 hours because cells multiplied during longer EF exposures, making it difficult to define a clear migration path. The angle (θ) that each cell moved with respect to the imposed EF vector was measured. The cos(θ) (directedness) is +1, if the cell moved directly along the field lines toward the cathode, 0 if the cell moved perpendicular to the EF vector and −1 if the cell moved directly towards the positive pole. Averaging the cosines $\{[\Sigma_i \cos(\theta)] \div N$, where N is the total number of cells$\}$ yields an average directedness of cell movement.

A commercially available VEGF165 ELISA kit was obtained from R and D (Minneapolis, Minn.), and the detailed technical instructions were followed. Confocal microscopy was as described. Statistical analyses were performed using unpaired, two-tailed Student's t-test. Data are expressed as mean±s.e.m.

Results

Cells cultured without exposure to the EF had the typical cobblestone morphology, with the long axis of the cell body oriented randomly. In contrast, endothelial cells cultured in DC EFs underwent a reorientation, with their long axis coming to lie perpendicular to the vector of the applied EF. This elongation and alignment in an applied EF resembles the response of endothelial cells to fluid shear stress.

Cell alignment was quantified using an orientation index Oi=cos 2(a), where a is the angle formed between the long axis of a cell and a line drawn perpendicular to the field lines. In cells oriented perpendicular to the field vector, the Oi is +1, cells parallel to the field vector give an Oi of −1 and random orientation gives an Oi of 0. We compared the elongation and reorientation of single cells with those of cells in monolayers. They were broadly similar, with single cells responding quicker and showing a significantly higher Oi (0.56±0.04, n=245) at 4 hours of EF exposure than cells in a monolayer sheet (0.35±0.03, n=528). Both single cells and cells in monolayers, however, had a similar Oi by 8 hours (0.71±0.03, n=227 and 0.62±0.03, n=312, respectively).

The perpendicular orientation of endothelial cells showed both time and voltage dependency. Significant orientation was observed as early as 4 hours after the onset of the EF. A steady increase of Oi indicates gradually increasing perpendicular orientation with continued exposure. Longer EF exposure, up to 3 days at 100 mV mm$^{-1}$ (1 mV across a cell 10 μm wide), induced striking orientation and elongation. EF exposure did not induce any detrimental effects on the cells, which were perfectly healthy for up to 3-4 days in EFs.

Voltage dependency was more obvious at later times, with a higher Oi for cells cultured at higher voltages. After 24 hours at 300 mV mm$^{-1}$, almost all the cells were perpendicular. An EF strength as low as 75 mV mm$^{-1}$ induced significant perpendicular orientation, with Oi of 0.19 (significantly different from random orientation, $p=4.4 \times 10^{-6}$, n=433), whereas an EF of 50 mV mm$^{-1}$ did not. The threshold field strength inducing perpendicular orientation of the endothelial cells was therefore between 50 mV mm$^{-1}$ and 75 mV mm$^{-1}$. This is low, representing only 0.5-0.75 mV across a cell with a diameter of 10 μm.

Reorientation of Endothelial Cells in EFs Requires VEGFR Activation

VEGF activation is a pivotal element in angiogenic responses and enhanced angiogenesis by electric stimulation in vivo is mediated through VEGFR activation. To test whether EF-induced endothelial cell orientation might involve VEGF signaling, we quantified levels of VEGF. EF exposure (200 mV mm$^{-1}$, the same as that measured at skin wounds) significantly enhanced levels of VEGF released into the culture medium. Marked elevation of VEGF in the culture medium was observed as early as 5 minutes after onset of the EF; this was reduced at 1 hour and 2 hours, rose again at 4 hours, and reached a high level by 24 hours.

Inhibition of VEGFR activation by inhibiting both VEGFR-1 and VEGFR-2 with the drug 4-[(4'-chloro-2'-fluoro)phenylamino]-6,7-dimethoxyquinazoline completely abolished the reorientation of cells in an EF. This drug is a potent VEGFR inhibitor that inhibits the receptor tyrosine kinase activity (50% inhibitory concentrations of 2.0 μM and 100 nM for VEGFR-1 and VEGFR-2, respectively). It is very selective for VEGFR-1 and VEGFR-2 tyrosine kinase activity compared with that associated with the epidermal growth factor (EGF) receptor (50-fold and 3800-fold, respectively). The morphology of the cells treated with VEGFR inhibitor was very similar to control cells. Cells still elongated, although their long axis was slightly reduced, but they were oriented randomly. Inhibition of VEGFRs could conceivably have had detrimental effects on the long-term viability of cells and this could have influenced their orientation responses. To test for this, we compared the orientation response after a short period of inhibitor and EF application. The orientation response was completely abolished at 4 hours and 8 hours in an EF after VEGFR inhibition. The Oi values of the cells treated with VEGFR inhibitor were −0.16±0.05 and −0.05±0.05 in EF for 4 hours and 8 hours, respectively, which is significantly different from the non-inhibitor-treated values of 0.36±0.05 and 0.53±0.05 (P<0.01).

Reorientation of Endothelial Cells Involved the PI3K-Akt Pathway

VEGFR activation lead to endothelial cell migration, cell survival and proliferation, which require the activation of Akt, a downstream effectors of PI3K. Both the PI3K inhibitor LY294002 (50 μM) and the Akt inhibitor (50 μM) significantly decreased the orientation response.

The concentration of either drug alone would be expected to inhibit PI3K and Akt activation completely but neither drug inhibited perpendicular reorientation completely, and significant Oi values remained, indicating that other signaling mechanisms must be involved.

Role of Rho and Integrin in EF-Induced Reorientation of Endothelial Cells

The Rho family of GTPases regulates VEGF-stimulated endothelial cell motility and reorganization of the actin cytoskeleton, which are important in endothelial cell retraction and in the formation of intercellular gaps. The Rho kinase inhibitor, Y27632, decreased the orientation response significantly, with Oi values of 0.55±0.05, 0.45±0.05 and 0.24±0.05 at 10 μM, 20 μM and 50 μM, respectively. Significant Oi values nonetheless remained even at 50 μM, indicating that multiple signaling mechanisms must be involved. Mitogen-activated-protein kinase inhibition with U0126 (50 μM), like Y27632 (0.33±0.03), decreased the orientation to a similar extent.

Because both Akt and Rho kinase inhibitors individually showed partial inhibition, perhaps the two enzymes function in different pathways to induce cell reorientation. To test this, a combination of the two inhibitors was used. The orientation response was abolished completely by using Akt and Rho kinase inhibitors together (both at 10 μM) (Oi=−0.10±0.06; compared to control=0.80±0.09, P<0.0001).

Integrins, especially αvβ3, are important in endothelial cell movement and alignment to shear stress and mechanical stimulation. HUVEC cells were incubated with a blocking antibody against αvβ3 (LM609) (20 μg ml$^{-1}$) for 1 hour and then exposed to an EF (200 mV mm$^{-1}$) with the antibody present. Blocking αvβ3 had no effect on orientation to the EF, cells reoriented normally (Oi=0.72±0.03, n=110, compared with the control=0.80±0.09, n=124, P>0.05).

Small EFs Elongated Endothelial Cells

HUVEC cells elongated dramatically in an EF. By contrast, cells cultured with no EF retained a more-cobblestone-like appearance. Striking cell elongation was induced by a voltage drop of about 0.7-4.0 mV across a cell of ~15 μm in diameter. We quantified the elongation of the cells using a long:short axis ratio. A perfectly round cell has a long:short axis ratio of 1 and, as cells elongate, the ratio increases. Control cells (no EF) showed no increase in long:short axis over 24 hours in culture. Elongation responses were both time and voltage dependent. The long:short axis ratio of EF exposed cells indicated gradual cell elongation throughout the 24 hour experimental period. The voltage dependency of the elongation response was more obvious at later times, with a greater long:short axis ratio for cells cultured at higher EFs. The threshold for EF-induced endothelial cell elongation was between 50-75 mV mm$^{-1}$, again 0.5-0.75 mV across a cell 10 μm in diameter. The elongation response of endothelial cells was more marked than that seen previously at the same EF strengths, in corneal and lens epithelial cells.

VEGFR, PI3K-Akt and Rho Signaling are Involved in the Elongation Response

The signaling elements required for reorientation are also involved in elongation, but there are subtle differences. The VEGFR inhibitor (50 μM) had no effect on the long:short axis ratio of control cells but significantly decreased the long:short axis ratio in EF-treated cells (P<0.002). Both the PI3K inhibitor LY294002 and the Akt inhibitor also significantly decreased the long:short axis ratio (both P<0.0001 versus control). Cells treated with these drugs elongated less, with LY294002 the more effective in suppressing EF-induced elongation. The Rho kinase inhibitor, Y27632 also significantly decreased the long:short axis ratio (P<0.0001), whereas the αvδ3-blocking antibody significantly inhibited the elongation response (3.12±0.008 compared with the control 3.65±0.15, P=0.007).

Cytoskeleton Alignment and the Consequence of Actin Filament Disruption

To control changes in cell shape, reorientation and migration, extracellular stimuli initiate intracellular signaling that modifies cytoskeletal organization. Both actin filaments and microtubules were aligned in the direction of cell elongation. Latrunculin A, a toxin inhibiting actin polymerization, completely abolished the EF-induced elongation response and suppressed the orientation response significantly (P<0.001) but not fully.

Small EFs Direct Migration of Endothelial Cells Towards the Anode

Endothelial cells migrated directionally toward the anode when cultured in EFs. The directional migration was slow but steady during the EF exposure and was more evident for single cells than for sheets of cells. Cells migrated directionally towards the anode while elongating and reorienting perpendicularly. Lamellipodial extension toward the anode was marked. Directional migration was obvious at a physiological EF strength of 100 mV mm$^{-1}$. The threshold field strength that could induce directional migration was therefore below 100 mV mm$^{-1}$. Cell migration was quantified as previously and significant anodal migration was evident (P<0.0001). Migration speed, however, remained constant before and after EF exposure, at 1-2 μm hour$^{-1}$, which is significantly slower than most other cell types migrating in an EF.

Example 6

Effect on *Propionibacterium acnes*

Bacterial Strains and Culture

The main bacterial strain used in this study is *Propionibacterium acnes* and multiple antibiotics-resistant *P. acnes* isolates are to be evaluated.

ATCC medium (7 *Actinomyces* broth) (BD) and/or ATCC medium (593 chopped meat medium) is used for culturing *P. acnes* under an anaerobic condition at 37° C. All experiments are performed under anaerobic conditions.

Culture

LNA (Leeming-Notman agar) medium is prepared and cultured at 34° C. for 14 days.

Planktonic Cells

*P. acnes* is a relatively slow-growing, typically aerotolerant anaerobic, Gram-positive bacterium (rod). *P. acnes* is cultured under anaerobic condition to determine for efficacy of an embodiment disclosed herein (PROCELLERA®). Overnight bacterial cultures are diluted with fresh culture medium supplemented with 0.1% sodium thioglycolate in PBS to 10$^5$ colony forming units (CFUs). Next, the bacterial suspensions (0.5 mL of about 105) are applied directly on PROCELLERA® (2"×2") and control fabrics in Petri-dishes under anaerobic conditions. After 0 h and 24 h post treatments at 37° C., portions of the sample fabrics are placed into anaerobic diluents and vigorously shaken by vortexing for 2 min. The suspensions are diluted serially and plated onto anaerobic plates under an anaerobic condition. After 24 h incubation, the surviving colonies are counted.

Bacterial Biofilms in Skin Infections

It is generally accepted that many human infections are biofilm-related and that sessile (biofilm-grown) cells are highly resistant against antimicrobial agents. It has been suggested that *P. acnes* cells residing within the follicles grow as a biofilm. *P. acnes* readily forms biofilms in vitro as well as on various medical devices in vivo, combined with the high resistance of sessile *P. acnes* cells and the increased production of particular virulence factors.

Example 7

Modulation of Bacterial Gene Expression and Enzyme Activity

Treatment of biofilms presents a major challenge, because bacteria living within them enjoy increased protection against host immune responses and are markedly more tolerant to antibiotics. Bacteria residing within biofilms are encapsulated in an extracellular matrix, consisting of several components including polysaccharides, proteins and DNA which acts as a diffusion barrier between embedded bacteria and the environment thus retarding penetration of antibacterial agents. Additionally, due to limited nutrient accessibility, the biofilm-residing bacteria are in a physiological state of low metabolism and dormancy increasing their resistance towards antibiotic agents.

Chronic wounds present an increasing socio-economic problem and an estimated 1-2% of western population suffers from chronic ulcers and approximately 2-4% of the national healthcare budget in developed countries is spent on treatment and complications due to chronic wounds. The incidence of non-healing wounds is expected to rise as a natural consequence of longer lifespan and progressive changes in lifestyle like obesity, diabetes, and cardiovascular disease. Non-healing skin ulcers are often infected by biofilms. Multiple bacterial species reside in chronic wounds; with *Pseudomonas aeruginosa*, especially in larger wounds, being the most common. *P. aeruginosa* is suspected to delay healing of leg ulcers. Also, surgical success with split graft skin transplantation and overall healing rate of chronic venous ulcers is presumably reduced when there is clinical infection by *P. aeruginosa*.

*P. aeruginosa* biofilm is often associated with chronic wound infection. The BED ("BED" or "bioelectric device" or PROCELLERA® as disclosed herein) consists of a matrix of silver-zinc coupled biocompatible microcells, which in the presence of conductive wound exudate activates to generate an electric field (0.3-0.9V). Growth (measured as O.D and cfu) of pathogenic *Pseudomonas aeruginosa* strain PAO1 in LB media was markedly arrested in the presence of the BED ($p<0.05$, $n=4$). PAO1 biofilm was developed in vitro using a polycarbonate filter model. Grown overnight in LB medium at 37° C. bacteria were cultured on sterile polycarbonate membrane filters placed on LB agar plates and allowed to form a mature biofilm for 48 h. The biofilm was then exposed to BED or placebo for the following 24 h. Structural characterization using scanning electron microscopy demonstrated that the BED markedly disrupted biofilm integrity as compared to no significant effect observed using a commercial silver dressing commonly used for wound care. Staining of extracellular polymeric substance, PAO1 staining, and a vital stain demonstrated a decrease in biofilm thickness and number of live bacterial cells in the presence of BED ($n=4$). BED repressed the expression of quorum sensing genes lasR and rhlR ($p<0.05$, $n=3$). BED was also found to generate micromolar amounts of superoxide ($n=3$), which are known reductants and repress genes of the redox sensing multidrug efflux system mexAB and mexEF ($n=3$, $p<0.05$). BED also down-regulated the activity of glycerol-3-phosphate dehydrogenase, an electric field sensitive enzyme responsible for bacterial respiration, glycolysis, and phospholipid biosynthesis ($p<0.05$, $n=3$).

Materials and Methods

In-Vitro Biofilm Model

PAO1 biofilm was developed in vitro using a polycarbonate filter model. Cells were grown overnight in LB medium at 37° C. bacteria were cultured on sterile polycarbonate membrane filters placed on LB agar plates and allowed to form a mature biofilm for 48 h. The biofilm was then exposed to BED or placebo for the following 24 h.

Energy Dispersive X-Ray Spectroscopy (EDS)

EDS elemental analysis of the Ag/ZN BED was performed in an environmental scanning electron microscope (ESEM, FEI XL-30) at 25 kV. A thin layer of carbon was evaporated onto the surface of the dressing to increase the conductivity.

Scanning Electron Microscopy

Biofilm was grown on circular membranes and was then fixed in a 4% formaldehyde/2% glutaraldehyde solution for 48 hours at 4° C., washed with phosphate-buffered saline solution buffer, dehydrated in a graded ethanol series, critical point dried, and mounted on an aluminum stub. The samples were then sputter coated with platinum (Pt) and imaged with the SEM operating at 5 kV in the secondary electron mode (XL 30S; FEG, FEI Co., Hillsboro, Oreg.).

Live/Dead Staining

The LIVE/DEAD BacLight Bacterial Viability Kit for microscopy and quantitative assays was used to monitor the viability of bacterial populations. Cells with a compromised membrane that are considered to be dead or dying stain red, whereas cells with an intact membrane stain green.

EPR Spectroscopy

EPR measurements were performed at room temperature using a Bruker ER 300 EPR spectrometer operating at X-band with a TM 110 cavity. The microwave frequency was measured with an EIP Model 575 source-locking microwave counter (EIP Microwave, Inc., San Jose, Calif.). The instrument settings used in the spin trapping experiments were as follows: modulation amplitude, 0.32 G; time constant, 0.16 s; scan time, 60 s; modulation frequency, 100 kHz; microwave power, 20 mW; microwave frequency, 9.76 GHz. The samples were placed in a quartz EPR flat cell, and spectra were recorded at ambient temperature (25° C.). Serial 1-min EPR acquisitions were performed. The components of the spectra were identified, simulated, and quantitated as reported. The double integrals of DEPMPO experimental spectra were compared with those of a 1 mM TEMPO sample measured under identical settings to estimate the concentration of superoxide adduct.

Quantification of mRNA and miRNA Expression

Total RNA, including the miRNA fraction, was isolated using Norgen RNA isolation kit, according to the manufacturer's protocol. Gene expression levels were quantified with real-time PCR system and SYBR Green (Applied Biosystems) and normalized to nadB and proC as housekeeping genes. Expression levels were quantified employing the 2 ($-\Delta\Delta ct$) relative quantification method.

Glycerol-3-Phosphate Dehydrogenase Assay

The glycerol-3-phosphate dehydrogenase assay was performed using an assay kit from Biovision, Inc. following manufacturer's instructions. Briefly, cells ($\sim 1\times 10^6$) were homogenized with 200 µl ice cold GPDH Assay buffer for 10 minutes on ice and the supernatant was used to measure O.D. and GPDH activity calculated from the results.

Statistics

Control and treated samples were compared by paired t test. Student's t test was used for all other comparison of difference between means. $P<0.05$ was considered significant.

Ag/Zn BED Disrupts *P. aeruginosa* Biofilm

To validate the chemical composition of the dressing, we collected high resolution electron micrographs using an environmental scanning electron microscope. Our element maps indicate that silver particles are concentrated in the golden dots of the polyester cloth, while zinc particles are concentrated in the grey dots.

Figure 14A:
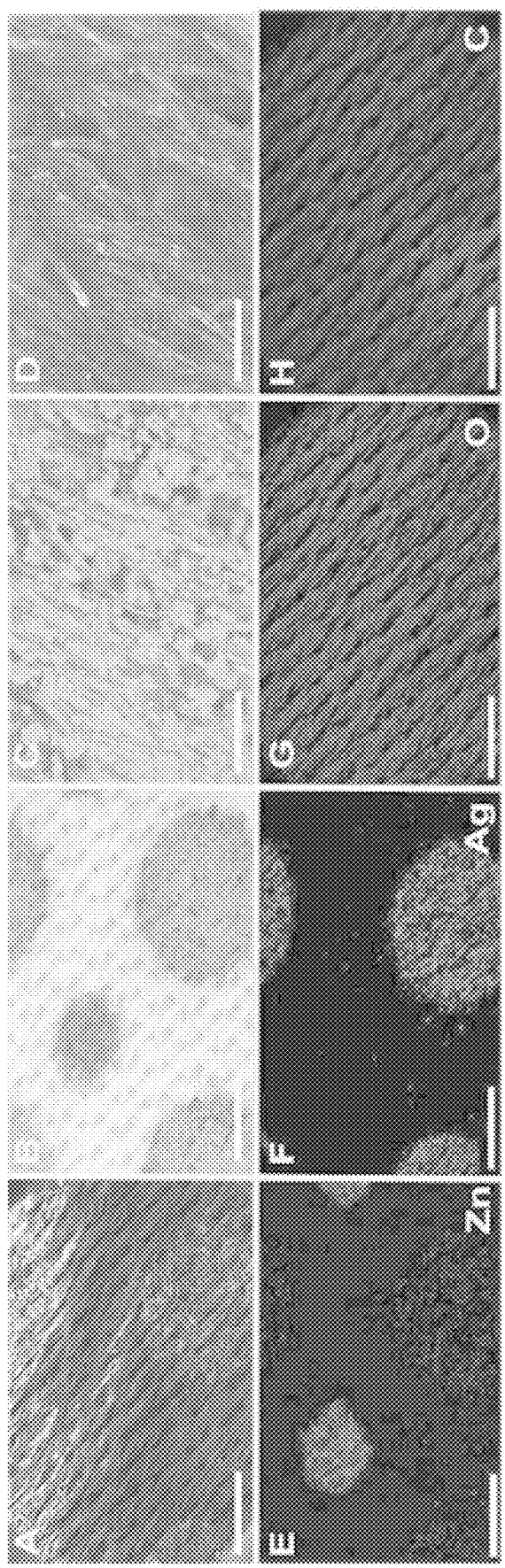
FIG. 14(A) is an Energy Dispersive X-ray Spectroscopy (EDS) analysis of Ag/Zn BED ("bioelectric device" refers to an embodiment as disclosed herein).
  a. Scanning Electron Microscope (SEM) image;
  b. Light Microscope Image;
  c. Closer view of a golden dot and a grey dot in B respectively.
  d. Closer view of a golden dot and a grey dot in B respectively.
  e. EDS element map of zinc;
  f. EDS element map of silver;
  g. EDS element map of oxygen.
Figure 14B:
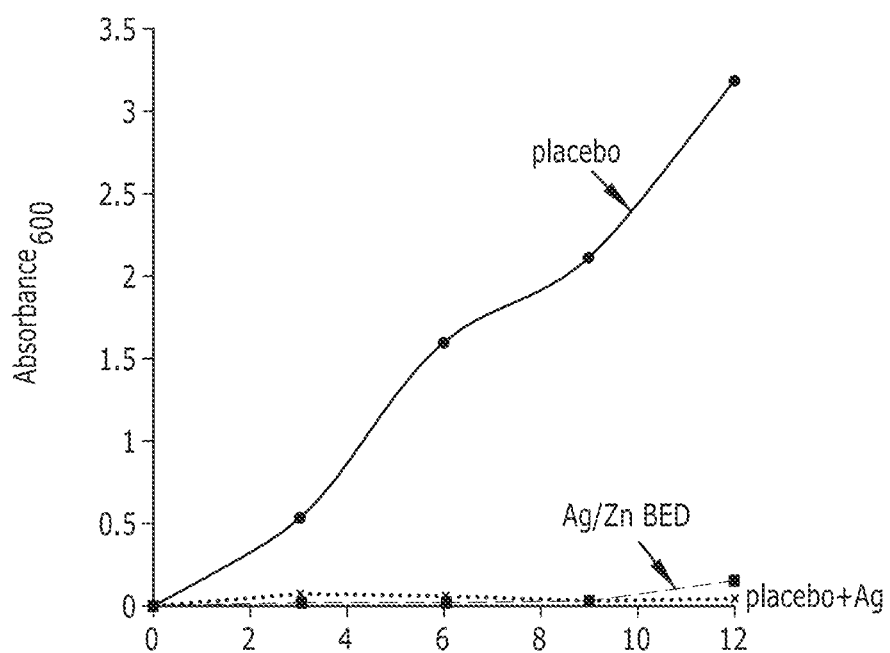
Figure 14C:
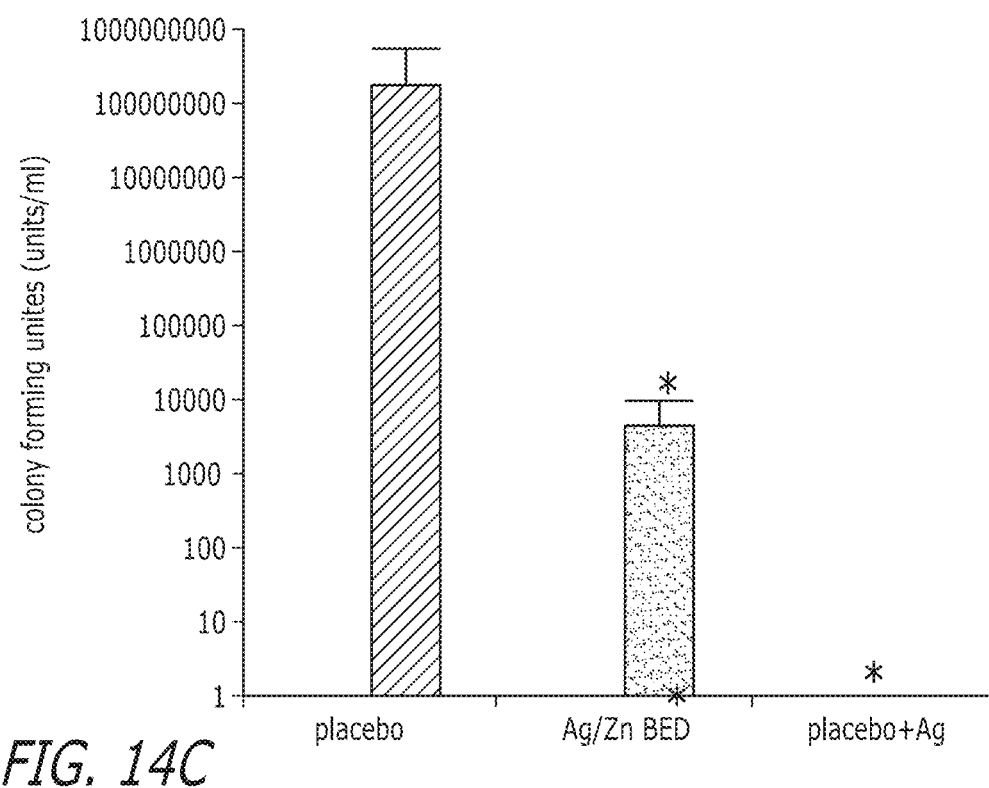
Figure 14D:
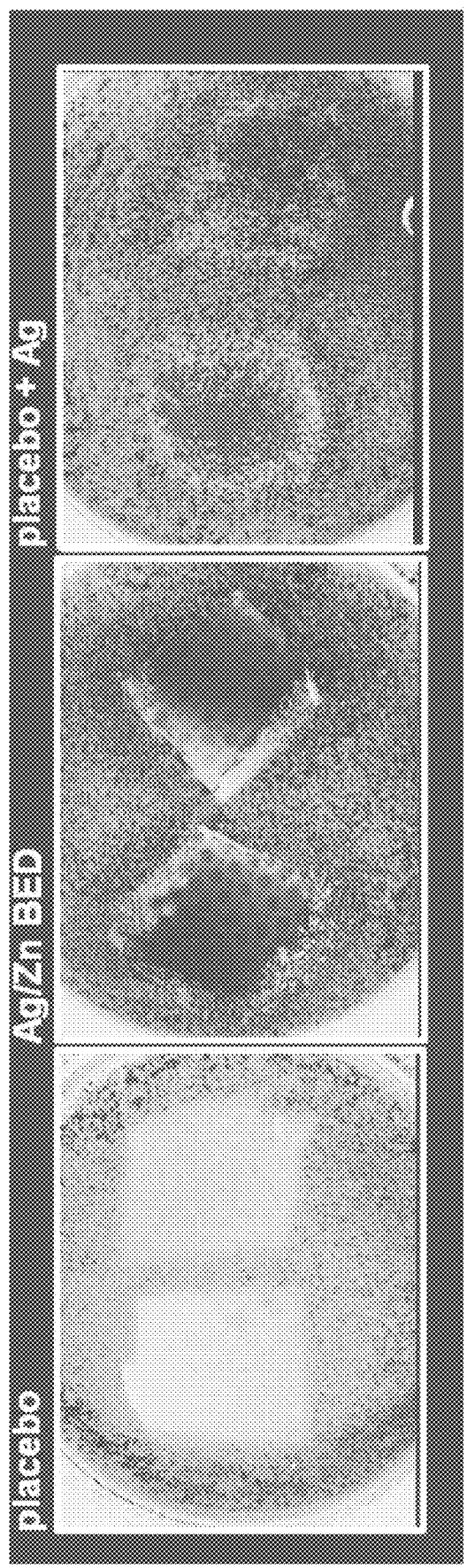

As illustrated in FIG. 14A, *P. aeruginosa* was grown in round bottom tubes in LB medium with continuous shaking and absorbance was measured by calculating optical density at 600 nm at different time points. It was observed that Ag/Zn BED and the control dressing with equal amount of silver inhibited bacterial growth ($n=4$) (FIG. 14B,C). When bacteria is grown in an agar plate with Ag/Zn BED dressing or placebo embedded in the agar, the zone of inhibition is clearly visible in the case of Ag/Zn BED thus demonstrating its bacteriostatic property, while placebo with silver dressing showed a smaller zone of inhibition, indicating the effect role of electric field as compared to topical contact. (FIG. 14D). However, as evident from scanning electron microscope images (FIG. 15); EPS staining (FIG. 16); and live/dead staining (FIG. 17), Ag/Zn BED disrupts biofilm much better while silver does not have any effect on biofilm disruption. Silver has been recognized for its antimicrobial properties for centuries. Most studies on the antibacterial efficacy of silver, with particular emphasis on wound healing, have been performed on planktonic bacteria. Silver ions, bind to and react with proteins and enzymes, thereby causing structural changes in the bacterial cell wall and membranes, leading to cellular disintegration and death of the bacterium. Silver also binds to bacterial DNA and RNA, thereby inhibiting the basal life processes.

Silver is effective against mature biofilms of *P. aeruginosa*, but only at a high silver concentration. A concentration of 5-10 µg/mL silver sulfadiazine has been reported to eradicate biofilm whereas a lower concentration (1 µg/mL) had no effect. Therefore, the concentration of silver in currently available wound dressings is much too low for treatment of chronic biofilm wounds. FIG. 18 shows PAO1 staining of the biofilm demonstrating the lack of elevated mushroom like structures in the Ag/Zn BED treated sample.

Ag/Zn BED Down-Regulates Quorum Sensing Genes

The pathogenicity of *P. aeruginosa* is attributable to an arsenal of virulence factors. The production of many of these extracellular virulence factors occurs only when the bacterial cell density has reached a threshold (quorum). Quorum sensing is controlled primarily by two cell-to-cell signaling systems, called las and rhl, which are both composed of a transcriptional regulator (LasR and RhlR, respectively) and an autoinducer synthase (LasI and RhlI, respectively). In *P. aeruginosa*, LasI produces 3OC12-HSL. LasR, then, responds to this signal and the LasR:3OC12-HSL complex activates transcription of many genes including rhlR, which encodes a second quorum sensing receptor, RhlR which binds to autoinducer C4-HSL produced by RhlI. RhlR:C4-HSL also directs a large regulon of genes. *P. aeruginosa* defective in QS is compromised in their ability to form biofilms. Quorum sensing inhibitors increase the susceptibility of the biofilms to multiple types of antibiotics.

To test the effect of the electric field on quorum sensing genes, we subjected the mature biofilm to the Ag/Zen BED or placebo for 12 hours and looked at gene expression levels. We selected an earlier time point, because by 24 hours, as in earlier experiments, most bacteria under Ag/Zn BED treatment were dead. We found a significant down regulation of lasR and rhlR (n=4, p<0.05). lasR transcription has been reported to weakly correlate with the transcription of lasA, lasB, toxA and aprA. We did not, however, find any significant difference in their expression levels at this time point, although we found them down regulated in the Ag/Zn BED treated samples at the 24 hour time point (data not shown). (FIG. 19).

Ag/Zn BED Represses the Redox Sensing Multidrug Efflux System in *P. aeruginosa*

Ag/Zn BED acts as a reducing agent and reduces protein thiols. One electron reduction of dioxygen $O_2$, results in the production of superoxide anion. Molecular oxygen (dioxygen) contains two unpaired electrons. The addition of a second electron fills one of its two degenerate molecular orbitals, generating a charged ionic species with single unpaired electrons that exhibit paramagnetism. Superoxide anion, which can act as a biological reductant and can reduce disulfide bonds, is finally converted to hydrogen peroxide is known to have bactericidal properties. Here, we used electron paramagnetic resonance (EPR) to detect superoxide directly upon exposure to the bioelectric dressing. Superoxide spin trap was carried out using DEPMPO (2-(diethoxyphosphoryl)-2-methyl-3,4-dihydro-2H-pyrrole 1-oxide) and ~1 µM superoxide anion production was detected upon 40 mins of exposure to Ag/Zn BED (FIG. 20). MexR and MexT are two multidrug efflux regulators in *P. aeruginosa* which uses an oxidation-sensing mechanism. Oxidation of both MexR and MexT results in formation of intermolecular disulfide bonds, which activates them, leading to dissociation from promoter DNA and de-repression of MexAB-oprM and MexEF-oprN respectively, while in a reduced state, they do not transcribe the operons. Induction of Mex operons leads not only to increased antibiotic resistance but also to repression of the quorum sensing cascades and several virulence factors. We observe down-regulation of the downstream Mex genes MexA, MexB, MexE and MexF (but not MexC and MexD) (n=4, p<0.05), in Ag/Zn BED treated samples, inactive forms of MexR and MexT in their reduced states. To confirm the reducing activity of the Ag/Zn BED, the experiments were repeated with 10 mM DTT and similar results were observed. (FIG. 21).

Ag/Zn BED Diminishes Glycerol-3-Phosphate Dehydrogenase Enzyme Activity

Electric fields can affect molecular charge distributions on many enzymes. Glycerol-3-phosphate dehydrogenase is an enzyme involved in respiration, glycolysis, and phospholipid biosynthesis and is expected to be influenced by external electric fields in *P. aeruginosa*. We observed significantly diminished glycerol-3-phosphate dehydrogenase enzyme activity by treating *P. aeruginosa* biofilm to the Ag/Zn BED for 12 hours (n=3). (FIG. 22).

Example 8

LLEC Influence on Biofilm Properties

In this study ten clinical wound pathogens associated with chronic wound infections were used for evaluating the anti-biofilm properties of an LLEC. Hydrogel and drip-flow reactor (DFR) biofilm models were employed for the efficacy evaluation of the wound dressing in inhibiting biofilms. Biofilms formed with *Acinetobacter baumannii, Corynebacterium amycolatum, Escherichia coli, Enterobacter aerogenes, Enterococcus faecalis* CI 4413, *Klebsiella pneumonia, Pseudomonas aeruginosa, Serratia marcescens, Staphylococcus aureus*, and *Streptococcus equi* clinical isolates were evaluated. For antimicrobial susceptibility testing of biofilms, $10^5$ CFU/mL bacteria was used in both biofilm models. For poloxamer hydrogel model, the LLECs (25 mm diameter) were applied directly onto the bacterial biofilm developed onto 30% poloxamer hydrogel and Muller-Hinton agar plates, and incubated at 37° C. for 24 h to observe any growth inhibition. In the DFR biofilm model, bacteria were deposited onto polycarbonate membrane as abiotic surface, and sample dressings were applied onto the membrane. The DFR biofilm was incubated in diluted trypticase soy broth (TSB) at room temperature for 72 h. Biofilm formations were evaluated by crystal violet staining under light microscopy, and anti-biofilm efficacy was demonstrated by reduction in bacterial numbers.

Example 9

Modulation of Mammalian Gene Expression and Enzyme Activity

Grown overnight in LB medium at 37° C., primary human dermal fibroblasts are cultured on sterile polycarbonate membrane filters placed on LB agar plates for 48 h. The cells are then exposed to BED or placebo for the following 24 h. BED represses the expression of glyceraldehyde 3-phosphate dehydrogenase. BED also down-regulates the activity of glyceraldehyde 3-phosphate dehydrogenase.

Example 10

Modulation of Insect Gene Expression and Enzyme Activity

Grown overnight in LB medium at 37° C., *drosophila* S2 cells are cultured on sterile polycarbonate membrane filters placed on LB agar plates for 48 h. The cells are then exposed to BED or placebo for the following 24 h. BED represses the expression of insect P450 enzymes. BED also down-regulates the activity of insect P450 enzymes.

Example 11

Effect on *Propionibacterium acnes*

To determine the antimicrobial properties of the devices as disclosed herein, assessment of antibacterial finishes on textile materials was conducted in accordance with the American Association of Textile Chemists and Colorists (AATCC) Testing Methodology 100-1993. The microcurrent generating dressings were tested against multiple pathogens and successfully demonstrated antimicrobial properties against a broad spectrum of pathogens as shown in Table 1 below.

TABLE 1

In-vitro Percent Reduction in Microorganisms

| Microorganism | % Reduction |
| --- | --- |
| *Escherichia coli* | 99.99 |
| *Aspergillus niger* | 99.27 |
| *Trichophyton mentagropytes* | 99.22 |
| Vancomycin Resistant *Enterococcus* (VRE) | 99.97 |
| *Streptococcus pneumoniae* | 100 |
| Methicillin Resistant *Staph Aureus* (MSRA) | 100 |
| *Staphylococcus aureus* | 100 |
| *Acinetobacter baumaanii* | 100 |
| *Trichophyton rubrum* | 99.99 |
| *Corynebacterium xerosis* | 100 |
| *Trichophyton ashii/inkin* | 99.97 |
| *Pseudomonas aeruginosa* | 100 |
| *Candida albicans* | 99.98 |
| *Propionibacterium acnes* | 100 |
| *Klebsiella Pneumonaie* | 100 |
| Herpes Simplex Type 1 | 100 |
| *Varicella Virus* | 99.98 |

Further studies will be performed as described:
Outcome Measures
Primary outcomes: Change in acne severity grade from baseline and split-back comparison as determined by Leeds Acne Grading System11 and blinded clinician extender evaluation. Change in acne severity based on masked photographic assessment
Secondary outcomes: Patient subjective outcomes, per user assessment survey. Patient assessment of wearability of study device
Study Design
This is a double-blinded, two-arm, same-patient, split-back, prospective study investigating 50 patients presenting with acne vulgaris on the back; Patients will serve as their own controls and wear a vest as described herein comprising a substrate with biocompatible electrodes configured to generate an electric field, or in the presence of a conductive solution, an electric current.

Study Site: This multicenter study will be conducted at two facilities; Paradise Valley Dermatology, Phoenix, Ariz. and Arizona Advanced Dermatology, Phoenix/Gilbert, Ariz.

Selection of Patients: The study population will include subjects age 14 years 40 years.

Number of Patients: 50 subjects completing up to at least week 6 of treatment will be considered evaluable. Subject population will include male or female subjects of all ethnic groups. Parental consent for treatment of minors will be obtained for subjects <18 years.

Inclusion Criteria:
a. Clinical diagnosis of mild or moderate acne vulgaris of the back (Leeds scale grades 1-5)
b. Subjects age ≥14 years ≤40 years
c. Participants willing to undergo treatment and participate in follow up evaluations. Participants willing to comply with study procedures and willing to refrain from "picking" at lesions.
d. Participants with cell phones and willing to receive daily text reminders to wear study device.
e. Participants falling outside the washout periods for topical and systemic treatments and office procedures.
f. 4 weeks for topical agents on the back (corticosteroids, retinoids and other acne treatments);
g. 8 weeks for office-based acne procedures on the back (for chemical peeling, laser and light-based therapies).
h. 12 weeks for systemic drugs (corticosteroids and other acne treatments)
i. Subjects requiring topical agents for the face or requiring office-based acne procedures for the face will be included in the study.
j. Participant must be able to read and understand informed consent, and signs the informed consent Exclusion Criteria
a. Clinical diagnosis of severe acne vulgaris of the back requiring systemic drugs for management, as defined by Leeds Scale Grades ≥6
b. Less than 14 years of age or over 40 years of age.
c. Patients receiving any topical or office-based acne procedures within the washout period prior to study.
d. Participation in another clinical trial that involved the use of an investigational drug or device that in the opinion of the investigator would confound the results of this trial
e. Individuals with silver or zinc sensitivity
f. Active cancer
g. Immunosuppressive treatment
h. Clinically diagnosed hyperandrogenic state
i. Evidence of severe androgen excess (i.e., testosterone levels >150 ng/dL)
j. Excessive back hair in male patients
k. Pregnant or nursing individuals
l. Patients with pacemakers
m. Cystic or nodular acne lesions
n. Use of medicated shampoos, body washes, exfoliants and benzyl peroxide washes for 4 weeks prior to study start.
o. Any other medical condition in the clinician's opinion that excludes the patient.
p. Geographical concerns (residence not within reasonable travel distance) that would hamper compliance with required study visits.
q. The Investigator believes that the subject will be unwilling or unable to comply with study protocol requirements, including application of study device and all study-related follow up visit requirements.

The participants must answer "yes" on all inclusion criteria and must answer "no" on all exclusion criteria Patient Recruitment Patients treated at Paradise Valley Dermatology, Arizona Advanced Dermatology, Center for Dermatology, and the Skin and Cancer Center of AZ presented with acne vulgaris of the back will be given the opportunity to enroll into the study. At time of screening, the physician extender will document non-identifiers including date, sex, age, presence of back acne, and interest in participation in a study. If there is an interest, the patients will be given a detailed explanation of the risks and benefits of the study.

Method of Obtaining Informed Consent

Written informed consent will be obtained from the patients by the physicians, residents and/or staff present in the clinic who are treating the individual patients Plan of Study The system to be used in the present study is a 2-part vest designed to cover the scapular area of the back. The outer vest is comprised of vinyl, polyester trim and elastic materials and adjustable straps. The vest contains a detachable absorbent pad comprised of polyvinyl acetate (PVA) lined with the multi-array matrix of biocompatible microcells printed on one half of the vest, and a placebo pattern on the other half of the vest Description of Study Procedures Randomization Patients will be randomized into Group X or Group Y. 25 patients will be randomized to receive vests with the multi-array matrix of biocompatible microcells printed on the right half and placebo pattern on the left half (Group X) and 25 patients will receive vests with multi-array matrix of biocompatible microcells printed on the left half and placebo on the right half (Group Y). The patient, investigators and physician extenders (nurses, PA's, etc) will be blinded to the assigned side of the vest. Just prior to dissemination of study materials, the investigator will be provided with the randomization of treatment the participant will receive in the duration of the study, Group X or Group Y. A randomization key will be held at a secure location with the study sponsor. After final study analysis, the key will be revealed. In the event the randomization is made apparent, a note will be documented in the patient file. Patient will still be included in the study and study data will still be considered evaluable.

Group Treatment Vest Configuration

Group X Multi-array matrix of biocompatible microcells on RIGHT side of vest and placebo pattern on LEFT side of vest Group Y Multi-array matrix of biocompatible microcells on LEFT side of vest and placebo pattern on RIGHT side of vest Study Materials Participants will be provided the following study supplies:
a. Plastic vest replacements
b. Removable multi-array matrix of biocompatible microcells vest pad replacements
c. Supply of compression shirts
d. Study Log
e. Carrying tote for materials Participants will be instructed in the use of the multi-array matrix of biocompatible microcells vest, and will be supplied with detailed instructions for use.

Device Application Method

Before going to bed, patient will be instructed to apply the vest embodiment according to the provided instructions. Patients will moisten the pad of the vest and secure the vest to the body. They will wear a spandex t-shirt covering the entire vest. They will continue to wear the vest throughout the course of the night and remove the nighttime vest in the morning after awakening.

Patient Compliance Monitoring

Patients will be reminded to wear their study device by documenting wear through a paper log and/or electronic technology platform.

Automated Patient Communications

An automated patient communication portal, i.e. Constant Contact, SolutionReach, PracticeMojo, etc. will be used for patient compliance purposes. During the consent process, will have agreed to participate in automated text reminders. To remind patients to wear the study device each day, patients will receive a daily evening reminder on their cellular phone to wear the study device, as well as periodic reminders throughout the week (~3 times week) to change the vest pads. In the 2-way communication platform, participants will be requested to text "C" for confirming compliance. To ensure patient confidentiality and privacy, all text communications will comply with all applicable rules and regulations—see Appendix 1.

Deviations:

Participants will be asked to document all deviations from study procedures, and log dates where the vest was not worn due to extenuating circumstances.

Study Period
a. Visit 0—Baseline Visit 1—Week 2
b. (Day 14±2), Visit 2—Week 4 (Day 28±2), Visit 3—Week 6
c. (Day 42±2).

Study Enrollment
Consent form/Minor Consent
Medical History
Baseline Acne Grading
Digital Photos
Skin Evaluation
Vest distribution
Standard Follow-up Procedures:
Digital Photos
Skin Evaluation
Acne Grading
Vest distribution
Standard Follow-up Procedures
Digital Photos
Skin Evaluation
Acne Grading
Vest distribution
Standard Follow-up Procedures
Digital Photos
Skin Evaluation
Acne Grading
End of Study
Clinic Visits
a. Patients will be seen at the clinic for a total of four visits during the study, with baseline visit 0 serving as the initial visit. Follow-up visits will occur when the participants return to the clinic at weeks 2, 4 and 6 after the initial baseline visit for their follow-up evaluations.

Clinic Assessments
Initial Intake
Basic patient demographic information will be collected at the initial study visit, including:
a. Age
b. Gender
c. Past acne treatments d. Other skin conditions and/or relevant medical conditions The following study procedures will be performed at each visit:

Clinician Acne Grading: At the initial and each follow-up visit, the acne lesions will assessed by a physician extender, who will be blinded to the patients' randomization. Five separate evaluations will be performed at each visit and will be documented on case report form.
- a. 1) Leeds Rating: Grading of acne severity will be conducted according to the Leeds Acne Grading System, an overall assessment of acne severity for use in routine clinic, which grades patients on a scale of 0 (no acne) to 10 (the most severe). For the purpose of this study, only patients falling in between grades 1-5 will be included.

2) Clinical Evaluation
- a. A standard skin assessment, evaluating presence of infection, erythema, and irritation will be documented.

3) Lesion Count
- a. The area of the back above the scapula will be divided into four equal quadrants: Left upper, left lower, right upper and right lower. The physician extender will count and document the number of lesions observed in each quadrant.

4) Global assessment
- a. Efficacy of each treatment will be investigated by global assessment; the physician extender will assess if the global acne appearance on each half of the back has improved, is the same, or has worsened compared to the baseline photo.

5) Side by Side assessment
- a. The physician extender will perform a "side-by-side" evaluation to evaluate the appearance of acne of the left side compared to the right side of the back, and document if the left or right side of the back looks better, or the same.

Photograph
- a. Standardized digital photography to capture progressive changes in acne lesions over time will be performed at each visit. A standard photography station will be set up at each clinic site, with digital camera mounted on tripod. The back will be photographed according to the following standards:
- b. Angle: The photo is to be taken perpendicular to the back
- c. Lighting: The photo is to be taken under the same lighting conditions.
- d. Height: The photo is to be taken at a standard height for each patient, with height adjustable as needed.
- e. Necessary information to accompany each photo: Label with participant # and date
- f. Number of photos: Photos will be obtained at each follow-up visit; a total of 4 photographs will be taken: Baseline, Week 2, Week 4, and Week 6 of study.
- g. Pre and post-treatment photos will be overlaid for comparison.

Patient Acne Assessment
- a. At the follow-up visits, patients will evaluate photos of their back at the current study visit and self-report on the following: general appearance of acne, redness and discomfort of acne lesions.
- b. Patient clinical assessment will be documented on case report form "Patient Acne Assessment" XV-060CRF-06.

Wearability Assessment
- a. Participants will also answer a questionnaire at their last visit to assess their experience with the vest. Participants will rate comfort level (vest, strap, moisture, temperature, sleep quality) and other observations during the study. Outcomes will be captured on "Wearability assessment" XV-060CRF-08.

Blinded Clinician Photo Assessment
- a. Photos will be graded per by two independent clinicians, with a third clinician brought in if tie-breaking is required. Clinicians will be provided digital photos of each participant, with photos out of chronologic order In the first series of four photos, clinicians will perform a "side by side" comparison evaluating left side of back versus right side of back in each of the photos, and selecting which side appears better, Left- Right- or if they appear the Same.

In the second series of three photos, clinicians will perform a global assessment evaluating left half of back versus baseline photo, and right half of back versus baseline photo. Baseline photo is labeled but subsequent photos are not in chronologic order.

Study Endpoint

The study will end 6 weeks after first day of enrollment in the study. All patients will be monitored for adverse side effects including but not limited to infection, skin sensitivity, and worsening condition of the acne condition during the course of the study.

Study Outcomes: All patients will be assessed for:
- a. Acne improvement via Leeds System and clinical skin assessment
- b. Visual acne improvement via digital photography
- c. Wearability assessment via patient survey
- d. Patient self assessment of acne clinical condition Example 12

Preventing Viral Propagation

A mammal infected with MERS wears a disclosed "insert" embodiment inside an N95 mask to prevent viral propagation. The insert is moistened with saline prior to use.

Example 13

Preventing Viral Propagation

A mammal infected with a corona virus wears a disclosed "insert" embodiment inside an N95 mask to prevent viral propagation. The insert is moistened with saline prior to use.

Example 14

Preventing Viral Acquisition

A healthy mammal wears a disclosed insert embodiment with a medical mask to prevent viral acquisition. The insert is affixed outside the mask with adhesive.

Example 15

Preventing Viral Acquisition

A healthy mammal wears a disclosed embodiment to prevent viral acquisition. The insert is moistened with saline prior to use.

Example 16

Viral Proliferation Test

A disclosed embodiment was tested against several viral strains. According to the results, there was 100% kill after a $10^4$ PFU viral challenge/sample.

| Virus Kind | Influenza Virus | Feline Calcivirus |
|---|---|---|
| Virus Strain | Influenza A Virus (H3N2) Influenza A Virus (H1N1) | Feline calicivirus Strain: F-9 |
| Host Cell | MCDK Cell (Dog kidney cell origin) | CRFK Cell (Cat kidney cell origin) |

| Results | | | | | |
|---|---|---|---|---|---|
| Time | # of Plaques of Fabrics (Vomaris) | | | | |
| point | Blank | Zinc | Silver | Procellera | Notes |
| T30 | TMTC | TMTC | 0 | 0 | |
| T60 | TMTC | TMTC | 0 | 0 | |

TMTC, too many to count plaques

The antiviral effects were observed within minutes of exposure, as shown in FIG. 27 and FIG. 28.

Example 17

Coronavirus Test

Electroceutical Fabric for PPE Against COVID-19

Abbreviations

COVID-19—Coronavirus Disease of 2019; CDC—Center for Disease Control 23 and Prevention; PPE—personal protective equipment; SEM—Scanning electron microscopy; CoV 24—Coronavirus; SARS—Severe acute respiratory syndrome; CPE—Cytopathic effects; WHO—25 World Health Organization; FDA—Food and Drug Administration; NTA—Nanoparticle tracking 26 analysis; EDX—Energy Dispersive X-ray microanalysis; kV—kilovolt; keV—kilo electronvolt; 27 ddH2O—ultra-pure water; GFP—green fluorescent protein; MTT-3-(4,5-dimethylthiazol-2-yl)-28 2,5-diphenyl tetrazolium bromide In this work we tested the hypothesis that an electroceutical fabric will disrupt the infectivity of coronavirus upon contact by destabilizing the electrokinetic properties of the viral particle. A respiratory coronavirus (USDA permit 141794) and the corresponding mammalian ST cell were obtained from ATCC to study the cytopathic effects of viral infection. Viral particles (105) were placed in direct contact with the electroceutical or sham fabric for either 1 or 5 minutes. Viral particles ($4 \times 10^4$) were recovered from the fabric and subjected to nanoparticle tracking analysis and measurement of zeta potential. Recovered viral particles were subjected to cytopathic testing and studied for 7 days following infection. Under conditions of cytopathic testing, the electroceutical fabric generated a weak potential difference of 0.5V. Following one minute of contact, zeta potential of the coronavirus was significantly lowered indicating destabilization of its electrokinetic properties. Size-distribution plot showed appearance of aggregation of the virus. Testing of the cytopathic effects of the virus showed eradication of infectivity as quantitatively assessed by calcein-PI and MTT cell viability tests. This work presents first evidence demonstrating that the physical characteristic features of CoV may be exploited to render it non-infective following exposure to weak electric field generating electroceutical fabric. The effect is rapid and achieved within one minute of contact. The supporting observation that lentiviral infectivity is also eliminated following contact with the electroceutical fabric contributes to the rigor of our central finding.

Results

Characterization of the Electroceutical Fabric

The electroceutical fabric tested is made up of polyester fabric printed with alternating circular regions of Ag and Zn dots. Ag dots (2 mm) and Zn dots (1 mm) were printed on the fabric in proximity of about 1 mm to each other. Scanning electron microscopy (SEM) displayed the deposition of Ag particles and Zn on the fibers of the polyester fabric. Energy Dispersive X-ray (EDX) microanalysis revealed the presence of Ag and Zn on the electroceutical fabric (fe) and absence in the sham polyester fabric (fs). The only peak that was present other than C and O was that of Au used for coating the fabrics for SEM imaging. Proximity of Ag and Zn on polyester fabric forms a redox couple and is capable of driving electrochemistry when wet in an aqueous ionized environment including any body fluid. Ag and Zn were spotted on another textile which was also appropriate for the preparation of stretchable face-masks. SEM of the fabric used for such mask showed a different weaving pattern aimed at higher stretch property. Deposition of Ag and Zn on the fabric for face-mask was tested by EDX spectrum analysis. Our primary line of investigation focused on the polyester-based electroceutical fabric which may be utilized for the development of PPE as well. Three ionized aqueous media were used to test potential difference between adjacent Ag and Zn deposits. NaCl solution (0.85% w/v), cell culture medium and tap water (of practical value to end users of PPE) were tested at room temperature. The potential difference between the two electrodes rapidly increased and achieved a steady state after the first 15 s.

Physical Characterization of the Coronavirus

SEM (150,000×) revealed the morphological features of the CoV particle. Following spotting on the silicon wafer, the purified virus was fixed and subsequently dehydrated. A thin (2-132 5 nm) layer of carbon was sputtered on the sample to make the specimen conductive. The size of the virus ranged between 75-125 nm. Nanoparticle tracking analysis (NTA) revealed poly-134 dispersed peak. The electrokinetic property, as represented by the zeta potential, of the viral particles is a parameter that determines adsorption and stability of the particle in any given dispersant medium. For practical purposes, viral particles are expected to be suspended in water droplets either aerosolized or resting on a surface. The average zeta potential of four different preparation of CoV was determined to be −25.675 mV. All four-preparation demonstrated comparable zeta potential distribution and phase shift. The average electrophoretic mobility distribution was determined to be −2 μmcm/Vs.

Electroceutical Fabric Attenuated the Zeta Potential of Coronavirus Upon Contact Quantification of the purified viral particles after spotting on fe yielded 44.29% and 23.73% recovery from the fabric when exposed for 1 min or 5 min, respectively (FIG. 29A). Nanoparticle tracking analysis demonstrated that unlike the purified CoV that showed a single peak around 75 nm, the recovered CoV showed additional peaks suggesting aggregation of the viral particles upon contact with the fabric (FIG. 29B). Analysis of □ potential showed significant graded attenuation of this electrokinetic property upon contact with the fe (FIG. 29C). Such lowering of average zeta potential of CoV, applied and recovered from fe, has been plotted graphically (FIG. 29D). Unlike 1 min exposure to the fe, 5 min exposure showed an appreciable difference in the phase plot of the viral particles (FIG. 29E).

Loss of Corona Virus Infectivity Upon Contact with Electroceutical Fabric

To assess changes in the infectivity of CoV following contact with the electroceutical fabric, a cytopathic assay was employed. Infected cells were monitored for appearance of cytopathic effects (CPE; cell rounding and sloughing) until post-infection day 7. Overt CPE was observed on day 7 in response to CoV infection (FIG. 30B; FIG. 33). Comparable CPE was noted in response to treatment of cells with CoV recovered from sham control fabric fs (FIG. 30C; FIG. 33). In contrast, CoV recovered from fe did not cause any CPE indicating loss of its infectivity (FIG. 30D; FIG. S2). Cells treated with fe-recovered CoV particles appeared as healthy as the uninfected cells (FIG. 30A; FIG. 33). Objective assessment of cell viability was performed using a calcein/PI fluorescence assay. Only live cells with intracellular esterase activity hydrolyze the acetoxymethyl ester in non-fluorescent Calcein AM converting it into green fluorescent Calcein. Dead cells or cells with damaged or compromised cell membranes include PI stain, which is otherwise impermeant to live cells. Fold-change increase in PI/Calcein signal as shown indicates loss of cell viability in response to infection. Infection of cells with CoV caused marked loss of cell viability (FIG. 30B). Such cytopathic effect of CoV was completely absent once the virus was exposed to fe (FIG. 30 D-E). The sham fabric did not afford such protection (FIG. 30C,E). The cytopathic effects of CoV and the protective effects of fe (versus fs) was corroborated by the standard MTT assay commonly used for testing cell viability (FIG. 30F).

Electroceutical Fabric Eliminated Lentiviral Transduction Efficacy

The Lentiviral pseudotype system is a standard laboratory tool to study the infectivity of viruses under conventional biosafety conditions. Lentivirus CSCGW mut6, upon successful transduction in HEK293 cells, results in GFP-expressing host cells. This expression is a direct measure of lentiviral replication competency and ability of the virus to integrate in the host genome. The ability of the electroceutical fabric to influence the infectivity of a virus, other than CoV, was tested to appreciate its broader significance of scope. Mammalian cells were treated with purified lentivirus or the same virus subjected to contact with fe or fs for 1 or 5 mins as indicated in the figure legend (FIG. 31). Transduced cells were monitored microscopically to check the presence of GFP+ cells, a marker of successful infection. Lentiviral exposure caused widespread infection of cells. Treatment of cells with virus recovered from sham fabric fs caused comparable infection (FIG. 31B). However, contact of virus with the electroceutical fabric fe, even for one minute, eliminated lentiviral infectivity (FIG. 31B).

DISCUSSION

Previous work from our laboratory has established the effectiveness of electroceutical principles as an alternative to pharmacological approaches in managing planktonic microbial pathogens and complex polymicrobial biofilms. The currently studied electroceutical fabric is simple in configuration not requiring any complex wiring or power source. It is thus easy to use in a field setting and requires no training or skills. The textile itself is comparable to any other standard textile lending itself for manufacturing of PPE. Viruses are known to rely on electrostatic interactions for optimal virion assembly and attachment. For instance, structural proteins in coronaviruses, negatively charged amino acid residues in the nucleocapsid facilitates assembly with the membrane protein. Additionally, the coronavirus envelope protein is known to generate ion conductive pores across membranes which are voltage dependent23. Leveraging these viral characteristics to achieve viral inactivation remains largely unexplored and has been attempted in this work.

Electroceuticals have generated renewed interest in the health care industry. This work presents the first evidence demonstrating that the infectivity of the CoV may be disrupted using a simple electroceutical fabric. The fabric tested in this work consists of only silver and zinc dots on polyester fabric that forms a redox couple. This work demonstrates that CoV infectivity may be rapidly eradicated upon contact with the electroceutical fabric. Zeta potential of a particle determines its electrostatic interactions in particle dispersions and, as such, is an important determinant of the stability of viral particles. Contact of CoV with the electroceutical fabric studied rapidly lowered the zeta potential demonstrating a direct effect of the fabric on the electrokinetic properties of the viral particle. Any change of zeta potential towards zero is viewed as increase in electrical instability of the particle. The observation that contact with the electroceutical fabric eliminates infectivity of the virus leads to the hypothesis that the observed lowering of zeta potential may have caused defects in the structural integrity of the virus. Study of changes in the capsid-RNA structure following exposure to the weak electric field generated by the fabric is thus warranted. CoV is a nanoparticle. Nanoparticle tracking analysis determines the hydrodynamic diameter of the analyte by applying the Stokes-Einstein equation after measuring the Brownian motion of individual nanoparticle. It is an alternative method to dynamic light scattering which utilizes the same principle and is validated for assessing polydispersity and purity in viral vaccine preparations. NTA was therefore utilized to estimate absolute viral particle number and size distribution in not only pure CoV but also in CoV recovered from the fabric. Observed changes in particle number and size distribution support the aforementioned hypothesis that exposure to the weak electric field causes damaging structural alterations to the virions. Cells in culture routinely display a small fraction of dead or dying cells. Cytopathic effects of viral infection are tested to examine whether exposure to the infectious particle adds to the basal cell death burden of the culture. Long-term observations, i.e. days versus hours, ensure the recording of the eventual fate of the affected cells. Reporting of short-term data alone, while sometimes may be encouraging with respect to effect of the intervention, may simply reflect results representing postponement of death from the insult and not a true rescue. In CPE studies of this work, cell rounding and sloughing were evident in day 4 post-infection. During this time, cells treated with virus pre-exposed to the electroceutical fabric closely resembled cells that were unchallenged by exposure to the virus. In standard cell culture, the growth medium is changed every other day to wash off floating dead cells and to replenish nutrition. Under conditions of infection by virus, such frequent change of cell culture medium is not made. Cells grow in the same spent media until day 7 post-infection. Maintenance of cells without any change in culture media for seven days is expected to marginally increase basal cell death burden as shown.

Textiles evaluated for use in PPE such as masks are subject to specific FDA 510(k) requirements expecting stringent viral filtration tests to demonstrate 99.9% reduction of $1.1$-$3.3 \times 10^4$ plaque forming units of standard phiX174 bacteriophage. The phiX174 is widely used as a model organism because of it being a standardized test. However, it is important to note that unlike SAR-241 CoV-2 which is a RNA virus, phiX174 bacteriophage is a DNA virus with numerous contrasting physical, chemical as well as biological properties. Furthermore, this bacteriophage is much smaller in size than SAR-CoV-2. The non-enveloped icosahedral morphology of phiX174 bacteriophage aerosolizes with a mean particle size of $3.0 \pm 0.3$ µm 25. This is in direct contrast with the coronaviruses that cause diseases in animals and humans which are ~100 nm in diameter and are aerosolized as respiratory droplets with sizes >5 µm. Importantly, phiX174 cannot and are aerosolized as respiratory droplets with sizes >5 µm. Importantly, phiX174 cannot infect mammalian cells. It infects and forms visible plaques on a lawn of Escherichia coli (Migula) Castellani and Chalmers strains. In the context of COVID-19 pandemic, our study focuses on coronavirus and tests cytopathic effects on mammalian cells. Testing methods such as AATCC 250 TM100 recommends a textile contact time of 24 h for both enveloped and non-enveloped viruses. We report results on contact time that is much shorter and more relevant to PPE usage in the context of COVID-19. Additional studies in our laboratory show effective neutralization of a wider range of viruses at a much higher load (108) within 1-2 h of textile contact time (not shown).

This work presents first evidence demonstrating that the physical characteristic features of CoV may be exploited to render it non-infective following exposure to weak electric field generating electroceutical fabric. The effect is rapid and achieved within one minute of contact. The observation that lentiviral infectivity is also eliminated following contact with the electroceutical fabric contributes to the rigor of our central finding. Lowering of zeta potential of the CoV particles following exposure to the electroceutical fabric constitutes direct evidence supporting the contention that electrokinetic stability of the viral particle is weakened. Additional studies are necessary to characterize specific structural changes in response to exposure to the electroceutical fabric, and to connect such changes to loss of infectivity. In the meantime, this work provides compelling first evidence to consider the studied electroceutical fabric, or other materials with similar property, as material of choice for the development of PPE in the fight against COVID-19.

Materials and Methods

Electroceutical Fabric 2

An FDA cleared wireless electroceutical dressing was used as a source of weak electric field for the current study and is referred to as electroceutical fabric (fe). This fabric, co-developed by our laboratory, has been commercialized by Vomaris Inc. (Phoenix, Ariz.) was provided to us by the manufacturer. It is made of polyester fabric printed with alternating circular dots of Ag and Zn metals (2 mm and 1 mm, respectively), generating electric fields. A polyester fabric without any metal deposition (hence unable to generate electric field) was used as an experimental control and is referred to as sham fabric (fs).

Viruses and Cell Lines

Respiratory coronavirus (ATCC® VR-2384™) and its host porcine cell line—ST (ATCC® CRL-278 1746™), recommended for its infection and propagation were procured from ATCC (Manassas, Va.).

Cell Culture

Cell lines were cultured and maintained in respective cell culture medium, in either T25 or T75 flasks (Cat no: 82051-074 and 82050-856, Greiner Bio-One, Monroe, N.C.), at 37° C. and humidified 5% CO2 in air atmosphere. All culture media were made complete by addition of Fetal Bovine Serum (FBS, final concentration 10%; Cat no: F2442-500ML, Sigma-Aldrich, St. Louis, Mo.) and Antibiotic-Antimycotic solution (final concentration 1×; Cat no: 15240-062, Life Technologies, Carlsbad, Calif.). For coronavirus studies, ST cells were cultured in complete Eagle's Minimum Essential Medium (EMEM, ATCC® 30-2003™). HEK293 cells were cultured in complete Dulbecco's Modified Eagle's Medium (DMEM, Cat no: 11995073, Gbco™, Gaithersburg, Md.). For sub-culturing HEK293 cells, culture medium was discarded from flasks and cells (85-90% confluent) were rinsed briefly with 5 ml of 1X phosphate buffered saline (PBS; Cat no: 20012027, Gibco™, Gaithersburg, Md.) to remove all traces of serum. Cells were detached by adding of 2-3 ml of 0.05% Trypsin-EDTA solution (Cat no: 25300054, Gbco™, Gaithersburg, Md.) and incubation at 37° C. for 15 minutes. Respective complete growth medium (~4-6 ml) was added to the flasks. Detached cells were aspirated with gentle pipetting and this cell suspension was centrifuged at 500×g for 3 mins at 28° C. (Beckman Coulter Allegra x-14r-SX4750). Post centrifugation, supernatant was discarded, and cells were thoroughly re-suspended in either 5 ml (for T25 flask) or 12 ml (for T75 flask) of complete growth medium followed by addition in new culture flasks and incubation as mentioned earlier. For cryopreservation, cells were trypsinized and pelleted as above to re-suspend in 2 ml of complete growth medium with 5% (v/v) dimethyl sulfoxide (Cat no: BP231-100, Fisher Scientific, Waltham, Mass.). These cells were first stored at −20° C. for 3 h, followed by storage at −80° C. for 24 h and final storage in liquid nitrogen.

Respiratory Coronavirus (CoV) Infection and Propagation

ST cells were cultured in complete EMEM till they attained a confluency of 80-90% followed by washing monolayers with 5 ml of 1×PBS. USDA permit 141794 (Dr. Sen) was obtained for the procurement and laboratory use of coronavirus. Coronavirus stock (ATCC VR-2384) was thawed at 37° for 5 min and aliquots of 250 µl were prepared for further use or storage in liquid nitrogen.

An aliquot of this stock was diluted with 3 ml of incomplete culture medium (without FBS and Antibiotic-Antimycotic solution) to attain a Multiplicity of Infection (MOI) of 1 as per ATCC recommendations. This diluted viral stock was added to the washed monolayer and incubated at 37° C., humidified 5% CO2 in air atmosphere. Flasks were rocked gently for 2 min at intervals of 315 30 min, to re-distribute viral inoculum. Post 2 h infection, viral adsorption was ended by adding 10 ml of complete culture medium to the monolayer. Cells were monitored microscopically every 24 h for signs of cytopathic effects (CPE. Flasks showing CPE in 80% of the infected host cells were used for viral purification.

Coronavirus Purification

The protocol adopted for viral purification was as per Maier et al., 201529. Culture medium from flasks with infected cells was harvested at 10000×g for 20 mins at 4° C. (Beckman Coulter Allegra x-14r-FX6100). Viral precipitation from this supernatant (12 ml) was done by addition of polyethylene glycol (PEG-6000, final concentration 10%; Cat no: 81260, Sigma-Aldrich, St. Louis, Mo.) and NaCl (final concentration 2.2%; Cat no: S271, Fisher Scientific, Waltham, Mass.). PEG-6000/NaCl/culture supernatant mixture was incubated at 4° C. for 30 minutes. PEG precipitated proteins and virions were pelleted at 10000×g for 30 min at 4° C. and the pellet was dissolved in 100 µl of ice-cold 1X HEPES-saline buffer (10 mM HEPES—Sigma H7523+ 0.9% w/v NaCl, pH 6.7). Dissolved pellet was then loaded on a discontinuous sucrose gradient (10-20-30%, 800 µl each; freshly prepared in 1× HEPES-saline) and subjected to ultracentrifugation at 100000×g for 90 mins at 4° C. (Beckman Coulter Optima MAX-XP Ultracentrifuge). Post ultracentrifugation, the supernatant was discarded, and the viral pellet was dissolved in 100 µl of 1× HEPES-saline buffer (pH 7.4). Total viral particle number estimation was performed using 17

Nanoparticle Tracking Analysis (NTA) and purified viruses were flash frozen in dry ice followed by storage in liquid nitrogen, till further use.

Nanoparticle Tracking Analysis

Viruses were diluted in EMEM (ATCC® 30-2003™) or 18.2 MΩ water. Mean particle diameter and concentration of viral particles were analyzed by NanoSight NS300 with a 532 nm laser and SCMOS camera (Malvern, Worcestershire, UK) as previously described30 31. Briefly, samples were diluted 100:1 or as needed in fresh milliQ to obtain 5-100 particles/frame. Samples were typically analyzed using 5 runs of 30 s collecting 25 frames per second (749 frames per run) with viscosity determined by the temperature and camera level highest available for sample (typically 15 or 14). The syringe pump speed was 60. NTA automatically compensates for flow in the sample such that only Brownian motion is used for size determination. For processing results, the detection threshold was typically 5 with automated blur size and max jump distance. Standard 100 nm latex spheres were run at 1000:1 dilution in milliQ to test optimal instrument performance. Data were analyzed usung NTA 3.0 software (Malvern Instruments Ltd., UK).

Zeta Potential Analysis

Zeta potential measurement of viral particles was determined by Zetasizer (Nano-Z, Malvern Instruments Ltd., UK) as described previously30, 31. All samples were dispersed in double-distilled water and tested in volume-weighted size distribution mode in folded capillary cells (Fisher Scientific NC0491866). An average of three readings (60 s) were recorded.

Scanning Electron Microscopy of CoV

Viral particles were suspended in ddH$_2$O with 2.5% glutaraldehyde or other buffer and dropped onto dean silica wafers. After drying, samples were desiccated in a vacuum chamber for at least 12 h before analysis. Images were obtained after carbon sputter coating using a field emission scanning electron microscope (JEOL 7800F, JEOL Japan) at a beam energy of 5 or 10 kV. For the SEM images of the fabric, gold sputter coating was used.

Energy Dispersive X-Ray Microanalysis

For elemental detection, the Energy Dispersive X-ray (EDX) microanalysis associated to scanning electron microscopy was used. When the electron beam hits the gold sputtered fabric, some atoms of the sample are excited or ionized. When excited or ionized atom return to their ground state, they emit characteristic x-rays. The x-ray emissions at different wavelengths were measured using a photon-energy-sensitive detector. The EDX detector system performs a simultaneous display of all mid-energy (1-20 keV) x-rays collected during any individual analysis period.

Coronavirus and Lentivirus Infectivity

ST (coronavirus) and HEK 293 (lentivirus) cells were seeded at densities of 10,000/well and 1000/well in 24-well and 96-well cell culture plates, respectively. Seeded plates were incubated at 37° C., 5% CO$_2$ humidified incubator for 18 h. One hundred microliter (105 particles) of aqueous suspension of viruses (106/ml of VR-2384 and CSCGW mut6 lentivirus) were spotted on 1.5 cm diameter discs of fe and fs at room temperature. After an incubation period of 1 min or 5 min, 100 µl of serum free medium was used to rinse each fabric for recovering viral particles from the fabric. NTA was performed, as above, to estimate viral recovery efficiency.

Recovered VR-2384 viruses were diluted with serum free medium and used to infect ST cells at MOI of 10 (105 viruses). Recovered CSCGW mut6 virus was diluted in complete DMEM medium followed by HEK293 transduction at MOI of 10 (4×104 viruses). Parallel sets of cells infected with untreated viruses (at the same MOI as that of treated viruses) were used as positive control while uninfected or non-transduced host cells were accounted as negative control. Virus infected ST cells were monitored microscopically at intervals of 24 h for the onset and progression of cytopathic effects. The expression of GFP in transduced HEK293 was assessed after 4 days to ascertain the effect of fe treatment on lentiviral infectivity. Six technical replicates were assayed for each experimental group. Twelve biological replicates were studied.

Cell Viability Staining by Calcein AM and Propidium Iodide

Viability of ST cells, infected as above, was assessed by dual staining with Calcein AM and Propidium iodide (PI). Media from wells with ST cells (uninfected or infected with untreated or fabric-contacted viruses) was washed briefly with 1 ml of 1×PBS (per well) for 1 min, followed by addition of 250 µl of freshly-prepared staining solution in 1×PBS (Calcein AM; final concentration 1 µg/ml, Catalog no: C1430, Invitrogen™, Waltham, Mass.) and PI (final concentration 10 µg/ml, Catalog no: CAS 25535-16-4, Sigma-Aldrich, St. Louis, Mo.). Cells were incubated under dark conditions at 37° C. for 15 min and then observed under a Confocal Laser Scanning Microscope using a 10× objective. Multiple images (10 images per group/per set) were captured and fluorescence intensities were calculated from these images using Zen blue software and graphically plotted as shown. The ratio of PI:Calcein signal was normalized with the average PI intensity of untreated cells to obtain fold-change compared to non-viable cells (basal cell death) in untreated cells.

Cell Viability Assessment by MTT Assay

Cell viability of ST cells infected as above was assayed using the MTT (3-(4,5-Dimethylthiazol-2-yl)-2,5-diphenyltetrazolium bromide) assay. This assay was performed as per manufacturer's protocol (MTT assay kit, Catalog no: ab211091, Abcam, Cambridge, Mass.). ST cells were washed with 1 ml of 1×PBS per well and then harvested using a cell scraper. Cells were collected in tubes, centrifuged at 300×g for 5 min at room temperature followed by re-suspension in incomplete EMEM. Cells in this suspension were counted and cell count in all the experimental groups was normalized to 105 cells per 500 µl of culture medium. In separate 96-well tissue culture plates, 50 µl of the above suspension was added in each well (final cell counts as 104 cells). To each well, 50 µl of MTT solution was added and the plates were incubated at 37° C., 5% CO2 humidified incubator for 3 hours. After incubation, plates were centrifuged at 300×g for 5 min at room temperature and supernatant was discarded. One hundred and fifty microliters of MTT solvent was added to each well. Plates were wrapped in aluminum foil and rocked on an orbital shaker for 15 min followed by measurement of absorbance at 590 nm.

Statistical Analysis

GraphPad Prism (GraphPad Software) v8.0 was used for statistical analyses. Statistical analysis 419 between multiple groups were performed using one-way analysis of variance with the post hoc 420 Sidak multiple comparison test. Statistical analysis between two groups was performed using unpaired Student's two-sided t tests. P<0.05 was considered statistically significant. Significance levels and exact P values are indicated in all relevant figures. Data were normally distributed. Data for independent experiments were presented as means±SEM unless otherwise stated. Individual data points are plotted reflecting n (8-19) for each experiment.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, including the best mode known to the inventor for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A method for reducing coronavirus transmission through the mouth and nose comprising applying a low level micro-current (LLEC) of between 1 and 200 micro-amperes to the mouth and nose, wherein said LLEC reduces the infectivity of the coronavirus.

2. The method of claim 1 wherein applying comprises affixing an LLEC system comprising a pliable substrate comprising on its surface a multi-array matrix of biocompatible microcells.

3. The method of claim 2 wherein said multi-array matrix comprises:
 a first array comprising a pattern of microcells comprising a conductive material; and
 a second array comprising a pattern of microcells comprising a conductive material, such arrays capable of defining at least one voltaic cell for spontaneously generating at least one electrical current with the conductive material of the first array when said first and second arrays are introduced to an electrolytic solution.

4. The method of claim 3, wherein said transmission comprises viral propagation.

5. The method of claim 3, wherein said transmission comprises viral acquisition.

6. The method of claim 3, wherein said pliable substrate comprises an adhesive.

7. The method of claim 6, wherein said adhesive is present on opposite ends of the substrate.

8. The method of claim 7, wherein said adhesive is present around the perimeter of the substrate.

9. The method of claim 3, wherein the first array and the second array spontaneously generate a LLEF.

10. The method of claim 3, wherein the first array and the second array spontaneously generate a LLEC when contacted with an electrolytic solution.

* * * * *